(12) United States Patent
Surleraux et al.

(10) Patent No.: US 8,680,071 B2
(45) Date of Patent: Mar. 25, 2014

(54) COMPOUNDS AND PHARMACEUTICAL COMPOSITIONS FOR THE TREATMENT OF VIRAL INFECTIONS

(75) Inventors: Dominique Surleraux, Wauthier-Braine (BE); Gilles Gosselin, Montpellier (FR)

(73) Assignees: Idenix Pharmaceuticals, Inc., Cambridge, MA (US); Centre National de la Recherche Scientifique, Paris (FR)

( * ) Notice: Subject to any disclaimer, the term of this patent is extended or adjusted under 35 U.S.C. 154(b) by 382 days.

(21) Appl. No.: 13/077,733

(22) Filed: Mar. 31, 2011

(65) Prior Publication Data

US 2011/0243886 A1   Oct. 6, 2011

Related U.S. Application Data

(60) Provisional application No. 61/320,272, filed on Apr. 1, 2010.

(51) Int. Cl.
*C07H 19/20* (2006.01)
*C07H 19/10* (2006.01)
*C07F 9/24* (2006.01)

(52) U.S. Cl.
CPC ............. *C07H 19/20* (2013.01); *C07H 19/10* (2013.01); *C07F 9/24* (2013.01)
USPC ........................... 514/52; 536/26.7; 536/26.8

(58) Field of Classification Search
None
See application file for complete search history.

(56) References Cited

U.S. PATENT DOCUMENTS

| | | | |
|---|---|---|---|
| 3,480,613 A | 11/1969 | Walton | |
| 5,118,672 A | 6/1992 | Schinazi et al. | |
| 5,149,794 A | 9/1992 | Yatvin et al. | |
| 5,455,339 A | 10/1995 | Chu et al. | |
| 5,627,185 A | 5/1997 | Gosselin et al. | |
| 6,071,922 A | 6/2000 | Schinazi et al. | |
| 6,348,587 B1 | 2/2002 | Schinazi et al. | |
| 6,555,676 B2 | 4/2003 | Gosselin et al. | |
| 6,653,296 B1 | 11/2003 | Holy et al. | |
| 6,660,721 B2 | 12/2003 | Devos et al. | |
| 6,752,981 B1 | 6/2004 | Erion et al. | |
| 6,777,395 B2 | 8/2004 | Bhat et al. | |
| 6,784,166 B2 | 8/2004 | Devos et al. | |
| 6,787,526 B1 | 9/2004 | Bryant et al. | |
| 6,812,219 B2 | 11/2004 | LaColla et al. | |
| 6,846,810 B2 | 1/2005 | Martin et al. | |
| 6,849,726 B2 | 2/2005 | Usman et al. | |
| 6,852,535 B1 | 2/2005 | Thompson | |
| 6,914,054 B2 | 7/2005 | Sommadossi et al. | |
| 6,927,291 B2 | 8/2005 | Jin et al. | |
| 6,984,634 B2 | 1/2006 | Cundy et al. | |
| 7,022,828 B2 | 4/2006 | McSwiggen | |
| 7,034,009 B2 | 4/2006 | Pavco et al. | |
| 7,041,817 B2 | 5/2006 | Usman et al. | |
| 7,094,770 B2 | 8/2006 | Watanabe et al. | |
| 7,101,861 B2 | 9/2006 | Sommadossi et al. | |
| 7,105,493 B2 | 9/2006 | Sommadossi et al. | |
| 7,105,499 B2 | 9/2006 | Carroll et al. | |
| 7,109,165 B2 | 9/2006 | Matulic-Adamic et al. | |
| 7,125,855 B2 | 10/2006 | Bhat et al. | |
| 7,144,877 B2 | 12/2006 | Gallop et al. | |
| 7,157,441 B2 | 1/2007 | Sommadossi et al. | |
| 7,176,304 B2 | 2/2007 | McSwiggen et al. | |
| 7,202,224 B2 | 4/2007 | Eldrup et al. | |
| 7,429,572 B2 | 9/2008 | Clark | |
| 7,601,820 B2 | 10/2009 | Wang et al. | |
| 7,608,600 B2 | 10/2009 | Storer et al. | |
| 2002/0120129 A1 | 8/2002 | Beigelman et al. | |
| 2003/0060400 A1 | 3/2003 | LaColla | |
| 2003/0219727 A1 | 11/2003 | Becker et al. | |
| 2004/0023901 A1 | 2/2004 | Cook | |
| 2004/0063658 A1 | 4/2004 | Roberts et al. | |
| 2004/0121980 A1 | 6/2004 | Martin et al. | |
| 2004/0209831 A1 | 10/2004 | McSwiggen et al. | |
| 2004/0229839 A1 | 11/2004 | Babu et al. | |
| 2004/0229840 A1 | 11/2004 | Bhat et al. | |
| 2005/0009737 A1 | 1/2005 | Clark | |
| 2005/0038240 A1 | 2/2005 | Connolly et al. | |
| 2005/0182252 A1 | 8/2005 | Reddy et al. | |
| 2005/0191302 A1 | 9/2005 | Arthur et al. | |
| 2005/0203243 A1 | 9/2005 | Polus | |
| 2005/0215510 A1 | 9/2005 | Roberts et al. | |
| 2006/0040890 A1 | 2/2006 | Martin et al. | |
| 2006/0046980 A1 | 3/2006 | Erion et al. | |
| 2006/0111324 A1 | 5/2006 | Choi et al. | |
| 2006/0234962 A1 | 10/2006 | Olsen et al. | |
| 2006/0286615 A1 | 12/2006 | Lederkremer et al. | |
| 2007/0037221 A1 | 2/2007 | Block et al. | |
| 2007/0037735 A1 | 2/2007 | Gosselin et al. | |
| 2007/0042939 A1 | 2/2007 | LaColla | |
| 2007/0042940 A1 | 2/2007 | LaColla et al. | |
| 2007/0042990 A1 | 2/2007 | Gosselin et al. | |
| 2007/0042991 A1 | 2/2007 | LaColla et al. | |
| 2007/0060498 A1 | 3/2007 | Gosselin et al. | |
| 2007/0060503 A1 | 3/2007 | Gosselin et al. | |
| 2007/0060504 A1 | 3/2007 | Gosselin et al. | |
| 2007/0060505 A1 | 3/2007 | Gosselin et al. | |

(Continued)

FOREIGN PATENT DOCUMENTS

| | | |
|---|---|---|
| CN | 101333235 A | 12/2008 |
| EP | 1655033 | 10/2006 |

(Continued)

OTHER PUBLICATIONS

Jones et al., "Synthesis and anti-HIV activity of some novel phosphorodiamidate derivatives of 3'-azido-3'-deoxythymidine (AZT)" Antiviral Chemistry and Chemotherapy (1991) vol. 2 No. 2 pp. 35-39.*

(Continued)

*Primary Examiner* — Eric S Olson
(74) *Attorney, Agent, or Firm* — Jones Day

(57) ABSTRACT

Provided herein are compounds, compositions and methods for the treatment of liver disorders, including HCV infections. In one embodiment, compounds and compositions of nucleoside derivatives are disclosed, which can be administered either alone or in combination with other anti-viral agents.

30 Claims, No Drawings

(56) References Cited

U.S. PATENT DOCUMENTS

| | | |
|---|---|---|
| 2007/0060541 A1 | 3/2007 | Gosselin et al. |
| 2007/0087960 A1 | 4/2007 | Storer et al. |
| 2008/0261913 A1 | 10/2008 | Sommadossi et al. |
| 2009/0280086 A1 | 11/2009 | Sommadossi et al. |
| 2012/0251487 A1* | 10/2012 | Surleraux .................... 424/85.2 |

FOREIGN PATENT DOCUMENTS

| | | |
|---|---|---|
| GB | 1209654 | 10/1970 |
| WO | WO 88/00201 | 1/1988 |
| WO | WO 97/12033 | 4/1997 |
| WO | WO 98/53813 | 12/1998 |
| WO | WO 99/43691 | 9/1999 |
| WO | WO 01/32153 | 5/2001 |
| WO | WO 01/60315 | 8/2001 |
| WO | WO 01/79246 | 10/2001 |
| WO | WO 01/90121 | 11/2001 |
| WO | WO 01/92282 | 12/2001 |
| WO | WO 01/96353 | 12/2001 |
| WO | WO 02/18369 | 3/2002 |
| WO | WO 02/18404 | 3/2002 |
| WO | WO 02/32920 | 4/2002 |
| WO | WO 02/48165 | 6/2002 |
| WO | WO 02/057287 | 7/2002 |
| WO | WO 02/057425 A2 | 7/2002 |
| WO | WO 03/062256 A1 | 7/2003 |
| WO | WO 03/070750 | 8/2003 |
| WO | WO 03/105770 A2 | 12/2003 |
| WO | WO 2004/002422 A2 | 1/2004 |
| WO | WO 2004/002999 | 1/2004 |
| WO | WO 2004/003000 A2 | 1/2004 |
| WO | WO 2004/003138 A2 | 1/2004 |
| WO | WO 2004/009020 A2 | 1/2004 |
| WO | WO 2004/022999 | 3/2004 |
| WO | WO 2004/072090 A1 | 8/2004 |
| WO | WO 2004/096233 A2 | 11/2004 |
| WO | WO 2004/096234 A2 | 11/2004 |
| WO | WO 2004/096237 A2 | 11/2004 |
| WO | WO 2004/096285 A2 | 11/2004 |
| WO | WO 2004/096286 A2 | 11/2004 |
| WO | WO 2004/096287 A2 | 11/2004 |
| WO | WO 2004/100960 A2 | 11/2004 |
| WO | WO 2004/000858 A2 | 12/2004 |
| WO | WO 2005/012525 A1 | 2/2005 |
| WO | WO 2005/021568 | 3/2005 |
| WO | WO 2005/044279 A2 | 5/2005 |
| WO | WO 2005/044308 A2 | 5/2005 |
| WO | WO 2005/087788 | 9/2005 |
| WO | WO 2006/012078 | 2/2006 |
| WO | WO 2006/012440 | 2/2006 |
| WO | WO 2006/116557 | 2/2006 |
| WO | WO 2006/063149 | 6/2006 |
| WO | WO 2006/093987 A1 | 9/2006 |
| WO | WO 2006/094347 A1 | 9/2006 |
| WO | WO 2006/116512 A1 | 11/2006 |
| WO | WO 2007/020193 A2 | 2/2007 |
| WO | WO 2007/095269 A2 | 8/2007 |
| WO | WO 2008/062206 | 5/2008 |
| WO | WO 2008/082602 | 7/2008 |

OTHER PUBLICATIONS

Hu et al., "One-Pot Synthesis of 5'-Diaryl Esters and Diamidates of Phosphate, Phosphorothioate, and Phosphoroselenoate Derivatives of AZT and d4T" Synthetic Communications (2009) vol. 39 pp. 1342-1354.*
Saboulard et al., "Characterization of the Activation Pathway of Phosphoramidate Triester Prodrugs of Stavudine and Zidovudine" Molecular Pharmacology (1999) vol. 56 693-704.*
McGulgan et al., "Phosphoramidate ProTides of the Anticancer Agent FUDR Successfully Deliver the Preformed Bioactive Monophosphate in Cells and Confer Advantage over the Parent Nucleoside" Journal of Medicinal Chemistry (2011) vol. 54 pp. 7247-7258.*

U.S. Appl. No. 60/392,350, filed Jun. 28, 2002, Sommadossi.
U.S. Appl. No. 60/466,194, filed Apr. 28, 2003, Sommadossi.
U.S. Appl. No. 60/470,949, filed May 14, 2003, Sommadossi.
U.S. Appl. No. 60/474,368, filed May 30, 2003, Clark.
U.S. Appl. No. 10/608,907, filed Jun. 27, 2003, Sommadossi.
U.S. Appl. No. 11/854,218, filed Sep. 12, 2007, Clark.
U.S. Appl. No. 12/131,868, filed Jun. 2, 2008, Sommadossi.
U.S. Appl. No. 12/878,262, filed Sep. 9, 2010, Clark.
Interference 105,871, Notice to Declare Interference dated Feb. 22, 2012.
Interference 105,871 Sommadossi Claims dated Mar. 7, 2012.
Interference 105,871, Sommadossi Notice of Real Parties in Interest dated Mar. 7, 2012.
Interference 105,871, Sommadossi Notice of Related Proceedings dated Mar. 7, 2012.
Interference 105,871, Sommadossi File Request dated Mar. 7, 2012.
Interference 105,871, Clark Real Party-In-Interest dated Mar. 7, 2012.
Interference 105,871, Clark Claims dated Mar. 7, 2012.
Interference 105,871, Clark Request for File dated Mar. 7, 2012.
Interference 105,871, Clark Notice of Related Proceedings dated Mar. 7, 2012.
Interference 105,871, Sommadossi Motions List dated Apr. 11, 2012.
Interference 105,871, Clark List of Intended Motions dated Apr. 11, 2012.
Interference 105,871, Order Authorizing Motions dated Apr. 24, 2012.
Interference 105,871, Order Large Exhibits dated May 17, 2012.
Interference 105,871, Clark Notice dated May 31, 2012.
Interference 105,871, Sommadossi Priority Statement dated Jun. 5, 2012.
Interference 105,871, Sommadossi Substantive Motion 1 dated Jun. 5, 2012.
Interference 105,871, Sommadossi Motion 5 dated Jun. 5, 2012.
Interference 105,871, Sommadossi Exhibit List dated Jun. 5, 2012.
Interference 105,871, Clark Notice Regarding Filing Priority Satement dated Jun. 5, 2012.
Interference 105,871, Clark Priority Statement dated Jun. 5, 2012.
Interference 105,871, Clark Substantive Motion 1 dated Jun. 5, 2012.
Interference 105,871, Clark Substantive Motion 2 dated Jun. 5, 2012.
Interference 105,871, Clark Substantive Motion 3 dated Jun. 5, 2012.
Interference 105,871, Clark Substantive Motion 6 dated Jun. 5, 2012.
Interference 105,871, Order Authorizing Responsive Motion dated Jun. 18, 2012.
Interference 105,871, Notice Regarding Sommadossi Substantive Motion 5 dated Jun. 22, 2012.
Interference 105,871, Sommadossi Substantive Motion 18 dated Jun. 22, 2012.
Interference 105,871, Sommadossi Exhibit 1101 dated Jun. 28, 2012.
Interference 105,871, Sommadossi Exhibit 1136 dated Jun. 28, 2012.
Interference 105,871, Sommadossi Exhibit 1013 dated Jun. 28, 2012.
Interference 105,871, Sommadossi Exhibit 1088 dated Jun. 28, 2012.
Interference 105,871, Clark Submission of Sommadossi Declarations dated Jun. 28, 2012.
Interference 105,871, Sommadossi Submission of Clark Declarations dated Jun. 28, 2012.
Interference 105,871, Order Cross Examination of Witnesses dated Jul. 5, 2012.
Interference 105,871, Clark Notice of Change in Related Proceedings dated Jul. 6, 2012.
Interference 105,871, Order Authorizing Miscellaneous Motion dated Jul. 16, 2012.
Interference 105,871, Sommadossi Miscellaneous Motion 19 dated Jul. 18, 2012.
Interference 105,871, Clark Opposition 19 dated Jul. 25, 2012.
Interference 105,871, Sommadossi Reply 19 dated Jul. 30, 2012.
Interference 105,871, Clark Notice 2 dated Aug. 14, 2012.
Interference 105,871, Order Regarding Miscellaneous Motion and Notion Numbering dated Aug. 16, 2012.
Interference 105,871, Sommadossi Opposition 1 dated Aug. 17, 2012.
Interference 105,871, Sommadossi Opposition 2 dated Aug. 17, 2012.

(56) References Cited

OTHER PUBLICATIONS

Interference 105,871, Sommadossi Opposition 3 dated Aug. 17, 2012.
Interference 105,871, Sommadossi Opposition 6 dated Aug. 17, 2012.
Interference 105,871, Clark Opposition 1 dated Aug. 17, 2012.
Interference 105,871, Clark Opposition 6 dated Aug. 17, 2012.
Interference 105,871, Order Cross Examination of Marquez dated Sep. 27, 2012.
Interference 105,871, Sommadossi Reply 1 dated Oct. 11, 2012.
Interference 105,871, Sommadossi Reply 6 dated Oct. 11, 2012.
Interference 105,871, Clark Reply 1 dated Oct. 11, 2012.
Interference 105,871, Clark Reply 2 dated Oct. 11, 2012.
Interference 105,871, Clark Reply 3 dated Oct. 11, 2012.
Interference 105,871, Clark Reply 6 dated Oct. 11, 2012.
Interference 105,871, Clark Corrected Reply 1 dated Oct. 11, 2012.
Interference 105,871, Clark Corrected Reply 6 dated Oct. 11, 2012.
Interference 105,871, Clark Submission of Corrected Replies 1 and 6 dated Oct. 11, 2012.
Interference 105,871, Sommadossi Responses to Material Facts of Clark Corrected Reply 1 dated Oct. 18, 2012.
Interference 105,871, Sommadossi Responses to Material Facts of Clark Reply 2 dated Oct. 18, 2012.
Interferecne 105,871, Sommadossi Responses to Material Facts of Clark Reply 3 ated Oct. 18, 2012.
Interference 105,871, Sommadossi Responses to Material Facts of Clark Corrected Reply 6 dated Oct. 18, 2012.
Interference 105,871, Sommadossi Miscellaneous Motion 8 dated Oct. 23, 2012.
interference 105,871, Sommadossi Request for Oral Argument dated Oct. 23, 2012.
Interference 105,871, Clark Miscellaneous Motion 7 dated Oct. 23, 2012.
Interference 105,871, Clark Request for Oral Arguments dated Oct. 23, 2012.
Interference 105,871, Sommadossi Opposition 7 dated Nov. 13, 2012.
Interference 105,871, Clark Opposition 8 dated Nov. 13, 2012.
Interference 105,871, Order Denying Requests for Oral Argument dated Nov. 16, 2012.
Interference 105,871, Sommadossi Reply 8 dated Nov. 19, 2012.
Interference 105,871, Clark Reply 7 dated Nov. 19, 2012.
Interference 105,871, Sommadossi Filing of the Record dated Nov. 28, 2012.
Interference 105,871, Clark Final Exhibit List dated Nov. 28, 2012.
Interference 105,871, Clark Submission of Record dated Nov. 28, 2012.
Declaration of Jeffrey S. Glenn, M.D., Ph.D., signed Jun. 2, 2012.
Declaration of Stanley M. Lemon, M.D., signed Jun. 4, 2012.
Declaration of Masad J. Damha, Ph.D., signed Jun. 2, 2012.
Transcript of Deposition of Christoph Seeger, Ph.D., taken Sep. 28, 2012.
Transcript of Deposition of Victor E. Marquez, Ph.D., taken Sep. 26, 2012.
Declaration of Barry M. Trost, Ph.D., signed Jun. 20, 2012.
Transcript of Deposition of Victor E. Marquez, Ph.D., taken Jul. 27, 2012.
Transcript of Deposition of Christoph Seeger, Ph.D., taken Jul. 25, 2012.
Feb. 9, 2011 Material Transfer Agreement.
Dec. 1, 2010 Mutual Non-Disclosure Agreement.
Dec. 15, 2005 Consulting Agreement.
Declaration and Curriculum Vitae of Jean-Pierre Sommadossi, Ph.D., Interference No. 103,906, Apr. 3, 1998.
E-mail from Anthony M. Zupcic to Thomas E. Friebel on Oct. 10, 2010.
U.S. Appl. No. 60/474,368 Provisional Appln. Cover Sheet dated May 30, 2003.
U.S. Appl. No. 60/474,368, Petition to Correct Inventorship dated Jul. 11, 2005.
U.S. Appl. No. 10/608,907 Declaration and Power of Attorney filed Jan. 12, 2004.
U.S. Appl. No. 10/608,907 Amendment filed May 25, 2006.
U.S. Appl. No. 10/608,907 Amendment filed Feb. 15, 2007.
U.S. Appl. No. 10/608,907 Amendment filed Aug. 20, 2007.
U.S. Appl. No. 10/608,907 Supplemental Amendment filed Oct. 30, 2007.
U.S. Appl. No. 10/608,907 Amendment filed Jul. 24, 2008.
U.S. Appl. No. 10/608,907 Amendment filed Jan. 20, 2009.
U.S. Appl. No. 12/131,868, filed Jun. 2, 2008 (partial application per interference database for Interference No. 105871).
U.S. Appl. No. 12/131,868 Declaration and Power of Attorney filed Jun. 2, 2008.
U.S. Appl. No. 12/131,868 Preliminary Amendment filed Jun. 2, 2008.
U.S. Appl. No. 12/131,868 Response to Notice to File Corrected Application Papers dated Sep. 17, 2008.
U.S. Appl. No. 12/131,868 Response to Restriction Requirement dated Dec. 14, 2010.
U.S. Appl. No. 12/131,868 Office Action dated Mar. 3, 2011.
U.S. Appl. No. 12/131,868 Amendment dated May 27, 2011.
U.S. Appl. No. 12/131,868 Office Action dated Aug. 16, 2011.
U.S. Appl. No. 12/131,868 Amendment dated Sep. 20, 2011.
U.S. Appl. No. 12/131,868 Amendment dated Jun. 21, 2012.
U.S. Appl. No. 12/150,327 Amendment dated Nov. 16, 2010.
U.S. Appl. No. 11/005,469 Amendment dated Apr. 5, 2007.
U.S. Appl. No. 11/005,469 Amendment dated Dec. 14, 2007.
U.S. Appl. No. 11/005,444 Amendment dated Apr. 6, 2009.
U.S. Appl. No. 11/005,444 Amendment dated Apr. 4, 2008.
U.S. Appl. No. 11/005,446 Amendment dated May 7, 2007.
U.S. Appl. No. 11/854,218 Amendment dated Jun. 20, 2011.
U.S. Appl. No. 11/854,218 Office Action dated Dec. 23, 2010.
U.S. Appl. No. 11/854,218 Amendment dated Oct. 11, 2010.
U.S. Appl. No. 11/854,218 Office Action dated Jul. 22, 2010.
U.S. Appl. No. 11/854,218 Preliminary Amendment dated Sep. 12, 2007.
U.S. Appl. No. 12/878,262 Office Action dated Jun. 8, 2011.
U.S. Appl. No. 12/878,262 Preliminary Amendment dated Sep. 9, 2010.
U.S. Patent No. 7,429,572 Restriction Requirement dated Sep. 5, 2006.
U.S. Appl. No. 60/392,350, filed Jun. 28, 2002 (partial application per interference database for Interference No. 105871).
U.S. Appl. No. 60/392,350 Corrected Filing Receipt dated Jan. 17, 2008.
European Patent Appln. No. 03761744 Office Action dated Apr. 16, 2012.
Awad, Laila Fathy, et al. A Synthesis of Methyl 3-O-(β-D-Mannopyranosyl)-α-Dmannopyranoside from Sulfonate Intermediates, Bull. Chem. Soc. Jpn., vol. 59, pp. 1587-1592 (1986).
Awano et al., Arch. Pharm., 329: 66-72 (1996).
Bartenschlager and Lohmann, Antiviral Res. 52: 1-17 (2001).
Beard et al., Hepatology 30: 316-24 (1999).
Beauchamp, L.M., et al., Amino Acid Ester Prodrugs of Acyclovir, Antiviral Chemistry & Chemotherapy, vol. 3, No. 3, pp. 157-164 (1992).
Behrens et al., EMBO J. 15: 12-22 (1996).
Blight et al., Science 290: 1972-74 (2000).
Bourne, Nigel et al., Screening for Hepatitis C Virus Antiviral SctivityWith A Cell-based Secreted Alkaline Phosphatase Reporter Replicon System, Antiviral Research, vol. 67, pp. 76-82 (2005).
Briot, Anne, et al., Benzylsulfonyl: A Valuable Protecting and Decativating Group in Phenol Chemistry, Tetrahedron Letters, vol. 44, pp. 965-967 (2003).
*Calif. Inst. of Technol.* v. *Enzo Life Sciences, Inc.*, Interference 105,496, Paper 120 (BPAI Sep. 22, 2010).
Carroll and LaFemina, Antiviral Research: Strategies in Antiviral Drug Discovery 153-166 (Robert L. LaFemina, Ph.D., ed., 2009).
Choi, Yongseok et al., A Conformationally Locked Analogue of the Anti-HIV Agent Stavudine. An Important Correlation between Pseudorotation and Maximum Amplitude, J. Med. Chem., vol. 46, pp. 3292-3299 (2003).
Chu et al., FEMS Microbiology Letters 202: 9-15 (2001).

(56) References Cited

OTHER PUBLICATIONS

Clark, J.L. et al., Design, Synthesis, and Antiviral Activity of 2'-Deoxy-2'-fluoro-2'-C-methylcytidine, a Potent Inhibitor of Hepatitis C Virus Replication, J. Med. Chem., vol. 48, pp. 5504-5508 (2005).
Clark, Jeremy L., et al., Synthesis of 2-Deoxy-2-Fluoro-2-C-Methyl-DRibofuranoses, Journal of Carbohydrate Chemistry, vol. 25, pp. 461-470 (2006).
Clark, Jeremy L., et al., Synthesis and antiviral activity of 2'-deoxy-2'-fluoro-2'-Cmethyl purine nucleosides and inhibitors of hepatitis C virus RNA replication, Bioorganic & Medicinal Chemistry Letters, vol. 16, pp. 1712-1715 (2006).
Clarke, Baillière's Clin. Gastroenterol. 14: 293-305 (2000).
Cohen, Science 285: 26-30 (1999).
Commentary, Science 285: 9 (1999).
Condit, R.C., Principles of Virology (Chapter 2), in Knipe, D.M. et al., eds., Fields Virology, Fourth Edition, Philadelphia, Lippincott Williams & Wilkins (2001).
Condit, R.C., Principles of Virology (Chapter 2), in Knipe, D.M. et al., eds., Fields Virology, Fifth Edition, Philadelphia, Lippincott Williams & Wilkins (2007).
Cox et al., Principles of Biochemistry, p. 330 (1993).
Cramer and Pfleiderer, Helvetica Chimica Acta 79: 2114-2136 (1996).
Damha et al., Curr. Protocols in Nucleic Acid Chem.: 1.7.1-1.7.19 (2002).
Damha et al., Nucleosides, Nucleotides & Nucleic Acids 22: 1343-1346 (2003).
Damha et al. J. Org. Chem., 71(3): 921-925 (2006).
De Clercq, J. Clin. Virology 22: 73-89 (2001).
Désiré and Prandi, Carbohydrate Research 317: 110-118 (1999).
Dhanak, D., et al., Identification and Biological Characterization of Heterocyclic Inhibitors of the Hepatitis C Virus RNA-dependent RNA Polymerase, J. Biol. Chem. vol. 277, No. 41, pp. 38322-38327 (2002).
Diamond et al., J. Virol. 74: 4957-66 (2000).
Di Bisceglie and Bacon, Sci. Am. 281: 80-85 (1999).
Di Bisceglie, Hepatology 35:224-31 (2002).
Eldrup et al., "Stucture-Activity Relationship of Heterobase-Modified 2'-C-Methyl Ribonucleosides as Inhibitors of Hepatitis C Virus RNA Replication," J. Med. Chem., 47:5284-5297 (2004).
Ferrari et al., J. Virol. 73: 1649-54 (1999).
Fournier-Caruana et al., Biologicals 28: 33-40 (2000).
Frese et al., J. Gen. Virol. 82: 723-33 (2001).
Frese et al., Hepatology 35: 694-703 (2002).
Friebe et al., J. Virol. 75: 12047-57 (2001).
Furman et al., Antiviral Res. 91: 120-132 (2011).
*Genentech, Inc.* v. *Chiron Corp.*, Interference 105,048, Paper 258 (BPAI Nov. 30, 2004) (non-precedential).
*Goeddel* v. *Sugano* Interference 105,334, Paper 109, at 40-42 (Bpai Sep. 29, 2008), rev'd on other grounds, 617 F.3d 1350 (Fed. Cir. 2010).
Goldman, Bruce, Potential New Class of Drugs to Combat Hepatitis C Identified by Scientists, Stanford School of Medicine, http://med.stanford.edu/ism/2010/january/glenn.html (Jan. 20, 2010).
Grakoui et al., Hepatology 33: 489-95 (2001).
Greene and Wuts, Protective Groups in Organic Synthesis (3rd ed.): 76-81, 95-96, 102-106, 150, 173-176 and 197-198 (1999).
Guo, J.-T., Bichko, V.V., Seeger, C., Effect of Alpha Interferon on the Hepatitis C Virus Replicon, J. Virol., vol. 75, pp. 8516-8523 (2001).
Harrison, Steadman D., et al., Therapeutic Synergism of Tiazofurin and Selected Antitumor Drugs against Sensitive and Resistant P388 Leukemia in Mice, Cancer Research, vol. 46, pp. 3396-3400 (1986).
Harry-O'kuru, Rogers E., et al., A Short, Flexible Route toward 2'-C-Branched Ribonucleosides, J. Org. Chem., vol. 62, pp. 1754-1759 (1997).
Hirooka et al., Bull. Chem. Soc. Jpn. 74.9: 679-1694 (2001).
Hong et al., Virology 256: 36-44 (1999).

Hostetler, Karl Y., et al., Synthesis and Antiretroviral Activity of Phospholipid Analogs of Azidothymidine and Other Antiviral Nucelosides, The Journal of Biological Chemistry, vol. 265, No. 11, pp. 6112-6117 (1990).
*Hudziak* v. *Ring*, Interference 105,266, 2005 WL 3694322 (BPAI 2005).
Husson van Viiet, Biologicals 18: 25-27 (1990).
Ikeda et al., J. Virol. 76: 2997-3006 (2002 (accepted for publication Dec. 20, 2001).
Ishii et al., Hepatology 29: 1227-35 (1999).
Jeong, Lak S. et al., Unanticipated Retention of Configuration in the DAST Fluorination of Deoxy-4'-thiopyrimidine Nucleosides with "Up" Hydroxyl Groups, Tetrahedron Letters, vol. 35, No. 41, pp. 7569-7572 (1994).
Jordan et al., J. Infect. Dis. 182: 1214-17 (2000).
Julander et al., Antiviral Res. 86: 261-7 (2010).
Kim et al., Biochem. Biophys. Res. Commun. 290: 105-12 (2002).
Kolykhalov et al., Science 277: 570-74 (1997).
Krieger et al., J. Virol. 75: 4614-24 (2001).
Kuroboshi et al., Synlett 987-988 (1995).
Lal, G. Sankar, et al., Electrophilic NF Fluorinating Agents, Chem. Rev., vol. 96, pp. 1737-1755 (1996).
Lalezari, J., et al., Potent Antiviral Activity of the HCV Nucleoside Polymerase Inhibitor R7128 with PEG-IFN and Ribavirin: Interim Results of R7128 500mg BID for 28 Days, J. Hepatology, vol. 48, Supplement 2, p. S29 (2008).
Lalezari, J., et al., Potent Antiviral Activity of the HCV Nucleoside Polymerase Inhibitor, R7128, in Combination with PEG-IFN α-2a and Ribavirin, 43rd Annual Meeting of EASL, Milan, Italy, Apr. 23-27, 2008.
Lam et al., Antimicrob. Agents Chemother. 55: 2566-2575 (2011).
Lam et al., Antimicrob. Agents Chemother. 54: 3187-3196 (2010).
Lanford and Bigger, Virology 293: 1-9 (2002).
Lawitz et al., Abstract 7, J. Hepatol. 56: S4 (2012).
Lawitz et al., Abstract 102, Global Antiviral J. 5: 96.
Lesburg et al., Curr. Opin. Investig. Drugs 1: 289-96 (2000).
Leyssen et al., Clin. Microbiol. Rev. 13: 67-82 (2000).
Limbach, Patrick A., et al., Summary: The Modified Nucleosides of RNA, Nucleic Acids Research, vol. 22, No. 12, pp. 2183-2196 (1994).
Lindenbach, B.D. and Rice, C.M., Flaviviridae: The Viruses and Their Replication (Chapter 32) in Knipe, D.M. et al., eds., Fields Virology, 4th ed. Philadelphia, Lippincott Williams & Wilkins (2001).
Lohmann et al., J. Virol. 71: 8416-28 (1997).
Lohmann et al., Virology 249: 108-18 (1998).
Lohmann, V., et al., Replication of Subgenomic Hepatitis C Virus RNAs in a Hepatoma Cell Line, Science, vol. 285, pp. 110-113 (1999).
Lohmann et al. 1999, J. Biol. Chem. 274: 10807-15.
Lohmann et al., J. Virol. 75: 1437-49 (2001).
Markland et al., Antimicrob. Agents Chemother. 44: 859-66 (2000).
Marshall, Science 290: 1870-71 (2000).
Matsuda et al., Chem. Pharm. Bull. 36(3): 945-953 and 3967-3970 (1988).
McGuigan et al, Antiviral Chem. & Chemother. 12: 293-300 (2001).
McGuigan et al., Antiviral Chem. Chemother. 5: 271-277 (1994).
McKenzie, Robin, M.D., et al., Hepatic Failure and Lactic Acidosis Due to Fialuridine (FIAU), an Investigational Nucleoside Analogue for Chronic Hepatitis B, The New England Journal of Medicine, vol. 333, No. 17, pp. 1099-1105 (1995).
McManus, Appl. Environ. Microbiol. 31: 35-38 (1976).
The Merck Index, 2001, 13th ed., 4401.
W.J. Middleton, J. Org. Chem. 40(5): 574-578 (1975).
Milne, H. Bayard and Peng, Chi-Hsieh, the Use of Benzylsulfonyl Chloride in Peptide Syntheses, J. Am. Chem. Soc., vol. 79, pp. 639-644 (1956).
Moradpour et al., J. Biol. Chem. 277: 593-601 (2002).
Mottola et al., Virology 293:31-43 (2002).
Murakami et al., J. Biol. Chem. 285: 34337-34347 (2010).
Ness and Fletcher, J. Org. Chem. 22: 1470-1473 (1957).
News & Analysis, Nature Reviews 10: 891 (2011).
Oh et al., J. Virol. 73: 7694-702 (1999).

(56) References Cited

OTHER PUBLICATIONS

Oxtoby, David W., et al., Principles of Modern Chemistry, Fourth Edition, pp. A.41-A.49 (1999).
Pietschmann et al., J. Virol. 75: 1252-64 (2001).
Prusoff, Cancer Res. 23: 1246-59 (1963).
Randall and Rice, Curr. Opin. Infect. Dis. 14: 743-47 (2001).
Rosenberg, J. Mol. Biol. 313: 451-64 (2001).
Schmit, Synlett 238-240 (1994).
Shi and Lai, Cell. Mol. Life Sci. 58: 1276-95 (2001).
Shim, J. et al, Canonical 3'-deoxyribonucleotides as a chain terminator for HCV NS5B RNA-dependent RNA polymerase, Antiviral Research, vol. 58, pp. 243-251 (2003).
Shimakami et al., Proc. Nat'l. Acad. Sci U.S.A. 109:941-6 (2012).
Singh, Rajendra P. and Shreeve, Jean'ne M., Recent Advances in Nucleophilic Fluorination Reactions of Organic Compounds Using Deoxofluor and DAST, Synthesis, No. 17, pp. 2561-2678 (2002).
Sofia, Michael J., et al., Nucleoside, Nucleotide, and Non-Nucleoside Inhibitors of Hepatitis C Virus NS5B RNA-Dependent RNA-Polymerase, J. Med. Chem., vol. 55, pp. 2481-2531 (2012).
Sofia et al., J. Med. Chem. 53: 7202-7218 (2010).
Sofia et al., Abstracts of Papers, 238th ACS National Meeting, Washington, DC, United States, Aug. 16-20, 2009 MEDI-101.
Song, Xueqin, et al., Amino Acid Ester Prodrugs of the Anticancer Agent Gemcitabine: Synthesis, Bioconversion, Metabolic Bioevasion, and hPEPT1-Mediated Transport, Molecular Pharmaceutics, vol. 2, No. 2, pp. 157-167 (2004).
Sowa et al., Bulletin of the Chemical Society of Japan 487(7): 2084-2090 (1975).
Stuvyer, L.J., et al., Ribonucleoside Analogue That Blocks Replication of Bovine Viral Diarrhea and Hepatitis C Viruses in Culture, Antimicrobial Agents and Chemotherapy, vol. 47, No. 1, pp. 244-254 (2003).
Stuyver, L.J., et al., Inhibition of the Subgenomic Hepatitis C Virus Replicon in Huh-7 Cells by 2'-deoxy-2'-fluorocytidine, Antimicrobial Agents and Chemotherapy, vol. 48, No. 2, pp. 651-654 (2004).
Stuyver, L.J. et al., Inhibition of Hepatitis C Replicon RNA Synthesis by β-D-2'-Deoxy-2'-fluoro-2'-C-methylcytidine: A Specific Inhibitor of Hepatitis C Virus Replication, Antimicrobial Agents & Chemotherapy, vol. 17, pp. 79-87 (2006).
Taguchi et al., J. of the American Chemical Society 96: 3010-3011 (1974).
Taktakishvili and Nair, Tetrahedron Letters 41: 7173-7176 (2000).
The Journal of the Americal Chemical Society, Table Contents, vol. 79, No. 3 (1957).
Tisdale et al., Antivir. Chem. Chemother., 4(5): 281-7 (1993).
Trost, Barry M. and Kallander, Lara S., A Versatile Enantioselective Strategy Toward L-C-Nucleosides: A Total Synthesis of L-Showdomycin, J. Org. Chem., vol. 64, No. 15, 5427-5435 (1999).
Trost, Barry M., et al., Asymmetric Synthesis of Oxygen Heterocycles via Pd-Catalyzed Dynamic Kinetic Asymmetric Transformations: Application to Nucleosides, Chem Eur. J., vol. 9, 4442-4451 (2003).
van Boom et al., Tetrahedron Letters 27: 1211-1214 (1986).
Vithanomsat et al., Southeast Asian J. Trop. Med. Public Health 15: 27-31 (1984).
Vorbrüggen and Ruh-Pohlenz, Handbook of Nucleoside Synthesis (John Wiley & Sons., Inc., New York), pp. 140-141 and 403 (2001).
Wachtmeister et al., Tetrahedron 55: 10761-10770 (1999).
Wakita, T., et al., Production of infectious hepatitis C virus in tissue culture from a cloned viral genome, Nature Medicine, vol. 11, pp. 791-796 (2005).
Walton, E., et al., Branched-Chain Sugar Nucleosides. A New Type of Biologically Active Nucleoside, Journal of the American Chemical Society, vol. 88, No. 19, pp. 4524-4525 (1966).
Wang, Peiyuan, et al., An Efficient and Diastereoselective Synthesis of PSI-6130: A Clinically Efficacious Inhibitor of HCV NS5B Polymerase, J. Org. Chem., vol. 74, No. 17, 6819-6824 (2009).
Watts and Damha, Can. J. Chem., 86: 641-656 (2008).
Wilds and Damha, Nucleic Acids Res. 28(18): 3625-3635 (2000).
Wohlrab et al., Biochim. Biophys. Acta, 824: 233-42 (1985).
Wolfe et al., "A Concise Synthesis of 2'-C-Methylribonucleosides," Tetrahedron Letters, 36(42):7611-7614 (1995).
Wu, Hepatology 33: 1550-51 (2001).
Yamashita et al., J. Biol. Chem. 273: 15479-86 (1998).
Yanagi et al., Proc. Natl. Acad. Sci. USA 94: 8738-43 (1997).
Yanagi et al., Virology 244: 161-72 (1998).
Yang, Shu Shu, et al., Synthesis of DL-1-deoxy-fluoro-6-O-methychiro-inositol: confirmation of a structural-DAST fluorination correlation, Carbohydrate Research, vol. 249, pp. 259-263 (1993).
Yi et al., Proc. Nat'l Acad. Sci. U.S.A. 103:2310-5 (2006).
Yi, MinKyung, et al., Subgenomic Hepatitis C Virus Replicons Inducing Expression of a Secreted Enzymatic Reporter Protein, Virology, vol. 304, pp. 197-210 (2002).
Yoo et al., J. Virol. 69: 32-38 (1995).
Zuck, Paul, et al., A Cell-based β-lactamase Reporter Gene Assay for the Identification of Inhibitors of Hepatitis C Virus Replication, Analytical Biochemistry, vol. 344, pp. 344-355 (2004).
Ariza, "Current Prodrug Strategies for the Delivery of Nuleotides into Cells," Drug Design Reviews—Online, 2005, 2, 373-387.
Ballatore, et al., "Synthesis and Evaluation of Novel Amidate Prodrugs of PMEA and PMPA," Bioorganic & Medicinal Chemistry Letters 11, 2001 1053-1056.
Beltran, et al., "Rational Design of a New Series of Pronucleotide," Bioorganic & Medicinal Chemistry Letters, 11, 2001, 1775-1777.
Birkus, Cathepsin A Is the Major Hydrolase Catalyzing the Intracellular Hydrolysis of the Antiretroviral Nucleotide Phosphonoamidate Prodrugs GS-7340 and GS-9131, Antimicrobial Agents and Chemotherapy, 2007, 543-550.
Cahard, et al., "Aryloxy Phosphoramidate Triesters as Pro-Tides," Mini-Reviews in Medicinal Chemistry, 2004, 4, 371-382.
Chapman, et al., "Practical Synthesis, Separation, and Stereochemical Assignment of the PMPA Pro-Drub GS-7340," Nucleosides, Nucleotides & Nucleic Acids, 20(4-7), 621-628, 2001.
Chapman, et al., Purification of PMPA Amidate Prodrugs by SMB Chromatography and X-Ray Crystallography of the Diastereomerically Pure GS-7340, Nucleosides, Nucleotides & Nucleic Acids, 20(4-7), 1085-1090 , 2001.
Chou et al., "Phosphoramidate Pronucleotides: A Comparison of the Phosphoramidase Substrate Specificity of Human and *Escherichia coli* Histidine Triad Nucleotide Binding Proteins," Molecular Pharmaceutics, vol. 4, No. 2, 208-217, 2006.
De Clercq, Erik, "The acyclic nucleoside phosphonates from inception to clinical use: Historical perspective," Antiviral Research, 2007, 75, 1-13.
Drontle, et al., Designing a Pronucleotide Stratagem: Lessons from Amino Acid Phosphoramidates of Anticancer and Antiviral Pyrimidines, Mini-Reviews in Medicinal Chemistry, vol. 4, No. 4, 409-419, 2004.
Egron, et al., "S-Acyl-2-thioethyl Phosphoramidate Diester Derivatives as Mononucleotide Prodrugs," J. Med. Chem., 46, 4564-4571, 2003.
Egron , D.; Gosselin, G.; Bryant M.; Sommadossi J.-P.; Imbach J.-L., "Synthesis and study of antiviral S-acyl-2-thioethyl (SATE) phosphoramidate derivatives of b-L-ddA", Antiviral Research, 2001, 50 (1), A45.
Egron, et al., "Synthesis and Anti-HIV Activity of Some S-Acyl-2-Thioethyl (SATE) Phosphoramidate Derivatives of 3'-Azido-2", 3"-Dideoxythymidine," Nucleosides and Nucleotides, 18(4&5), 981-982, 1999.
Egron, "Synthesis and study of antiviral S-acyl-2-thioethyl (SATE) phosphoramidate derivatives of B-L-ddA." Submitted for 14$^{th}$ International Conference on Antiviral Research, Seattle, WA; Apr. 8-13, 2001.
Egron, et al., "Synthesis and Study of a New Series of Phosphoramidate Derivatives as Mononucleotide Prodrugs," Nucleosides, Nucleotides, 20(4-7), 751-754, 2001.
Eisenberg, et al., "Metabolism of GS-7340, A Novel Phenyl Monophosphoramidate Intracellular Prodrub of PMPA, in Blood," Nucleosides, Nucleotides 20 (4-7), 1091-1098, 2001.
Erion, et al., "Targeting thyroid hormone receptor-B agonists to the liver reduces cholesterol and triglycerides and improves the therapeutic index," PNAS, vol. 104, No. 39, 15490-15495, 2007.

(56) References Cited

OTHER PUBLICATIONS

Hecker, et al., "Prodrugs of Phosphates and Phosphonates," J. Med. Chen, 51, 2328-2345, 2008.
Hirao, et al. Partial Synthesis of Leader Sequence of Phage f1 Coat Protein mRNA, Chem Lett., 11, 1929-1932, 1986.
Huttunen, "Novel Cyclic Phosphate Prodrug Approach for Cytochrom P450-activated Drugs Containing an Alcohol Functionality," Pharmaceutical Research, vol. 24, No. 4, 679-687, 2007.
ISA/EP International Search Report dated Aug. 5, 2008 for International Application No. PCT/US2007/26408, filed Dec. 28, 2007.
ISA/EP Written Opinion of the International Searching Authority dated Aug. 5, 2008 for International Application No. PCT/US2007/26408, filed Dec. 28, 2007.
Jochum, et al., "Biolabile constructs for pronucleotide design," Journal of Organometallic Chemistry 690, 2614-2625, 2005.
Kruchkov, et al., "Influence of Solvent on the Strength of Cyclic Oxygen-Containing Phosphorus Acids," Academy of Sciences of the USSR, Division of Chemical Science, Plenum Publishing Corporation, vol. 36, No. 6, Part 1, 1145-1148, 1987.
Li, et al., "Synthesis of the Phosphoramidite Derivative of 2'-Deoxy-2'-C-B-methylcytidine," J. Org. Chem., 68, 6799-6802, 2003.
Ludwig, J., A New Route to Nucleoside 5'-triphosphates, Acta Biochim, Biophys. Acad. Sci. Hung., 16, 131-133, 1981.
Perrone, et al., "Application of the Phosphoramidate ProTide Approach to 4'-Azidouridine Confers Sub-micromolar Potency versus Hepatitis C Virus on an Inactive Nucleoside," J. Med. Chem 50, 1840-1849, 2007.
Petersen, et al., "Synthesis and Evaluation of Double-Prodrugs against HIV. Conjugation of D4T with 6-Benzyl-1-(ethoxymethyl)-5-isopropyluracil (MKC-442, Emivirine)-Type Reverse Transcriptase Inhibitors via the SATE Prodrug Approach," J. Med. Chem. 48, 1211-1220, 2005.
Peyrottes et al, "SATE pronucleotide approaches: an overview," Mini Rev. Med. Chem., 2004, 4(4), 395-408.
Placidi, et al., "Antiviral activity and intracellular metabolism of Bis(tButylSATE) phosphotriester of B-L-2',3' dideoxyadenosine, a potent inhibitor of HIV and HBV replication," Antiviral Chemistry & Chemotherapy 12:41-50, 2001.
Poijarvi-Virta, et al., "Prodrug Approaches of Nucleotides and Oligonucleotides," Current Medicinal Chemistry, 13, 3441-3467, 2006.
Prakash, et al., "Synthesis and Evaluation of S-Acyl-2-thioethyl Esters of Modified Nucleoside 5'-Monophosphates as Inhibitors of Hepatitis C Virus RNA Replication," J. Med. Chem. 48, 1199-1210, 2005.
Saboulard, D. et al., "Characterization of the Activation Pathway of Phosphoramidate Triester Prodrug of Stavudine and Zidovudine," Molecular Pharmacology, 1999, 56: 693-704.
Wagner et al, "Pronucleotides: towards in vivo delivery of antiviral and anticancer nucleotides," Med. Res. Rev., 2000, 20(6), 417-451.
Yoshimura, et al., Nucleosides and Nucleotides. 102. Stereoselective Radical Deoxygenation of *Tert*-Propargyl Alcohols in Sugar Moiety of Pyrimidine Nucleosides: Synthesis of 2'-C-Alkynyl-2'-Deoxy-1-B-D-Arabinofuranosylpyrimidines, Tetrahedron Lett., 32, 6003-6006, 1991.
Notice of Allowance dated Mar. 23, 2004 from U.S. Appl. No. 09/863,816.
Office Action dated Oct. 1, 2003 from U.S. Appl. No. 09/863,816.
Notice of Allowance dated Feb. 19, 2004 from U.S. Appl. No. 09/864,078.
Office Action dated Aug. 27, 2003 from U.S. Appl. No. 09/864,078.
Notice of Allowance dated May 17, 2006 from U.S. Appl. No. 10/602,135.
Office Action dated Apr. 5, 2005 from U.S. Appl. No. 10/602,135.
Notice of Allowance dated Mar. 9, 2006 from U.S. Appl. No. 10/602,136.
Office Action dated Dec. 10, 2008 from U.S. Appl. No. 10/602,142.
Office Action dated Feb. 26, 2008 from U.S. Appl. No. 10/602,142.
Office Action dated Jul. 28, 2006 from U.S. Appl. No. 10/602,142.
Office Action dated Mar. 29, 2007 from U.S. Appl. No. 10/602,142.
Office Action dated Nov. 15, 2005 from U.S. Appl. No. 10/602,142.
Office Action dated Sep. 20, 2007 from U.S. Appl. No. 10/602,142.
Notice of Allowance dated Jun. 15, 2009 from U.S. Appl. No. 10/602,691.
Office Action dated Oct. 7, 2008 from U.S. Appl. No. 10/602,691.
Office Action dated Feb. 26, 2008 from U.S. Appl. No. 10/602,691.
Office Action dated Aug. 22, 2007 from U.S. Appl. No. 10/602,691.
Office Action dated Dec. 29, 2006 from U.S. Appl. No. 10/602,691.
Office Action dated May 30, 2006 from U.S. Appl. No. 10/602,691.
Office Action dated Nov. 7, 2005 from U.S. Appl. No. 10/602,691.
Notice of Allowance dated Dec. 28, 2005 from U.S. Appl. No. 10/602,692.
Office Action dated Apr. 5, 2005 from U.S. Appl. No. 10/602,692.
Notice of Allowance dated Dec. 27, 2005 from U.S. Appl. No. 10/602,693.
Office Action dated Apr. 6, 2005 from U.S. Appl. No. 10/602,693.
Notice of Allowance dated Dec. 27, 2005 from U.S. Appl. No. 10/602,694.
Office Action dated Apr. 6, 2005 from U.S. Appl. No. 10/602,694.
Notice of Allowance dated Oct. 13, 2005 from U.S. Appl. No. 10/602,976.
Office Action dated May 19, 2005 from U.S. Appl. No. 10/602,976.
Office Action dated Sep. 10, 2004 from U.S. Appl. No. 10/602,976.
Notice of Allowance dated Jul. 10, 2008 from U.S. Appl. No. 10/607,909.
Office Action dated Jan. 24, 2008 from U.S. Appl. No. 10/607,909.
Office Action dated from Jun. 28, 2007 U.S. Appl. No. 10/607,909.
Notice of Allowance dated Jan. 19, 2007 from U.S. Appl. No. 10/607,909.
Notice of Allowance dated May 9, 2006 from U.S. Appl. No. 10/607,909.
Notice of Allowance dated Apr. 7, 2009 from U.S. Appl. No. 10/608,907.
Office Action dated Jan. 28, 2008 from U.S. Appl. No. 10/608,907.
Office Action dated May 31, 2007 from U.S. Appl. No. 10/608,907.
Office Action dated Aug. 15, 2006 from U.S. Appl. No. 10/608,907.
Office Action dated Nov. 26, 2008 from U.S. Appl. No. 10/608,907.
Notice of Allowance dated Apr. 7, 2009 from U.S. Appl. No. 10/609,298.
Office Action dated Aug. 2, 2006 from U.S. Appl. No. 10/609,298.
Office Action dated Aug. 24, 2007 from U.S. Appl. No. 10/609,298.
Office Action dated Jul. 10, 2008 from U.S. Appl. No. 10/609,298.
Notice of Allowance dated May 6, 2009 from U.S. Appl. No. 10/735,408.
Office Action dated Mar. 16, 2009 from the U.S. Appl. No. 10/735,408.
Office Action dated Dec. 22, 2006 from the U.S. Appl. No. 10/735,408.
Office Action dated Aug. 21, 2007 from the U.S. Appl. No. 10/735,408.
Office Action dated Jan. 9, 2008 from the U.S. Appl. No. 10/735,408.
Office Action dated Sep. 24, 2008 from the U.S. Appl. No. 10/735,408.
Office Action dated Oct. 16, 2007 from U.S. Appl. No. 11/005,440.
Office Action dated Dec. 5, 2006 from U.S. Appl. No. 11/005,440.
Office Action dated Jun. 13, 2007 from U.S. Appl. No. 11/005,440.
Office Action dated Oct. 5, 2005 from U.S. Appl. No. 11/005,440.
Notice of Allowance dated Jan. 8, 2008 from U.S. Appl. No. 11/005,441.
Notice of Allowance dated Jun. 22, 2007 from U.S. Appl. No. 11/005,441.
Office Action dated Aug. 21, 2006 from U.S. Appl. No. 11/005,441.
Office Action dated Nov. 28, 2007 from U.S. Appl. No. 11/005,442.
Office Action dated May 16, 2007 from U.S. Appl. No. 11/005,442.
Office Action dated Aug. 7, 2006 from U.S. Appl. No. 11/005,442.
Office Action dated Sep. 5, 2008 from U.S. Appl. No. 11/005,443.
Advisory Action dated Aug. 8, 2007 from U.S. Appl. No. 11/005,443.
Office Action dated Mar. 12, 2007 from U.S. Appl. No. 11/005,443.
Office Action dated Oct. 5, 2005 from U.S. Appl. No. 11/005,443.
Notice of Allowance dated Jul. 23, 2009 from U.S. Appl. No. 11/005,444.
Office Action dated Oct. 6, 2008 from U.S. Appl. No. 11/005,444.
Office Action dated Oct. 9, 2007 from U.S. Appl. No. 11/005,444.

(56) References Cited

OTHER PUBLICATIONS

Office Action dated Dec. 5, 2006 from U.S. Appl. No. 11/005,444.
Office Action dated Jun. 13, 2007 from U.S. Appl. No. 11/005,444.
Office Action dated Oct. 12, 2005 from U.S. Appl. No. 11/005,444.
Notice of Allowance dated Mar. 30, 2009 from U.S. Appl. No. 11/005,445.
Notice of Allowance dated Sep. 17, 2009 from U.S. Appl. No. 11/005,445.
Office Action dated Feb. 26, 2008 from U.S. Appl. No. 11/005,445.
Office Action dated Jul. 17, 2007 from U.S. Appl. No. 11/005,445.
Office Action dated Oct. 6, 2006 from U.S. Appl. No. 11/005,445.
Office Action dated Oct. 7, 2008 from U.S. Appl. No. 11/005,445.
Office Action dated Mar. 17, 2008 from U.S. Appl. No. 11/005,446.
Office Action dated Aug. 20, 2007 from U.S. Appl. No. 11/005,446.
Office Action dated Dec. 5, 2006 from U.S. Appl. No. 11/005,446.
Office Action dated Oct. 5, 2005 from U.S. Appl. No. 11/005,446.
Notice of Allowance dated Aug. 22, 2007 from U.S. Appl. No. 11/005,447.
Notice of Allowance dated Feb. 12, 2007 from U.S. Appl. No. 11/005,447.
Notice of Allowance dated Oct. 11, 2006 from U.S. Appl. No. 11/005,447.
Office Action dated Oct. 9, 2007 from U.S. Appl. No. 11/005,466.
Advisory Action dated Jun. 13, 2007 from U.S. Appl. No. 11/005,466.
Office Action dated Nov. 20, 2006 from U.S. Appl. No. 11/005,466.
Office Action dated Oct. 12, 2005 from U.S. Appl. No. 11/005,466.
Notice of Allowance dated Aug. 22, 2007 from U.S. Appl. No. 11/005,467.
Office Action dated Aug. 18, 2006 from U.S. Appl. No. 11/005,467.
Office Action dated Oct. 2, 2007 from U.S. Appl. No. 11/005,468.
Office Action dated Jun. 14, 2007 from U.S. Appl. No. 11/005,468.
Office Action dated Sep. 26, 2006 from U.S. Appl. No. 11/005,468.
Office Action dated Mar. 24, 2008 from U.S. Appl. No. 11/005,469.
Office Action dated Jul. 18, 2007 from U.S. Appl. No. 11/005,469.
Office Action dated Oct. 5, 2006 from U.S. Appl. No. 11/005,469.
Notice of Allowance dated Aug. 22, 2007 from U.S. Appl. No. 11/005,470.
Notice of Allowance dated Mar. 7, 2007 from U.S. Appl. No. 11/005,470.
Notice of Allowance dated Oct. 12, 2006 from U.S. Appl. No. 11/005,470.
Office Action dated Feb. 28, 2008 from U.S. Appl. No. 11/005,471.
Office Action dated Jul. 18, 2007 from U.S. Appl. No. 11/005,471.
Office Action dated Oct. 9, 2007 from U.S. Appl. No. 11/005,472.
Advisory Action dated Jun. 13, 2007 from U.S. Appl. No. 11/005,472.
Office Action dated Dec. 5, 2006 from U.S. Appl. No. 11/005,472.
Office Action dated Oct. 12, 2005 from U.S. Appl. No. 11/005,472.
Notice of Allowance dated Aug. 8, 2006 from U.S. Appl. No. 11/005,473.
Office Action dated Nov. 25, 2005 from U.S. Appl. No. 11/005,473.
Notice of Allowance dated Jun. 11, 2009 from U.S. Appl. No. 11/516,928.
Office Action dated Oct. 2, 2008 from U.S. Appl. No. 11/516,928.
Office Action dated Feb. 14, 2012 from U.S. Appl. No. 11/527,124.
Office Action dated May 26, 2011 from U.S. Appl. No. 11/527,124.
Advisory Action dated Dec. 9, 2010 from U.S. Appl. No. 11/527,124.
Office Action dated Jul. 21, 2010 from U.S. Appl. No. 11/527,124.
Office Action dated Nov. 24, 2009 from U.S. Appl. No. 11/527,124.
Notice of Allowance dated Apr. 12, 2010 from U.S. Appl. No. 11/644,304.
Office Action dated Sep. 24, 2009 from U.S. Appl. No. 11/644,304.
Notice of Allowance dated Jan. 27, 2011 from U.S. Appl. No. 12/005,937.
Office Action dated May 14, 2010 from U.S. Appl. No. 12/005,937.
Office Action dated Nov. 18, 2009 from U.S. Appl. No. 12/005,937.
De Clercq., Antiviral drugs: current state of the art, J. Clin. Virology, 22, 73-89 (2001).
Ewald et al., Nucleoside analogs: molecular mechanisms signaling cell death, Oncogene, 27, 6522-6537 (2008).
Gardelli et al., "Phosphoramidate Prodrugs of 2'-C-Methylcytidine for Therapy of Hepatitis C Virus Infection," J. Med. Chem., 52:5394-5407 (2009).
Nillroth et al., "The use of 5'-phosphate derivatives of nucleoside analogues as inhibitors of HIV-1 replication," Antiviral Chemistry & Chemotherapy, 6(1):50-64 (1995).

\* cited by examiner

US 8,680,071 B2

COMPOUNDS AND PHARMACEUTICAL COMPOSITIONS FOR THE TREATMENT OF VIRAL INFECTIONS

Priority is claimed herein to U.S. Provisional Application No. 61/320,272, entitled "Compounds and Pharmaceutical Compositions for the Treatment of Viral Infections," filed Apr. 1, 2010. The above-referenced application is incorporated by reference herein in its entirety.

FIELD

Provided herein are compounds, methods and pharmaceutical compositions, for use in treatment of viral infections, including hepatitis C virus infection in a host in need thereof. In one embodiment, phosphoramidate nucleoside compounds are provided which allow concentration of the drug in the liver.

BACKGROUND

Flaviviridae Viruses

The Flaviviridae family of viruses comprises at least three distinct genera: pestiviruses, which cause disease in cattle and pigs; flaviviruses, which are the primary cause of diseases such as dengue fever and yellow fever; and hepaciviruses, whose sole member is HCV. The flavivirus genus includes more than 68 members separated into groups on the basis of serological relatedness (Calisher et al., J. Gen. Virol, 1993, 70, 37-43). Clinical symptoms vary and include fever, encephalitis and hemorrhagic fever (Fields Virology, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include the dengue hemorrhagic fever viruses (DHF), yellow fever virus, shock syndrome and Japanese encephalitis virus (Halstead, S. B., Rev. Infect. Dis., 1984, 6, 251-264; Halstead, S. B., Science, 239:476-481, 1988; Monath, T. P., New Eng. J. Med., 1988, 319, 641-643).

The pestivirus genus includes bovine viral diarrhea virus (BVDV), classical swine fever virus (CSFV, also called hog cholera virus) and border disease virus (BDV) of sheep (Moennig, V. et al., Adv. Vir. Res. 1992, 41, 53-98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H.-J., Advances in Virus Research, 1996, 47, 53-118; Moennig V., et al, Adv. Vir. Res. 1992, 41, 53-98). Human pestiviruses have not been as extensively characterized as the animal pestiviruses. However, serological surveys indicate considerable pestivirus exposure in humans.

Pestiviruses and hepaciviruses are closely related virus groups within the Flaviviridae family. Other closely related viruses in this family include the GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are approximately 6 HCV genotypes and more than 50 subtypes. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. The genetic organization and polyprotein processing of the nonstructural protein portion of the ORF for pestiviruses and hepaciviruses is very similar. For both the pestiviruses and hepaciviruses, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya et al., (1988) Nature 333:22; Bazan and Fletterick (1989) Virology 171: 637-639; Gorbalenya et al., (1989) Nucleic Acid Res. 17.3889-3897). Similarly, the NS5B proteins of pestiviruses and hepaciviruses have the motifs characteristic of RNA-directed RNA polymerases (Koonin, E. V. and Dolja, V. V. (1993) Crit. Rev. Biochem. Molec. Biol. 28:375-430).

The actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett (1991) Virology 184:341-350; Bartenschlager et al., (1993) J. Virol. 67:3835-3844; Eckart et al., (1993) Biochem. Biophys. Res. Comm. 192:399-406; Grakoui et al., (1993) J. Virol. 67:2832-2843; Grakoui et al., (1993) Proc. Natl. Acad. Sci. USA 90:10583-10587; Hijikata et al., (1993) J. Virol. 67:4665-4675; Tome et al., (1993) J. Virol. 67:4017-4026). The NS4A protein, in both cases, acts as a cofactor with the NS3 serine protease (Bartenschlager et al., (1994) J. Virol. 68:5045-5055; Failla et al., (1994) J. Virol. 68: 3753-3760; Lin et al., (1994) 68:8147-8157; Xu et al., (1997) J. Virol. 71:5312-5322). The NS3 protein of both viruses also functions as a helicase (Kim et al., (1995) Biochem. Biophys. Res. Comm. 215: 160-166; Jin and Peterson (1995) Arch. Biochem. Biophys., 323:47-53; Warrener and Collett (1995) J. Virol. 69:1720-1726). Finally, the NS5B proteins of pestiviruses and hepaciviruses have the predicted RNA-directed RNA polymerases activity (Behrens et al. (1996) EMBO J. 15:12-22; Lehmann et al. (1997) J. Virol. 71:8416-8428; Yuan et al. (1997) Biochem. Biophys. Res. Comm. 232:231-235; Hagedorn, PCT WO 97/12033; U.S. Pat. Nos. 5,981,247; 6,248,589 and 6,461,845 Zhong et al., (1998) J. Virol. 72.9365-9369).

Hepatitis C Virus

The hepatitis C virus (HCV) is the leading cause of chronic liver disease worldwide. (Boyer, N. et al., J. Hepatol. 32:98-112, 2000). HCV causes a slow growing viral infection and is the major cause of cirrhosis and hepatocellular carcinoma (Di Besceglie, A. M. and Bacon, B. R., Scientific American, October: 80-85, (1999); Boyer, N. et al., J. Hepatol. 32:98-112, 2000). An estimated 170 million persons are infected with HCV worldwide. (Boyer, N. et al., J. Hepatol. 32:98-112, 2000). Cirrhosis caused by chronic hepatitis C infection accounts for 8,000-12,000 deaths per year in the United States, and HCV infection is the leading indication for liver transplantation.

HCV is known to cause at least 80% of posttransfusion hepatitis and a substantial proportion of sporadic acute hepatitis. Preliminary evidence also implicates HCV in many cases of "idiopathic" chronic hepatitis, "cryptogenic" cirrhosis, and probably hepatocellular carcinoma unrelated to other hepatitis viruses, such as Hepatitis B Virus (HBV). A small proportion of healthy persons appear to be chronic HCV carriers, varying with geography and other epidemiological factors. The numbers may substantially exceed those for HBV, though information is still preliminary; how many of these persons have subclinical chronic liver disease is unclear. (The Merck Manual, ch. 69, p. 901, 16th ed., (1992)).

HCV is an enveloped virus containing a positive-sense single-stranded RNA genome of approximately 9.4 kb. The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). An RNA pseudoknot structure has recently been determined to be an essential structural element of the HCV IRES. Viral structural proteins include a nucleocapsid core protein (C) and two envelope glycoproteins, E1 and E2. HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

A significant focus of current antiviral research is directed to the development of improved methods of treatment of chronic HCV infections in humans (Di Besceglie, A. M. and Bacon, B. R., *Scientific American*, October: 80-85, (1999)).

In light of the fact that HCV infection has reached epidemic levels worldwide, and has tragic effects on the infected patient, there remains a strong need to provide new effective pharmaceutical agents to treat hepatitis C that have low toxicity to the host.

Further, given the rising threat of other flaviviridae infections, there remains a strong need to provide new effective pharmaceutical agents that have low toxicity to the host.

An essential step in the mode of action of purine and pyrimidine nucleosides against viral diseases, and in particular, HCV is their metabolic activation by cellular kinases, to yield the mono-, di- and triphosphate derivatives. The biologically active species of many nucleosides is the triphosphate form, which inhibits viral DNA polymerase, RNA polymerase, or reverse transcriptase, or causes chain termination.

In light of the fact that hepatitis C virus has reached epidemic levels worldwide, and has severe and often tragic effects on the infected patient, there remains a strong need to provide new effective pharmaceutical agents to treat humans infected with the virus that have low toxicity to the host.

Therefore, there is a continuing need for effective treatments of HCV infections.

SUMMARY

Phosphoramidate compounds of a variety of therapeutic agents are provided, as well as methods for their manufacture and use in the treatment of a variety of disorders including liver disorders. Such compounds can be used in some embodiments to permit concentration of the therapeutic agent in the liver.

Phosphoramidate compounds of a variety of therapeutic agents are provided. As used herein, a "phosphoramidate compound of a therapeutic agent" includes a therapeutic agent derivatized to include a phosphoramidate group. The therapeutic agent is, for example, an anti-viral agent that includes, or has been derivatized to include, a reactive group, such as a hydroxyl, for attachment of the phosphoramidate moiety. Such therapeutic agents include, but are not limited to nucleosides and nucleoside analogs including acyclic nucleosides. In some embodiments, phosphordiamidates of nucleotides and nucleotide analogs are also provided, such as phosphordiamidates of 1', 2',3'-branched and 4'-branched nucleosides. Such compounds can be administered in an effective amount for the treatment of liver disorders, including infectious diseases, such as hepatitis C infection, including resistant strains thereof.

In certain embodiments, while not being limited to any theory, it is possible that the parent drug is obtained from selective metabolism of the phosphoramidate compound in the liver, and thus the parent drug is capable of accumulating in the liver of a host. By selectively targeting and activating compounds in the liver, potentially undesired distribution of active compound in the gastrointestinal tract can be reduced. Moreover, therapeutic amounts of active compound at the site of infection in the liver can be increased.

In certain embodiments, a 5'-monophosphate of a parent nucleoside (or nucleoside derivative) drug is formed from metabolism of the phosphoramidate compound in the liver, allowing the monophosphate to form and accumulate in the liver of a host. Thus, in certain embodiments, the phosphoramidate in effect provides a stabilized phosphate on the nucleoside or nucleoside analogue. In certain embodiments, where the compound needs to be triphosphorylated to be active, this advantageously can eliminate the requirement for the initial phosphorylation step, and promote more ready formation of the active triphosphate, which inhibits the target enzyme, and can enhance the overall activity of the nucleoside or nucleoside analog.

Without being limited to any theory, in one embodiment, a phosphoramidate of a nucleoside, such as a 2'-C-methyl-ribonucleoside, is provided that is selectively concentrated in the liver after oral administration, and metabolized in the liver cell to yield a 5'-monophosphate that can be enzymatically converted to the active form of the 5'-triphosphate, which inhibits the HCV polymerase. Thus potentially therapeutic doses can be reduced in comparison to administering the nucleoside parent molecule.

Thus, in some embodiments, after oral administration of the phosphoramidate compounds described herein, the compounds can advantageously concentrate in the liver cells at the site of infection and convert to the phosphate in the liver cell, which then is optionally further phosphorylated to implement its therapeutic effect.

Since these methods allow accumulation of phosphoramidate compounds disclosed herein in the liver of a host, the methods described herein can be useful, for example, for the treatment and/or prophylaxis of diseases or disorders of the liver, such as hepatitis C.

In certain embodiments, the compounds provided herein are useful in the prevention and treatment of Flaviviridae infections and other related conditions such as anti-Flaviviridae antibody positive and Flaviviridae-positive conditions, chronic liver inflammation caused by HCV, cirrhosis, fibrosis, acute hepatitis, fulminant hepatitis, chronic persistent hepatitis, and fatigue. These compounds or formulations can also be used prophylactically to prevent or retard the progression of clinical illness in individuals who are anti-Flaviviridae antibody or Flaviviridae-antigen positive or who have been exposed to a Flaviviridae. In one specific embodiment, the Flaviviridae is hepatitis C. In certain embodiments, the compound is used to treat any virus that replicates through an RNA-dependent RNA polymerase.

A method for the treatment of a Flaviviridae infection in a host, including a human, is also provided that includes administering an effective amount of a compound provided herein, administered either alone or in combination or alternation with another anti-Flaviviridae agent, optionally in a pharmaceutically acceptable carrier.

In certain embodiments, phosphoramidate compounds of a variety of pharmaceutical agents can be made and used therapeutically as described herein, to enhance delivery of the drug to the liver and to deliver a monophosphate of a nucleoside or an active drug containing a hydroxyl group. In one embodiment, the compound is a diphosphoramidate.

The phosphoramidate compounds, as well as salts thereof, and compositions comprising the compounds, provided herein are useful for, e.g., the treatment of disorders of the liver, such as HCV infections. In one embodiment, the compound provided herein is a compound of Formula I:

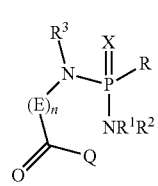

(I)

or a pharmaceutically acceptable salt, solvate, a stereoisomeric, tautomeric or polymorphic form thereof, wherein R is a moiety derivable by removal of a hydrogen from a hydroxy group of an antiviral drug, such as a nucleoside or nucleoside analog;

X is O or S;

Q is $OR^4$, $SR^4$ or $NR^5R^6$;

each E is independently $CR^7R^8$;

each n is 1 or 2;

$R^1$ and $R^2$ are selected as follows:

i) $R^1$ and $R^2$ are each independently hydrogen, alkyl, alkenyl, alkynyl, aryl, aralkyl, cycloalkyl, cycloalkenyl, alkylheterocyclyl or alkylheteroaryl;

ii) $R^1$ and $R^2$ together with the nitrogen atom on which they are substituted form a 3-7 membered heterocyclic or heteroaryl ring; or iii) $R^1$ is hydrogen, alkyl or cycloalkyl, and $R^2$ is $(G)_mC(O)Q^1$, wherein $Q^1$ is $OR^4$, $SR^4$ or $NR^5R^6$;

each G is independently $CR^7R^8$; and each m is 1 or 2;

$R^3$ and $R^4$ are each independently hydrogen, alkyl, alkenyl, alkynyl, aryl, aralkyl, cycloalkyl or cycloalkenyl;

$R^5$ and $R^6$ are selected as follows:

i) $R^5$ and $R^6$ are each independently hydrogen, alkyl, alkenyl, alkynyl, aryl, aralkyl, cycloalkyl or cycloalkenyl; or ii) $R^5$ and $R^6$ together with the nitrogen atom on which they are substituted form a 3-7 membered heterocyclic or heteroaryl ring; and $R^7$ and $R^8$ are selected as follows:

i) $R^7$ and $R^8$ are each independently hydrogen, alkyl, alkenyl, alkynyl, aryl, aralkyl, cycloalkyl, cycloalkenyl, alkylheterocyclyl or alkylheteroaryl, wherein alkyl is optionally substituted by alkoxy; or ii) $R^7$ and $R^8$ together with the carbon atom to which they are attached form a 3-7 membered cycloalkyl ring.

In one aspect, the compounds provided herein are provided or administered in combination with a second therapeutic agent, such as one useful for the treatment or prevention of HCV infections. Exemplary second therapeutic agents are provided in detail elsewhere herein.

In another aspect, provided herein are pharmaceutical compositions, single unit dosage forms, and kits suitable for use in treating or preventing disorders such as HCV infections which comprise a therapeutically or prophylactically effective amount of a compound provided herein, e.g., of Formula I, and a therapeutically or prophylactically effective amount of a second therapeutic agent such as one useful for the treatment or prevention of HCV infections.

In certain embodiments, a method of treatment of a liver disorder is provided comprising administering to an individual in need thereof a treatment effective amount of a phosphoramidate compound.

Flaviviridae which can be treated are, e.g., discussed generally in *Fields Virology*, Editors: Fields, B. N., Knipe, D. M., and Howley, P. M., Lippincott-Raven Publishers, Philadelphia, Pa., Chapter 31, 1996. In a particular embodiment of the invention, the Flaviviridae is HCV. In an alternate embodiment, the Flaviviridae is a flavivirus or pestivirus. Specific flaviviruses include, without limitation: Absettarov, Alfuy, Apoi, Aroa, Bagaza, Banzi, Bouboui, Bussuquara, Cacipacore, Carey Island, Dakar bat, Dengue 1, Dengue 2, Dengue 3, Dengue 4, Edge Hill, Entebbe bat, Gadgets Gully, Hanzalova, Hypr, Ilheus, Israel turkey meningoencephalitis, Japanese encephalitis, Jugra, Jutiapa, Kadam, Karshi, Kedougou, Kokobera, Koutango, Kumlinge, Kunjin, Kyasanur Forest disease, Langat, Louping ill, Meaban, Modoc, Montana myotis leukoencephalitis, Murray valley encephalitis, Naranjal, Negishi, Ntaya, Omsk hemorrhagic fever, Phnom-Penh bat, Powassan, Rio Bravo, Rocio, Royal Farm, Russian spring-summer encephalitis, Saboya, St. Louis encephalitis, Sal Vieja, San Perlita, Saumarez Reef, Sepik, Sokuluk, Spondweni, Stratford, Tembusu, Tyuleniy, Uganda S, Usutu, Wesselsbron, West Nile, Yaounde, Yellow fever, and Zika.

Pestiviruses which can be treated are discussed generally in *Fields Virology*, Editors: Fields, B. N., Knipe, D. M., and Howley, P. M., Lippincott-Raven Publishers, Philadelphia, Pa., Chapter 33, 1996. Specific pestiviruses include, without limitation: bovine viral diarrhea virus ("BVDV"), classical swine fever virus ("CSFV," also called hog cholera virus), and border disease virus ("BDV").

DESCRIPTION OF EXEMPLARY EMBODIMENTS

Provided herein are compounds, compositions and methods useful for treating liver disorders such as HCV infection in a subject. Further provided are dosage forms useful for such methods.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there are a plurality of definitions for a term herein, those in this section prevail unless stated otherwise.

The term "alkyl", as used herein, unless otherwise specified, refers to a saturated straight or branched hydrocarbon. In one embodiment, the alkyl group is a primary, secondary, or tertiary hydrocarbon. In one embodiment, the alkyl group includes one to ten carbon atoms, i.e., $C_1$ to $C_{10}$ alkyl. In one embodiment, the alkyl group is selected from the group consisting of methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, and 2,3-dimethylbutyl. The term includes both substituted and unsubstituted alkyl groups, including halogenated alkyl groups. In one embodiment, the alkyl group is a fluorinated alkyl group. Non-limiting examples of moieties with which the alkyl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "lower alkyl", as used herein, and unless otherwise specified, refers to a saturated straight or branched hydrocarbon having one to six carbon atoms, i.e., $C_1$ to $C_6$ alkyl. In one embodiment, the lower alkyl group is a primary, secondary, or tertiary hydrocarbon. The term includes both substituted and unsubstituted moieties.

The term "cycloalkyl", as used herein, unless otherwise specified, refers to a saturated cyclic hydrocarbon. In one embodiment, the cycloalkyl group may be a saturated, and/or bridged, and/or non-bridged, and/or a fused bicyclic group. In one embodiment, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), or from 3 to 7 ($C_{3-7}$) carbon atoms. In one embodiment, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl, or adamantyl.

The term "cycloalkenyl", as used herein, unless otherwise specified, refers to an unsaturated cyclic hydrocarbon. In one embodiment, cycloalkenyl refers to a mono- or multicyclic ring systems that respectively includes at least one double bond. In one embodiment, the cycloalkenyl group may be a bridged, non-bridged, and/or a fused bicyclic group. In one embodiment, the cycloalkyl group includes three to ten carbon atoms, i.e., $C_3$ to $C_{10}$ cycloalkyl. In some embodiments, the cycloalkenyl has from 3 to 7 ($C_{3-10}$), or from 4 to 7 ($C_{3-7}$) carbon atoms.

"Alkylene" refers to divalent saturated aliphatic hydrocarbon groups particularly having from one to eleven carbon atoms which can be straight-chained or branched. In one embodiment, the alkylene group contains 1 to 6 carbon atoms. The term includes both substituted and unsubstituted moieties. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" refers to monovalent olefinically unsaturated hydrocarbon groups, in certain embodiment, having up to about 11 carbon atoms, from 2 to 8 carbon atoms, or from 2 to 6 carbon atoms, which can be straight-chained or branched and having at least 1 or from 1 to 2 sites of olefinic unsaturation. The term includes both substituted and unsubstituted moieties. Exemplary alkenyl groups include ethenyl (i.e., vinyl, or —CH=$CH_2$), n-propenyl (—$CH_2$CH=$CH_2$), isopropenyl (—C($CH_3$)=$CH_2$), and the like.

"Alkenylene" refers to divalent olefinically unsaturated hydrocarbon groups, in certain embodiments, having up to about 11 carbon atoms or from 2 to 6 carbon atoms which can be straight-chained or branched and having at least 1 or from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically unsaturated hydrocarbon groups, in certain embodiments, having up to about 11 carbon atoms or from 2 to 6 carbon atoms which can be straight-chained or branched and having at least 1 or from 1 to 2 sites of alkynyl unsaturation. Non-limiting examples of alkynyl groups include acetylenic, ethynyl (—C≡CH), propargyl (—$CH_2$C≡CH), and the like.

The term "aryl", as used herein, and unless otherwise specified, refers to phenyl, biphenyl, or naphthyl. The term includes both substituted and unsubstituted moieties. An aryl group can be substituted with any described moiety, including, but not limited to, one or more moieties selected from the group consisting of halogen (fluoro, chloro, bromo or iodo), alkyl, haloalkyl, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991.

"Alkoxy" refers to the group —OR' where R' is alkyl or cycloalkyl. Alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

"Amino" refers to the radical —$NH_2$.

"Carboxyl" or "carboxy" refers to the radical —C(O)OH.

The term "alkylamino" or "arylamino" refers to an amino group that has one or two alkyl or aryl substituents, respectively. In one embodiment, the alkyl substituent is lower alkyl. In another embodiment, the alkyl or lower alkyl is unsubstituted.

"Halogen" or "halo" refers to chloro, bromo, fluoro or iodo.

"Monoalkylamino" refers to the group alkyl-NR'—, wherein R' is selected from hydrogen and alkyl or cycloalkyl.

"Thioalkoxy" refers to the group —SR' where R' is alkyl or cycloalkyl.

The term "heterocyclyl" or "heterocyclic" refers to a monovalent monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of the molecule through the non-aromatic ring. In certain embodiments, the heterocyclyl is a monocyclic, bicyclic, tricyclic, or tetracyclic ring system, which may include a fused or bridged ring system, and in which the nitrogen or sufur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "heteroaryl" refers to refers to a monovalent monocyclic aromatic group and/or multicyclic aromatic group that contain at least one aromatic ring, wherein at least one aromatic ring contains one or more heteroatoms independently selected from O, S, and N in the ring. Heteroaryl groups are bonded to the rest of the molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term "alkylaryl" refers to an aryl group with an alkyl substituent. The term "aralkyl" or "arylalkyl" includes an alkyl group with an aryl substituent.

The term "alkylheterocyclyl" refers to a heterocyclyl group with an alkyl substituent. The term alkylheterocyclyl includes an alkyl group with a heterocyclyl substituent.

The term "alkylheteroaryl" refers to a heteroaryl group with an alkyl substituent. The term alkylheteroaryl includes an alkyl group with a heteroaryl substituent.

The term "protecting group" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sufuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sufuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "purine" or "pyrimidine" base refers to, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-alkylaminopurine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrimidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-iodopyrimidine, $C^6$-iodo-pyrimidine, $C^5$—Br-vinyl pyrimidine, $C^6$—Br-vinyl pyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 7-deazaguanine, 7-deazaadenine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "acyl" or "O-linked ester" refers to a group of the formula C(O)R', wherein R' is alkyl or cycloalkyl (including lower alkyl), carboxylate reside of amino acid, aryl including phenyl, alkaryl, arylalkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or arylalkyl sulphonyl including methanesulfonyl, the mono, di or triphosphate ester, trityl or monomethoxytrityl, substituted benzyl, alkaryl, arylalkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclpropylacetyl, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoro-heptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term "amino acid" refers to naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In one embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

The term "substantially free of" or "substantially in the absence of" with respect to a nucleoside composition refers to a nucleoside composition that includes at least 85 or 90% by weight, in certain embodiments 95%, 98%, 99% or 100% by weight, of the designated enantiomer of that nucleoside. In one embodiment, in the methods and compounds provided herein, the compounds are substantially free of enantiomers.

Similarly, the term "isolated" with respect to a nucleoside composition refers to a nucleoside composition that includes at least 85, 90%, 95%, 98%, 99% to 100% by weight, of the nucleoside, the remainder comprising other chemical species or enantiomers.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen", the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," "alkenyl," "cycloalkenyl," "alkynyl," "aryl," "alkoxy," "alkoxycarbonyl," "amino," "carboxyl," "alkylamino," "arylamino," "thioalkyoxy," "heterocyclyl," "heteroaryl," "alkylheterocyclyl," "alkylheteroaryl," "acyl," "aralkyl," "alkaryl," "purine," "pyrimidine," "carboxyl" and "amino acid" groups optionally comprise deuterium at one or more positions where hydrogen atoms are present, and wherein the deuterium composition of the atom or atoms is other than the natural isotopic composition.

Also as used herein, "alkyl," "cycloalkyl," "alkenyl," "cycloalkenyl," "alkynyl," "aryl," "alkoxy," "alkoxycarbonyl," "carboxyl," "alkylamino," "arylamino," "thioalkyoxy," "heterocyclyl," "heteroaryl," "alkylheterocyclyl," "alkylheteroaryl," "acyl," "aralkyl," "alkaryl," "purine," "pyrimidine," "carboxyl" and "amino acid" groups optionally comprise carbon-13 at an amount other than the natural isotopic composition.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the $IC_{50}$ refers to an amount, concentration or dosage of a particular test compound that achieves a 50% inhibition of a maximal response in an assay that measures such response.

The term "host", as used herein, refers to any unicellular or multicellular organism in which the virus can replicate, including cell lines and animals, and in one embodiment, a human. Alternatively, the host can be carrying a part of the Flaviviridae viral genome, whose replication or function can be altered by the compounds of the present invention. The term host specifically includes infected cells, cells transfected with all or part of the Flaviviridae genome and animals, in particular, primates (including chimpanzees) and humans. In most animal applications of the present invention, the host is a human patient. Veterinary applications, in certain indications, however, are clearly anticipated by the present invention (such as chimpanzees).

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. In one embodiment, the subject is refractory or non-responsive to current treatments for hepatitis C infection. In another embodiment, the subject is a farm animal (e.g., a horse, a cow, a pig, etc.) or a pet (e.g., a dog or a cat). In one embodiment, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In one embodiment, a therapeutic agent is an agent which is known to be useful for, or has been or is currently being used for the treatment or prevention of a disorder or one or more symptoms thereof.

"Therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in one embodiment, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to the prevent or impede the onset, development, progression and/or severity of a disorder.

As used herein, the phrase "prophylactically effective amount" refers to the amount of a therapy (e.g., prophylactic agent) which is sufficient to result in the prevention or reduction of the development, recurrence or onset of one or more symptoms associated with a disorder (, or to enhance or improve the prophylactic effect(s) of another therapy (e.g., another prophylactic agent).

Compounds

Phosphoramidate compounds of a variety of therapeutic agents can be formed using methods available in the art and those disclosed herein. Such compounds can be used in some embodiments to enhance delivery of the drug to the liver. Therapeutic agents that can be derivatized to compound form include an anti-viral agent that includes, or has been derivatized to include a reactive group for attachment of the phosphoramidate moiety, including but not limited to nucleosides and nucleoside analogues including acyclic nucleosides. Therapeutic agents that can be derivatized to compound form also include an anti-viral agent that includes, or has been derivatized to include a phosphate group that can be derivatized to form a phosphoramidate moiety, including but not limited to nucleosides and nucleoside analogues including acyclic nucleosides.

Phosphoramidate compounds of nucleoside analogues described herein and other nucleosides known in the art can be formed as described herein and used for the treatment of liver disorders. The phosphoramidate moiety can be e.g., at the 5' position.

In one embodiment, a phosphoramidate compound provided herein is a compound of Formula I:

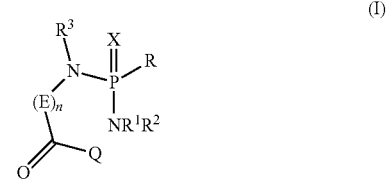

(I)

or a pharmaceutically acceptable salt, solvate, a stereoisomeric, tautomeric or polymorphic form thereof, wherein R is a moiety derivable by removal of a hydrogen from a hydroxy group of an antiviral drug, such as a nucleoside or nucleoside analog;

X is O or S;

Q is $OR^4$, $SR^4$ or $NR^5R^6$;

each E is independently $CR^7R^8$;

each n is 1 or 2;

$R^1$ and $R^2$ are selected as follows:

i) $R^1$ and $R^2$ are each independently hydrogen, alkyl, alkenyl, alkynyl, aryl, aralkyl, cycloalkyl, cycloalkenyl, alkylheterocyclyl or alkylheteroaryl;

ii) R¹ and R² together with the nitrogen atom on which they are substituted form a 3-7 membered heterocyclic or heteroaryl ring; or iii) R¹ is hydrogen, alkyl or cycloalkyl, and R² is (G)$_m$C(O)Q¹, wherein Q¹ is OR⁴, SR⁴ or NR⁵R⁶;
each G is independently CR⁷R⁸; and
each m is 1 or 2;

R³ and R⁴ are each independently hydrogen, alkyl, alkenyl, alkynyl, aryl, aralkyl, cycloalkyl or cycloalkenyl;

R⁵ and R⁶ are selected as follows:

i) R⁵ and R⁶ are each independently hydrogen, alkyl, alkenyl, alkynyl, aryl, aralkyl, cycloalkyl or cycloalkenyl; or ii) R⁵ and R⁶ together with the nitrogen atom on which they are substituted form a 3-7 membered heterocyclic or heteroaryl ring; and R⁷ and R⁸ are selected as follows:

i) R⁷ and R⁸ are each independently hydrogen, alkyl, alkenyl, alkynyl, aryl, aralkyl, cycloalkyl, cycloalkenyl, alkylheterocyclyl or alkylheteroaryl, wherein alkyl is optionally substituted by alkoxy; or ii) R⁷ and R⁸ together with the carbon atom to which they are attached form a 3-7 membered cycloalkyl ring.

The variables X, W, Y, Z, E, G, Q, Q¹, n, m, Base, R, R¹, R², R³, R⁴, R⁵, R⁶, R⁷, R⁸, R⁹, R¹⁰, R¹¹, R¹², R$^e$, R$^L$ and R$^M$, as provided herein are defined as follows. All combinations of such embodiments are within the scope of this disclosure.

In one embodiment, X is O or S. In one embodiment, X is O. In one embodiment, X is S.

In one embodiment, W is alkyl, cycloalkyl, alkenyl, cycloalkenyl or alkynyl. In one embodiment, W is alkyl. In one embodiment, W is cycloalkyl. In one embodiment, W is alkenyl. In one embodiment, W is alkynyl. In one embodiment, W is lower alkyl. In one embodiment, W is methyl. In one embodiment, W is ethynyl.

In one embodiment, Y is hydrogen or OR⁹, wherein R⁹ is as defined herein. In one embodiment, Y is hydrogen. In one embodiment, Y is OR⁹, wherein R⁹ is as defined herein. In one embodiment, Y is hydroxy.

In one embodiment, Z is hydrogen, OR¹⁰, SR¹⁰, NR⁵R⁶, F, Cl, Br or I, wherein R⁵, R⁶, and R¹⁰ are each as defined herein. In one embodiment, Z is OR¹⁰ or F, wherein R¹⁰ is as defined herein. In one embodiment, Z is hydrogen. In one embodiment, Z is OR¹¹, wherein R¹¹ is as defined herein. In one embodiment, Z is hydroxy. In one embodiment, Z is SR¹⁰, wherein R¹⁰ is as defined herein. In one embodiment, Z is NR⁵R⁶, wherein R⁵ and R⁶ are each as defined herein. In one embodiment, Z is F. In one embodiment, Z is Cl. In one embodiment, Z is Br. In one embodiment, Z is I.

In one embodiment, E is CR⁷R⁸, wherein R⁷ and R⁸ are each as defined herein.

In one embodiment, G is CR⁷R⁸, wherein R⁷ and R⁸ are each as defined herein.

In one embodiment, Q is OR⁴, SR⁴ or NR⁵R⁶, wherein R⁴, R⁵, and R⁶ are each as defined herein. In one embodiment, Q is OR⁴, wherein R⁴ is as defined herein. In one embodiment, Q is OCH₃, OCH₂CH₃, OCH₂CH₂CH₃, OCH(CH₃)₂, or OCH₂CH₂CH₃. In one embodiment, Q is SR⁴, wherein R⁴ is as defined herein. In one embodiment, Q is NR⁵R⁶, wherein R⁵ and R⁶ are each as defined herein.

In one embodiment, Q¹ is OR⁴, SR⁴ or NR⁵R⁶, wherein R⁴, R⁵, and R⁶ are each as defined herein. In one embodiment, Q¹ is OR⁴, wherein R⁴ is as defined herein. In one embodiment, Q¹ is OCH₃, OCH₂CH₃, OCH₂CH₂CH₃, OCH(CH₃)₂, or OCH₂CH₂CH₃. In one embodiment, Q¹ is SR⁴, wherein R⁴ is as defined herein. In one embodiment, Q¹ is NR⁵R⁶, wherein R⁵ and R⁶ are each as defined herein.

In one embodiment, n is 1 or 2. In one embodiment, n is 1. In one embodiment, n is 2.

In one embodiment, m is 1 or 2. In one embodiment, m is 1. In one embodiment, m is 2.

In one embodiment, Base is a substituted or unsubstituted purine or pyrimidine. In one embodiment, Base is a substituted or unsubstituted purine. In one embodiment, Base is a substituted or unsubstituted pyrimidine. In one embodiment, Base is selected from the group consisting of adenine, N⁶-alkylpurines, N⁶-acylpurines (wherein acyl is C(O)(alkyl, aryl, alkylaryl, or arylalkyl), N⁶-benzylpurine, N⁶-halopurine, N⁶-vinylpurine, N⁶-acetylenic purine, N⁶-acyl purine, N⁶-hydroxyalkyl purine, N⁶-alkylaminopurine, N⁶-thioalkyl purine, N²-alkylpurines, N²-alkyl-6-thiopurines, thymine, cytosine, 5-fluorocytosine, 5-methylcytosine, 6-azapyrimidine, including 6-azacytosine, 2- and/or 4-mercaptopyrimidine, uracil, 5-halouracil, including 5-fluorouracil, C⁵-alkylpyrimidines, C⁵-benzylpyrimidines, C⁵-halopyrimidines, C⁵-vinylpyrimidine, C⁵-acetylenic pyrimidine, C⁵-acyl pyrimidine, C⁵-hydroxyalkyl purine, C⁵-amidopyrimidine, C⁵-cyanopyrimidine, C⁵-iodopyrimidine, C⁶-iodo-pyrimidine, C⁵—Br-vinyl pyrimidine, C⁶—Br-vinyl pyrimidine, C⁵-nitropyrimidine, C⁵-amino-pyrimidine, N²-alkylpurines, N²-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 7-deazaguanine, 7-deazaadenine, 2,6-diaminopurine, and 6-chloropurine.

In one embodiment, Base is adenine, cytosine, guanine, hypoxanthine, thymine or uridine. In one embodiment, Base is cytosine. In one embodiment, Base is guanine. In one embodiment, Base is uridine.

In another embodiment, Base is selected from one of formulae (i) to (xv):

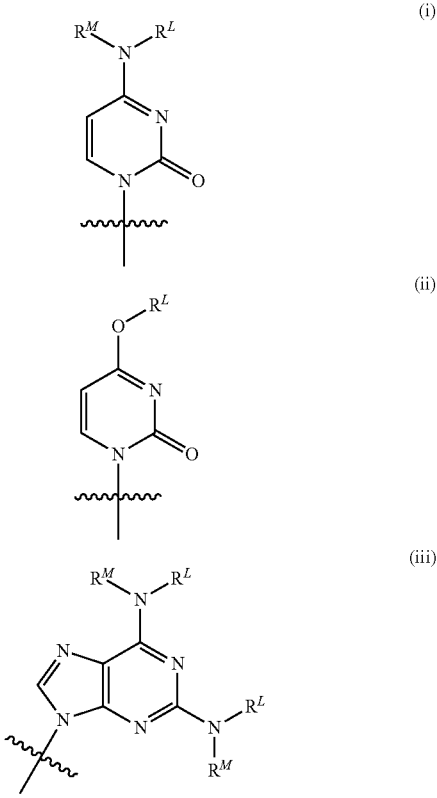

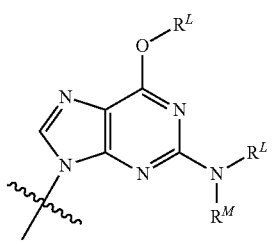 (iv)
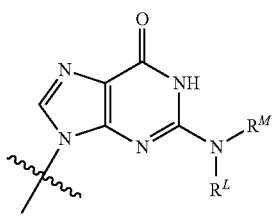 (v)
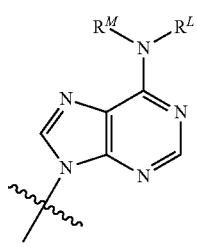 (vi)
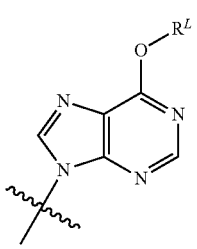 (vii)
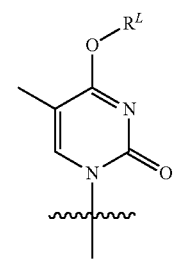 (viii)
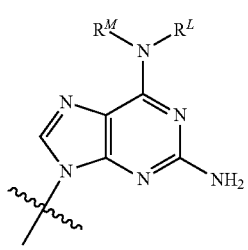 (ix)
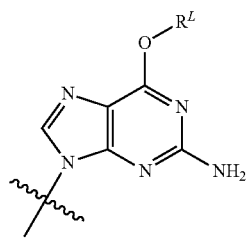 (x)
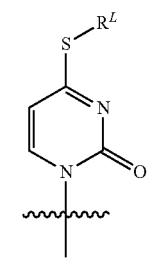 (xi)
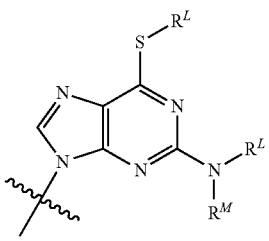 (xii)
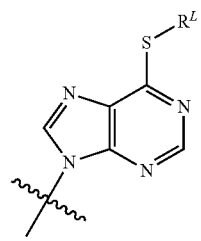 (xiii)
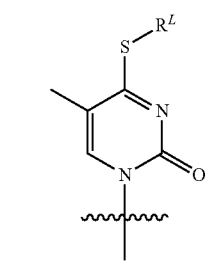 (xiv)
(xv)
wherein $R^L$ and $R^M$ are each as defined herein.
In one embodiment, R is a moiety derivable by removal of a hydrogen from a hydroxy group of an antiviral drug. In one embodiment, R is a moiety derivable by removal of a hydrogen from a hydroxy group of a nucleoside or nucleoside analog. In one embodiment, R is derived from a nucleoside comprising a cyclic or acyclic sugar or an analog thereof.

In one embodiment, R is a moiety derivable by removal of a hydrogen from a hydroxy group of an anti-viral nucleoside analog useful for treatment of HCV virus infection selected from ribavirin, viramidine, 2'-C-methylcytidine, 2'-C-methylguanosine, valopicitabine (NM 283), MK-0608, 7-Fluoro-MK-0608, PSI-6130, PSI-6206, PSI-35938 and R1479. In one embodiment, R is derived from ribavirin, viramidine, 2'-C-methylcytidine, 2'-C-methylguanosine, PSI-6130, PSI-6206, PSI-35938 or R1479. In one embodiment, R is derived from ribavirin. In one embodiment, R is derived from 2'-C-methylcytidine. In one embodiment, R is derived from 2'-C-methylguanosine. In one embodiment, R is derived from PSI-6130. In one embodiment, R is derived from PSI-6206. In one embodiment, R is derived from PSI-35938. In one embodiment, R is derived from R1479.

In one embodiment, $R^1$ is hydrogen, alkyl, alkenyl, alkynyl, aryl, aralkyl, cycloalkyl, cycloalkenyl, alkylheterocyclyl or alkylheteroaryl. In one embodiment, $R^1$ is hydrogen, alkyl or cycloalkyl. In one embodiment, $R^1$ is hydrogen. In one embodiment, $R^1$ is alkyl. In one embodiment, $R^1$ is lower alkyl. In one embodiment, $R^1$ is isopropyl. In one embodiment, $R^1$ is aralkyl.

In one embodiment, $R^2$ is hydrogen, alkyl, alkenyl, alkynyl, aryl, aralkyl, cycloalkyl, cycloalkenyl, alkylheterocyclyl or alkylheteroaryl. In one embodiment, $R^2$ is hydrogen, alkyl or cycloalkyl. In one embodiment, $R^2$ is hydrogen. In one embodiment, $R^2$ is alkyl. In one embodiment, $R^2$ is lower alkyl. In one embodiment, $R^2$ is aralkyl. In one embodiment, $R^2$ is $(G)_mC(O)Q^1$, wherein G, $Q^1$, and m are each as defined herein.

In one embodiment, $R^1$ and $R^2$ together with the nitrogen atom on which they are attached form a 3-7 membered heterocyclic or heteroaryl ring. In one embodiment, $R^1$ and $R^2$ together with the nitrogen atom on which they are attached form a 3-7 membered heterocyclic ring.

In one embodiment, $R^1$ is hydrogen, alkyl or cycloalkyl, and $R^2$ is $(G)_mC(O)Q^1$, wherein G, $Q^1$, and m are each as defined herein. In one embodiment, $R^1$ is hydrogen or lower alkyl and $R^2$ is $(G)_mC(O)Q^1$, wherein G, $Q^1$, and m are each as defined herein. In one embodiment, $R^1$ is hydrogen and $R^2$ is $(G)_mC(O)Q^1$, wherein G, $Q^1$, and m are each as defined herein.

In one embodiment, $R^3$ is hydrogen, alkyl, alkenyl, alkynyl, aryl, aralkyl, cycloalkyl or cycloalkenyl. In one embodiment, $R^3$ is hydrogen, alkyl or cycloalkyl. In one embodiment, $R^3$ is hydrogen or alkyl. In one embodiment, $R^3$ is hydrogen.

In one embodiment, $R^4$ is hydrogen, alkyl, alkenyl, alkynyl, aryl, aralkyl, cycloalkyl or cycloalkenyl. In one embodiment, $R^4$ is hydrogen, alkyl, aryl, aralkyl or cycloalkyl. In one embodiment, $R^4$ is hydrogen or alkyl. In one embodiment, $R^4$ is $C_1$-$C_6$ alkyl. In one embodiment, $R^4$ is $C_1$-$C_4$ alkyl. In one embodiment, $R^4$ is $C_1$-$C_3$ alkyl. In one embodiment, $R^4$ is phenyl. In one embodiment, $R^4$ is benzyl. In one embodiment, $R^4$ is methyl, ethyl, propyl, isopropyl, or butyl. In one embodiment, $R^4$ is hydrogen.

In one embodiment, $R^5$ is hydrogen, alkyl, alkenyl, alkynyl, aryl, aralkyl, cycloalkyl or cycloalkenyl. In one embodiment, $R^5$ is hydrogen, alkyl or cycloalkyl. In one embodiment, $R^5$ is hydrogen. In one embodiment, $R^5$ is alkyl. In one embodiment, $R^5$ is lower alkyl.

In one embodiment, $R^6$ is hydrogen, alkyl, alkenyl, alkynyl, aryl, aralkyl, cycloalkyl or cycloalkenyl. In one embodiment, $R^6$ is hydrogen, alkyl or cycloalkyl. In one embodiment, $R^6$ is hydrogen. In one embodiment, $R^6$ is alkyl. In one embodiment, $R^6$ is lower alkyl.

In one embodiment, $R^5$ and $R^6$ together with the nitrogen atom on which they are attached form a 3-7 membered heterocyclic or heteroaryl ring. In one embodiment, $R^5$ and $R^6$ together with the nitrogen atom on which they are attached form a 3-7 membered heterocyclic ring.

In one embodiment, $R^7$ is hydrogen, alkyl, alkenyl, alkynyl, aryl, aralkyl, cycloalkyl, cycloalkenyl, alkylheterocyclyl or alkylheteroaryl, wherein alkyl is optionally substituted by alkoxy. In one embodiment, $R^7$ is $C_2$-$C_6$ alkyl. In one embodiment, $R^7$ is $C_3$-$C_6$ alkyl. In one embodiment, $R^7$ is $C_4$-$C_6$ alkyl. In one embodiment, $R^7$ is hydrogen, $C_2$-$C_{10}$ alkyl, alkenyl, alkynyl, aryl, aralkyl, cycloalkyl, cycloalkenyl, alkylheterocyclyl or alkylheteroaryl, wherein alkyl is optionally substituted by alkoxy. In one embodiment, $R^7$ is hydrogen. In one embodiment, $R^7$ is alkyl. In one embodiment, $R^7$ is lower alkyl. In one embodiment, $R^7$ is methyl.

In one embodiment, $R^8$ is hydrogen, alkyl, alkenyl, alkynyl, aryl, aralkyl, cycloalkyl, cycloalkenyl, alkylheterocyclyl or alkylheteroaryl, wherein alkyl is optionally substituted by alkoxy. In one embodiment, $R^8$ is hydrogen, $C_2$-$C_{10}$ alkyl, alkenyl, alkynyl, aryl, aralkyl, cycloalkyl, cycloalkenyl, alkylheterocyclyl or alkylheteroaryl, wherein alkyl is optionally substituted by alkoxy. In one embodiment, $R^8$ is hydrogen, alkyl or cycloalkyl. In one embodiment, $R^8$ is hydrogen. In one embodiment, $R^8$ is alkyl. In one embodiment, $R^8$ is lower alkyl. In one embodiment, $R^8$ is $C_1$-$C_6$ alkyl. In one embodiment, $R^8$ is $C_1$-$C_4$ alkyl. In one embodiment, $R^8$ is $C_2$-$C_{10}$ alkyl. In one embodiment, $R^8$ is $C_2$-$C_6$ alkyl. In one embodiment, $R^8$ is $C_3$-$C_6$ alkyl. In one embodiment, $R^8$ is $C_4$-$C_6$ alkyl. In one embodiment, $R^8$ is methyl. In one embodiment, $R^8$ is isobutyl. In one embodiment, $R^8$ is sec-butyl. In one embodiment, $R^8$ is aryl. In one embodiment, $R^8$ is phenyl. In one embodiment, $R^8$ is aralkyl. In one embodiment, $R^8$ is benzyl. In one embodiment, $R^8$ is alkylheteroaryl. In one embodiment, $R^8$ is 1-H-indol-3-ylmethyl. In one embodiment, $R^8$ is alkyl is optionally substituted by alkoxy. In one embodiment, $R^8$ is t-butoxymethyl.

In one embodiment, $R^7$ and $R^8$ together with the carbon atom to which they are attached form a 3-7 membered cycloalkyl or heterocyclic ring. In one embodiment, $R^7$ and $R^8$ together with the carbon atom to which they are attached form a 5-membered cycloalkyl or heterocyclic ring. In one embodiment, $R^7$ and $R^7$ together with the carbon atom to which they are attached form cyclopentyl.

In one embodiment, $R^9$ is hydrogen, alkyl, alkenyl, alkynyl, aryl, aralkyl, cycloalkyl or cycloalkenyl. In one embodiment, $R^9$ is hydrogen, alkyl or cycloalkyl. In one embodiment, $R^9$ is hydrogen or lower alkyl. In one embodiment, $R^9$ is hydrogen.

In one embodiment, $R^{10}$ is hydrogen, alkyl, alkenyl, alkynyl, aryl, aralkyl, cycloalkyl or cycloalkenyl. In one embodiment, $R^{10}$ is hydrogen, alkyl or cycloalkyl. In one embodiment, $R^{10}$ is hydrogen or lower alkyl. In one embodiment, $R^{10}$ is hydrogen.

In one embodiment, $R^9$ and $R^{10}$ together with C(O) and the oxygen or sufur atoms on which they are attached form a 5 membered heterocyclic ring.

In one embodiment, $R^{11}$ and $R^{12}$ are each independently hydrogen, hydroxy, alkoxy, amino, alkylamino, dialkylamino, thioalkyl, F, Cl, Br, or I. In one embodiment, $R^{11}$ is hydrogen. In one embodiment, $R^{11}$ is hydroxy. In one embodiment, $R^{11}$ is alkoxy. In one embodiment, $R^{11}$ is alkylamino or dialkylamino. In one embodiment, $R^{11}$ is thioalkyl. In one embodiment, $R^{11}$ is F. In one embodiment, $R^{11}$ is Cl. In one embodiment, $R^{11}$ is Br. In one embodiment, $R^{11}$ is I.

In one embodiment, $R^{12}$ is hydrogen. In one embodiment, $R^{12}$ is hydroxy. In one embodiment, $R^{12}$ is alkoxy. In one embodiment, $R^{12}$ is alkylamino or dialkylamino. In one embodiment, $R^{12}$ is thioalkyl. In one embodiment, $R^{12}$ is F. In one embodiment, $R^{12}$ is Cl. In one embodiment, $R^{12}$ is Br. In one embodiment, $R^{12}$ is I.

In one embodiment, $R^e$ is hydrogen, alkyl or cycloalkyl. In one embodiment, $R^e$ is hydrogen. In one embodiment, $R^e$ is methyl, ethyl or propyl. In one embodiment, $R^e$ is methyl. In one embodiment, $R^e$ is ethyl. In one embodiment, $R^e$ is propyl.

In one embodiment, $R^L$ is hydrogen, alkyl, cycloalkyl, acyl, carbamyl, CO-alkyl, CO-aryl, CO-alkoxyalkyl, CO-aryloxyalkyl, CO-substituted aryl, sulfonate ester, alkyl sulfonyl, aryl sulfonyl, arylalkyl sulfonyl, a lipid, a phospholipid, an amino acid or a carbohydrate. In one embodiment, $R^L$ is alkyl or cycloalkyl. In one embodiment, $R^L$ is methyl, ethyl, propyl or isopropyl. In one embodiment, $R^L$ is methyl. In one embodiment, $R^L$ is cyclopropyl or cyclopentyl. In one embodiment, $R^L$ is hydrogen.

In one embodiment, $R^M$ is hydrogen, alkyl, cycloalkyl, acyl, carbamyl, CO-alkyl, CO-aryl, CO-alkoxyalkyl, CO-aryloxyalkyl, CO-substituted aryl, sulfonate ester, alkyl sulfonyl, aryl sulfonyl, arylalkyl sulfonyl, a lipid, a phospholipid, an amino acid or a carbohydrate. In one embodiment, $R^M$ is alkyl or cycloalkyl. In one embodiment, $R^M$ is methyl, ethyl, propyl or isopropyl. In one embodiment, $R^M$ is methyl. In one embodiment, $R^L$ is cyclopropyl or cyclopentyl. In one embodiment, $R^M$ is hydrogen.

In one embodiment, $R^L$ and $R^M$ together with the N atom to which they are attached from heterocyclyl. In one embodiment, $R^L$ and $R^M$ together with the N atom to which they are attached from 3-7 membered heterocyclyl. In one embodiment, $R^L$ and $R^M$ together with the N atom to which they are attached from 5-membered heterocyclyl. In one embodiment, $R^L$ and $R^M$ together with the N atom to which they are attached from pyrrolidinyl. In one embodiment, $R^L$ and $R^M$ together with the N atom to which they are attached from 6-membered heterocyclyl. In one embodiment, $R^L$ and $R^M$ together with the N atom to which they are attached from morpholinyl.

In one embodiment, $R^7$ and $R^8$ are selected as follows:
i) $R^7$ and $R^8$ are each independently hydrogen, $C_2$-$C_{10}$ alkyl, alkenyl, alkynyl, aryl, aralkyl, cycloalkyl, cycloalkenyl, alkylheterocyclyl or alkylheteroaryl, wherein alkyl is optionally substituted by alkoxy; or
ii) $R^7$ and $R^8$ together with the carbon atom to which they are attached form a 3-7 membered cycloalkyl ring.

In another embodiment, one of $R^7$ or $R^8$ is independently hydrogen or $C_2$-$C_6$ alkyl.
In another embodiment, one of $R^7$ or $R^8$ is $C_2$-$C_6$ alkyl.
In another embodiment, one of $R^7$ or $R^8$ is $C_3$-$C_6$ alkyl.
In another embodiment, one of $R^7$ or $R^8$ is $C_4$-$C_6$ alkyl.
In one embodiment, one of $R^7$ or $R^8$ is not $C_1$-$C_3$ alkyl.
In one embodiment, one of $R^7$ or $R^8$ is not methyl.
In one embodiment, $R^7$ or $R^8$ are each methyl.
In another embodiment, one of $R^7$ or $R^8$ is isobutyl.
In another embodiment, one of $R^7$ or $R^8$ is sec-butyl.
In another embodiment, one of $R^7$ or $R^8$ is $C_{6-10}$ aryl.
In another embodiment, one of $R^7$ or $R^8$ is phenyl.
In another embodiment, one of $R^7$ or $R^8$ is $C_{7-10}$ aralkyl.
In another embodiment, one of $R^7$ or $R^8$ is benzyl.
In another embodiment, one of $R^7$ or $R^8$ is substituted heteroaryl.
In another embodiment, one of $R^7$ or $R^8$ is 1-H-indol-3-ylmethyl.
In another embodiment, one of $R^7$ or $R^8$ is substituted alkyl.
In another embodiment, one of $R^7$ or $R^8$ is t-butoxymethyl.

In another embodiment, the compound is of Formula I, wherein
$R^1$ and $R^3$ are each hydrogen;
$R^2$ is $(G)_m C(O)Q^1$; and
m is 1.

In another embodiment, the compound is of Formula I, wherein
$R^1$ and $R^3$ are each hydrogen;
$R^2$ is $(G)_m C(O)Q^1$; and
m is 2.

In another embodiment, the compound is of Formula I, wherein
$R^1$ and $R^3$ are each hydrogen;
$R^2$ is $(G)_m C(O)Q^1$;
m is 1;
$Q^1$ is $OR^4$; and
$R^4$ is alkyl.

In another embodiment, the compound is of Formula I, wherein
$R^1$ and $R^3$ are each hydrogen;
$R^2$ is $(G)_m C(O)Q^1$;
m is 1;
$Q^1$ is $OR^4$; and
$R^4$ is alkyl.
each $R^7$ is hydrogen; and
each $R^9$ is alkyl, alkylaryl or alkylheteroaryl.

In one embodiment, X is O.
In another embodiment, $Q^1$ is $OR^4$ and $R^4$ is alkyl.
In another embodiment, $Q^2$ is $OR^4$ and $R^4$ is alkyl.
In another embodiment, $R^4$ is methyl or ethyl.
In another embodiment, $R^1$ and $R^2$ together with the nitrogen atom on which they are substituted form a 3-7 membered heterocyclic ring.

In some embodiments, when the phosphoramidate is substituted with at least one amino acid group, the amino acid is in the L-configuration.

In some embodiments, provided herein are:
(a) compounds as described herein, e.g., of Formula I, and pharmaceutically acceptable salts and compositions thereof;
(b) compounds as described herein, e.g., of Formula I, and pharmaceutically acceptable salts and compositions thereof for use in the treatment and/or prophylaxis of a liver disorder including Flaviviridae infection, especially in individuals diagnosed as having a Flaviviridae infection or being at risk of becoming infected by hepatitis C;
(c) processes for the preparation of compounds as described herein, e.g., of Formula I, as described in more detail elsewhere herein;
(d) pharmaceutical formulations comprising a compound as described herein, e.g., of Formula I, or a pharmaceutically acceptable salt thereof together with a pharmaceutically acceptable carrier or diluent;
(e) pharmaceutical formulations comprising a compound as described herein, e.g., of Formula I, or a pharmaceutically acceptable salt thereof together with one or more other effective anti-HCV agents, optionally in a pharmaceutically acceptable carrier or diluent;
(f) a method for the treatment and/or prophylaxis of a host infected with Flaviviridae that includes the administration of an effective amount of a compound as described herein, e.g., of Formula I, its pharmaceutically acceptable salt or composition; or
(g) a method for the treatment and/or prophylaxis of a host infected with Flaviviridae that includes the administration of an effective amount of a compounds as described herein, e.g., of Formula I, its pharmaceutically acceptable salt or composition in combination and/or alternation with one or more effective anti-HCV agent.

Those of skill in the art will recognize that compounds provided herein may be designed or prepared by reaction, e.g., at a hydroxy group of said anti-viral drug, for example, via condensation or dehydration. For convenience, in the description herein when substituents, such as exemplary R groups are identified as a drug, those of skill in the art will recognize that the compound, e.g., of Formula I, comprises a derivative, e.g., a radical of the anti-viral drug. Those derivatives can for example be prepared by elimination of a hydrogen radical from a hydroxy group of the drug, for instance in a dehydration reaction. Where appropriate, certain derivatives can be prepared by modification of a phosphate of an anti-viral drug to yield a compound provided herein.

In certain embodiments, R is a moiety derivable by removal of a hydrogen from a hydroxy group of a nucleoside comprising a cyclic or acyclic sugar or an analog thereof, including any nucleoside or analogue thereof described herein or known in the art.

In certain embodiments, R is a moiety derivable by removal of a hydrogen from a hydroxy group of an anti-viral nucleoside analog useful for treatment of HCV virus infection selected from ribavirin, viramidine, 2'-C-methylcytidine, 2'-C-methylguanosine, valopicitabine (NM 283), MK-0608, 7-Fluoro-MK-0608, PSI-6130, PSI-6206, PSI-35938 and R1479.

In one embodiment, the compound provided herein is a compound of Formula II:

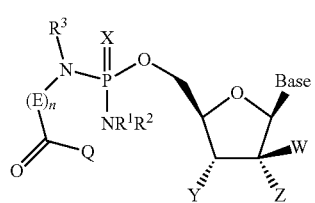

(II)

or a pharmaceutically acceptable salt, solvate, a stereoisomeric, tautomeric or polymorphic form thereof, wherein Base is a substituted or unsubstituted purine or pyrimidine;
W is alkyl, cycloalkyl, alkenyl, cycloalkenyl or alkynyl;
X is O or S;
Y is hydrogen or $OR^9$;
Z is hydrogen, $OR^{10}$, $SR^{10}$, $NR^5R^6$, F, Cl, Br or I;
Q is $OR^4$, $SR^4$ or $NR^5R^6$;
each E is independently $CR^7R^8$;
each n is 1 or 2;
$R^1$ and $R^2$ are selected as follows:
  i) $R^1$ and $R^2$ are each independently hydrogen, alkyl, alkenyl, alkynyl, aryl, aralkyl, cycloalkyl, cycloalkenyl, alkylheterocyclyl or alkylheteroaryl;
  ii) $R^1$ and $R^2$ together with the nitrogen atom on which they are substituted form a 3-7 membered heterocyclic or heteroaryl ring; or
  iii) $R^1$ is hydrogen, alkyl or cycloalkyl, and $R^2$ is $(G)_mC(O)Q^1$, wherein
    $Q^1$ is $OR^4$, $SR^4$ or $NR^5R^6$;
    each G is independently $CR^7R^8$; and
    each m is 1 or 2;
$R^3$ and $R^4$ are each independently hydrogen, alkyl, alkenyl, alkynyl, aryl, aralkyl, cycloalkyl or cycloalkenyl;

$R^5$ and $R^6$ are selected as follows:
  i) $R^5$ and $R^6$ are each independently hydrogen, alkyl, alkenyl, alkynyl, aryl, aralkyl, cycloalkyl or cycloalkenyl; or
  ii) $R^5$ and $R^6$ together with the nitrogen atom on which they are substituted form a 3-7 membered heterocyclic or heteroaryl ring;
$R^7$ and $R^8$ are selected as follows:
  i) $R^7$ and $R^8$ are each independently hydrogen, alkyl, alkenyl, alkynyl, aryl, aralkyl, cycloalkyl, cycloalkenyl, alkylheterocyclyl or alkylheteroaryl, wherein alkyl is optionally substituted by alkoxy; or
  ii) $R^7$ and $R^8$ together with the carbon atom to which they are attached form a 3-7 membered cycloalkyl ring;
$R^9$ and $R^{10}$ are selected as follows:
  i) $R^9$ and $R^{10}$ are each independently hydrogen, alkyl, alkenyl, alkynyl, aryl, aralkyl, cycloalkyl or cycloalkenyl; or
  ii) $R^9$ and $R^{10}$ together with C(O) and the oxygen or sufur atoms on which they are substituted form a 5 membered ring.

In one embodiment, if $R^2$ is $(G)_mC(O)Q^1$, G is $CR^7R^8$, m is 1, and one of $R^7$ and $R^8$ is hydrogen, the other of $R^7$ and $R^8$ is not methyl.

In one embodiment, Y is $OR^9$ and Z is $OR^{10}$ or F.

In one embodiment, W is alkyl, alkenyl or alkynyl.

In one embodiment, W is alkyl.

In one embodiment, W is ethynyl; Y is $OR^9$; Z is F; and $R^9$ is hydrogen.

In one embodiment, W is methyl; Y is $OR^9$; Z is F; and $R^9$ is hydrogen

In one embodiment, W is methyl; Y is $OR^9$; Z is $OR^{10}$; and $R^9$ and $R^{10}$ are each hydrogen.

In one embodiment, Base is substituted or unsubstituted purine; W is methyl; Y is $OR^9$; Z is $OR^{10}$; and $R^9$ and $R^{10}$ are each hydrogen.

In one embodiment, Base is substituted or unsubstituted guanine; W is methyl; Y is $OR^9$; Z is $OR^{10}$; and $R^9$ and $R^{10}$ are each hydrogen.

In one embodiment, Q and $Q^1$ are each $OR^4$ and each $R^4$ is alkyl.

In one embodiment, X is O.

In one embodiment, $R^1$ and $R^3$ are each hydrogen; $R^2$ is $(G)_mC(O)Q^1$; and m is 1.

In one embodiment, $R^1$ and $R^3$ are each hydrogen; $R^2$ is $(G)_mC(O)Q^1$; and m is 2.

In one embodiment, $R^1$ and $R^3$ are each hydrogen; $R^2$ is $(G)_mC(O)Q^1$; n is 1; and m is 1.

In one embodiment, $R^1$ and $R^3$ are each hydrogen; $R^2$ is $(G)_mC(O)Q^1$; n is 2; and m is 2.

In one embodiment, $R^1$ and $R^3$ are each hydrogen; $R^2$ is $(G)_mC(O)Q^1$; n is 1; m is 1; $Q^1$ is $OR^4$; and $R^4$ is alkyl.

In one embodiment, $R^1$ and $R^3$ are each hydrogen; $R^2$ is $(G)_mC(O)Q^1$; n is 2; m is 2; $Q^1$ is $OR^4$; and $R^4$ is alkyl.

In one embodiment, $R^1$ and $R^3$ are each hydrogen; $R^2$ is $(G)_mC(O)Q^1$; n is 1;

m is 1;
each $R^7$ is hydrogen; and
each $R^8$ is $C_{2-10}$ alkyl.

In one embodiment, $R^1$ and $R^3$ are each hydrogen;
$R^2$ is $(G)_mC(O)Q^1$;
n is 1;
m is 1;
each $R^7$ is hydrogen;
each $R^8$ is $C_{2-10}$ alkyl; and
Q and $Q^1$ are each $SR^4$.

In one embodiment, $R^1$ and $R^3$ are each hydrogen;
$R^2$ is $(G)_mC(O)Q^1$;
n is 1;
m is 1;
each $R^7$ is hydrogen;
each $R^8$ is $C_{2-10}$ alkyl; and
Q and $Q^1$ are each $NR^5R^6$.

In one embodiment, $R^1$ and $R^3$ are each hydrogen;
$R^2$ is $(G)_mC(O)Q^1$;
n is 1;
m is 1;
each $R^7$ is hydrogen;
each $R^8$ is $C_{2-10}$ alkyl; and
Q and $Q^1$ are each $OR^4$.

In one embodiment, each $R^7$ is independently hydrogen, alkyl optionally substituted with alkoxy, aryl, or aralkyl.

In one embodiment, each $R^7$ is independently hydrogen, methyl, 1-methylpropyl, (S)-1-methylpropyl, isobutyl, t-butoxymethyl, phenyl, or benzyl.

In one embodiment, each $R^7$ is independently hydrogen or methyl.

In one embodiment, each $R^8$ is independently $C_{2-6}$ alkyl.

In one embodiment, each $R^8$ is independently $C_{3-6}$ alkyl.

In one embodiment, each $R^8$ is independently alkyl, aryl, aralkyl or alkylheteroaryl.

In one embodiment, each $R^8$ is independently aralkyl.

In one embodiment, each $R^8$ is benzyl.

In one embodiment, each $R^8$ is alkylheteroaryl.

In one embodiment, each $R^8$ is 1-H-indol-3-ylmethyl.

In one embodiment, each $R^8$ is alkyl is optionally substituted by alkoxy.

In one embodiment, each $R^8$ is t-butoxymethyl.

In one embodiment, each $R^8$ is independently hydrogen, methyl, 1-methylpropyl, (S)-1-methylpropyl, isobutyl, t-butoxymethyl, phenyl, or benzyl.

In one embodiment, $R^7$ and $R^8$ together with the carbon atom to which they are attached form cyclopenyl.

In one embodiment, $Q^1$ is $OR^4$ and $R^4$ is alkyl or cycloalkyl.

In one embodiment, $R^4$ is methyl, ethyl, propryl, isopropyl, or butyl.

In some embodiments, when $E, Q, Q^1, R^1, R^2, R^5, R^6$, n and m form at least one amino acid group, and the amino acid is in the L-configuration.

In one embodiment, X is O.

In one embodiment, Base is adenine, cytosine, guanine, xanthine, hypoxanthine, thymine or uridine.

In one embodiment, Base is cytosine.

In one embodiment, Base is guanine

In one embodiment, Base is uridine.

In another embodiment, Base is selected from one of formulae (i) to (xv):

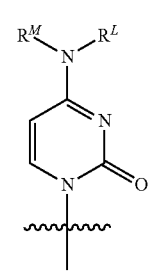
(i)

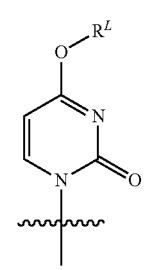
(ii)

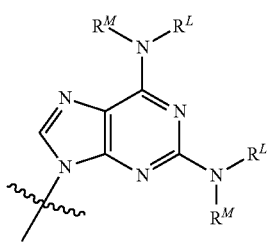
(iii)

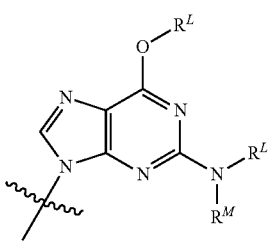
(iv)

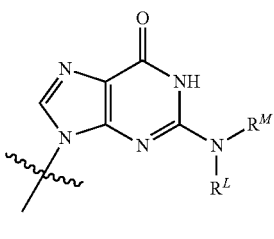
(v)

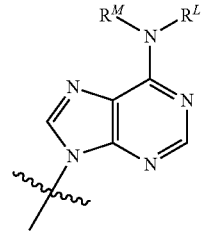
(vi)

(vii) 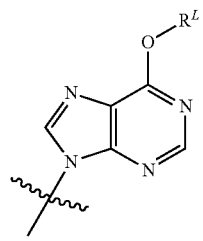

(viii) 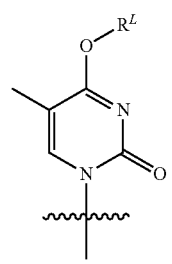

(ix) 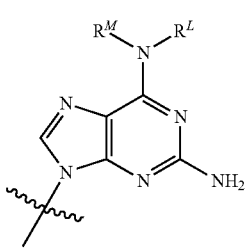

(x) 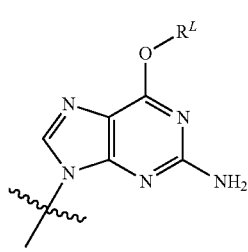

(xi) 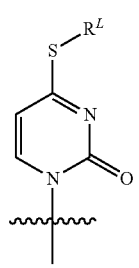

(xii) 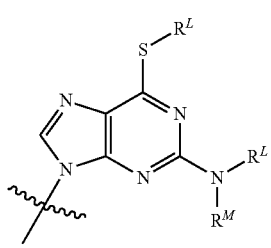

(xiii) 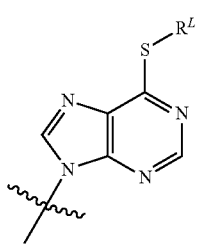

(xiv) 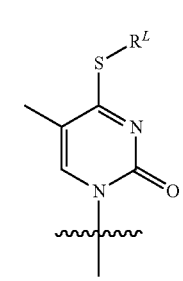

(xv) 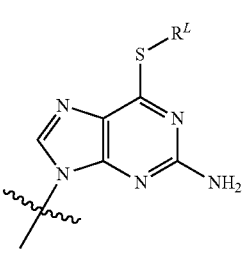

wherein $R^L$ and $R^M$ are each as defined herein.

In one embodiment, each $R^L$ is independently hydrogen, alkyl or cycloalkyl. In certain embodiments, each $R^L$ is independently hydrogen, methyl, ethyl, propyl, isopropyl, cyclopropyl, or cyclopentyl.

In one embodiment, each $R^M$ is independently hydrogen, alkyl or cycloalkyl. In certain embodiments, each $R^M$ is independently hydrogen or methyl.

In one embodiment, when Base is of formula (i), (iii), (v), (vi) or (ix), each $R^L$ is independently hydrogen or cyclopropyl, and $R^M$ is hydrogen. In one embodiment, when Base is of formula (i), (v), (vi) or (ix), $R^L$ is cyclopropyl, and $R^M$ is hydrogen.

In one embodiment, when Base is of formula (ii), (iv), (vii), (viii), (x), (xi), (xii), (xiii), (xiv) or (xv), each $R^L$ is independently hydrogen, methyl, ethyl, propyl, or isopropyl; and $R^M$ is hydrogen. In one embodiment, when Base is of formula (ii), (vii), (viii), (x), (xi), (xiii), (xiv) or (xv), $R^L$ is methyl, ethyl, propyl, or isopropyl; and $R^M$ is hydrogen. In one embodiment, when Base is of formula (ii), (iv), (vii), (viii), (x), (xi), (xii), (xiii), (xiv) or (x), each $R^L$ is independently hydrogen or methyl; and $R^M$ is hydrogen. In one embodiment, when Base is of formula (ii), (vii), (viii), (x), (xi), (xiii), (xiv), or (xv), $R^L$ is methyl and $R^M$ is hydrogen.

In one embodiment, the compound provided herein is a compound of the formula:

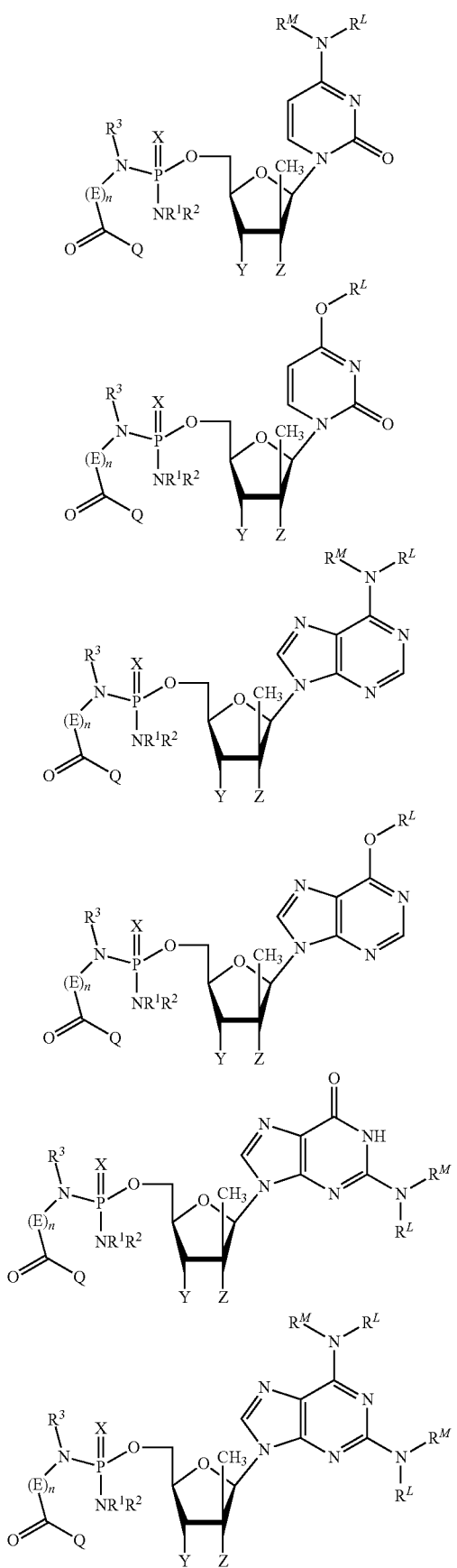

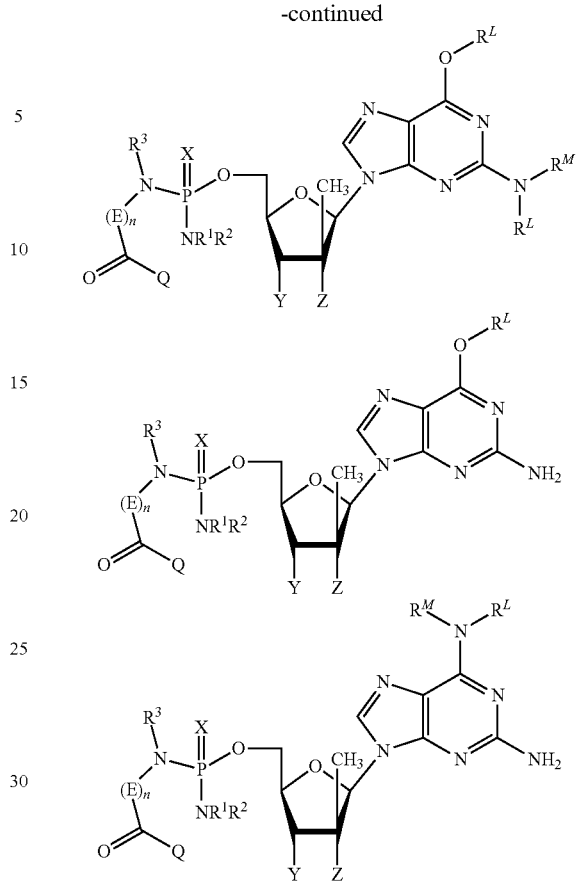

wherein, X, E, n, Q, $R^1$, $R^2$, and $R^3$ are as described in Formula II;

Y is $OR^9$;

Z is $OR^{10}$ or F;

each of $R^9$ and $R^{10}$ is hydrogen; or $R^9$ and $R^{10}$ together with C(O) and the oxygen or sufur atoms on which they are attached form a 5 membered heterocyclic ring;

each $R^L$ is independently hydrogen, alkyl, cycloalkyl, acyl, carbamyl, CO-alkyl, CO-aryl, CO-alkoxyalkyl, CO-aryloxyalkyl, CO-substituted aryl, sulfonate ester, alkyl sulfonyl, aryl sulfonyl, arylalkyl sulfonyl, a lipid, a phospholipid, an amino acid or a carbohydrate; and each $R^M$ is independently hydrogen or alkyl; or $R^L$ and $R^M$ together with the N atom to which they are attached from heterocyclyl.

In another embodiment, X, E, Q, $R^1$, $R^2$, and $R^3$ are as described herein;

Y is $OR^9$;

Z is $OR^{10}$;

each of $R^9$ and $R^{10}$ is hydrogen;

$R^L$ is hydrogen, alkyl or cycloalkyl; and $R^M$ is hydrogen or alkyl.

In another embodiment, $R^9$ and $R^{10}$ together with C(O) and the oxygen or sufur atoms on which they are substituted form a 5 membered ring; $R^L$ is hydrogen, alkyl or cycloalkyl; and $R^M$ is hydrogen.

In one embodiment, the nucleosides that can be derivatized to include a phosphoramidate, e.g., at the 5' position, include:

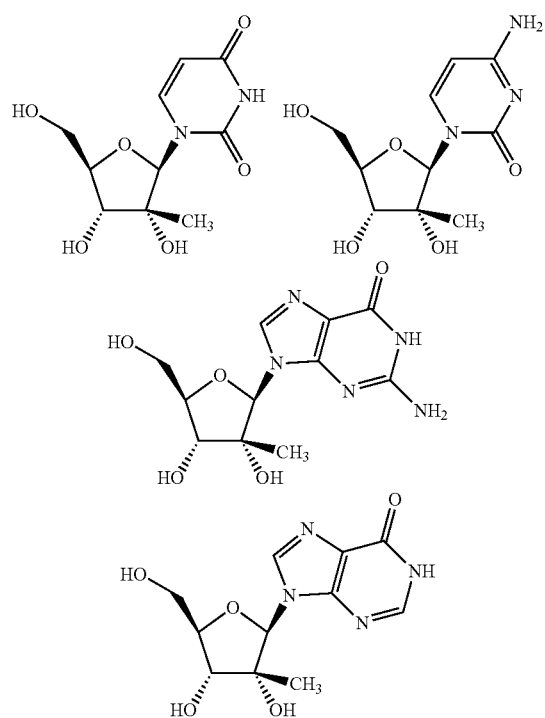
In another embodiment, the nucleosides that can be derivatized to include a phosphoramidate, e.g., at the 5' position, include:
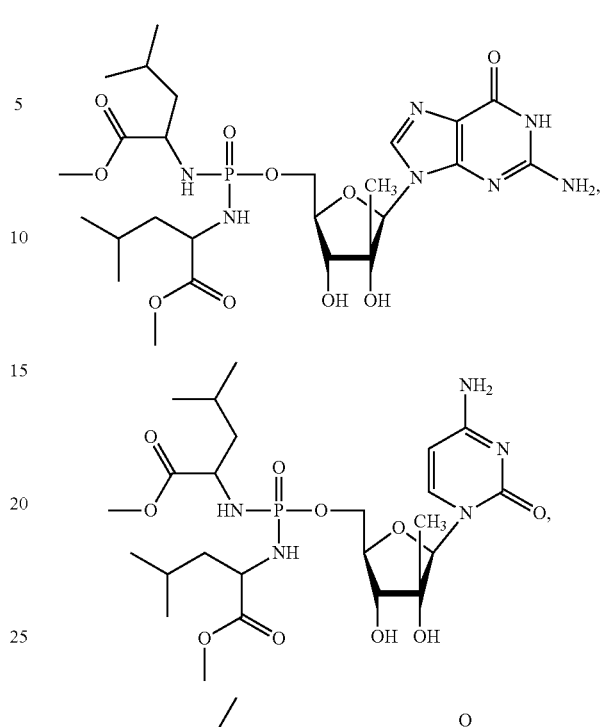
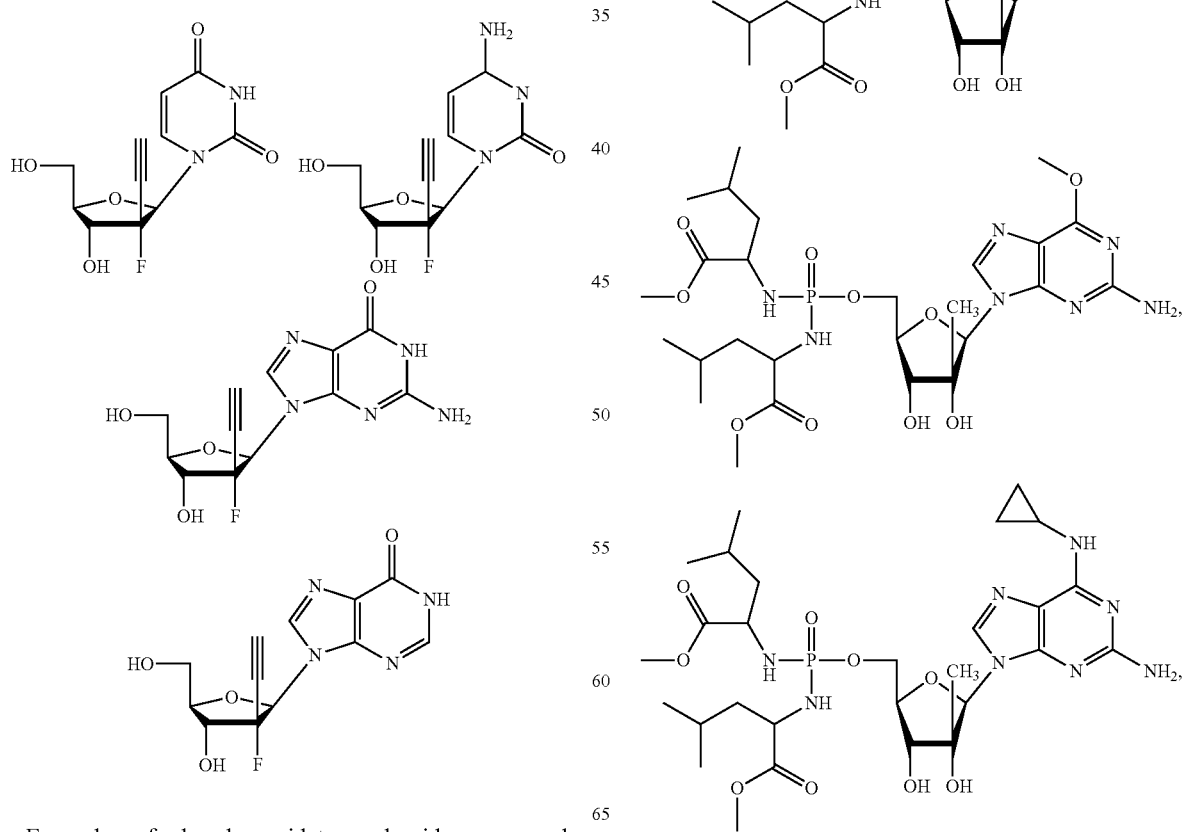
Examples of phosphoramidate nucleoside compounds include:

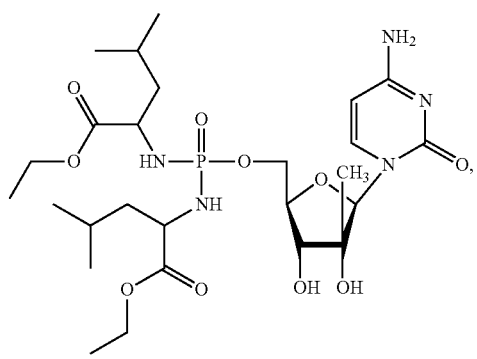
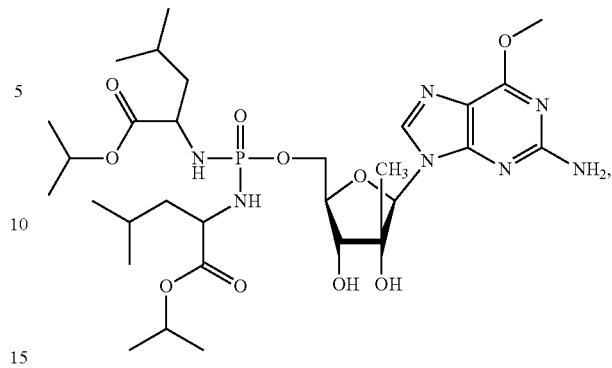
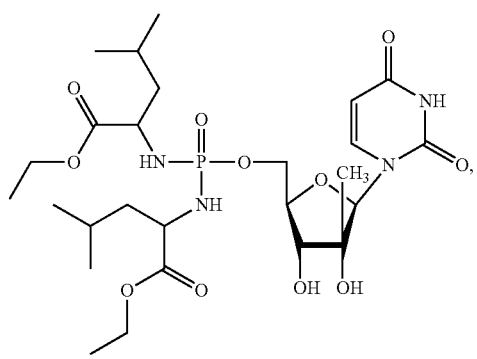
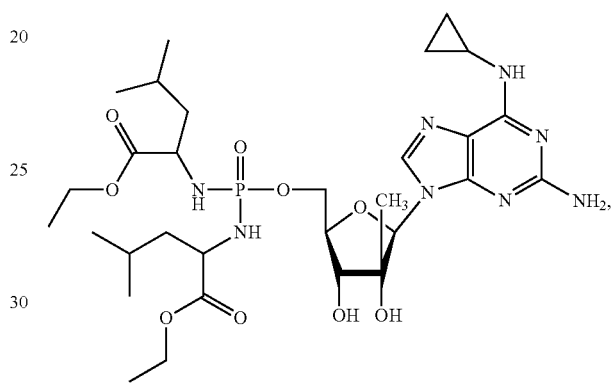
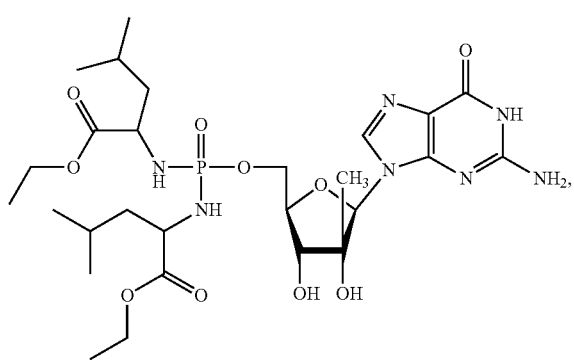
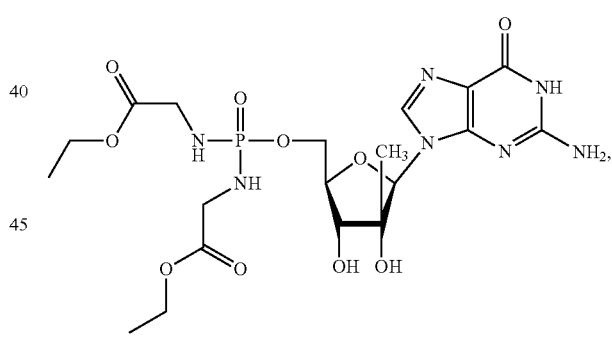
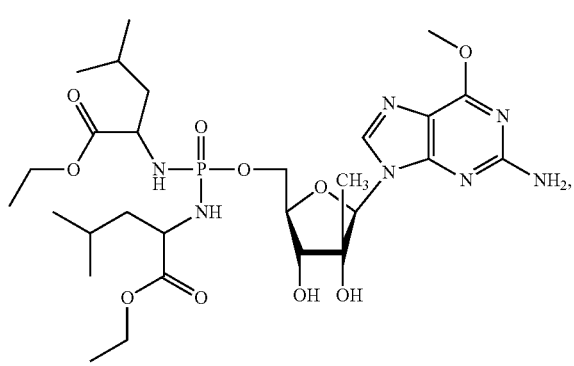
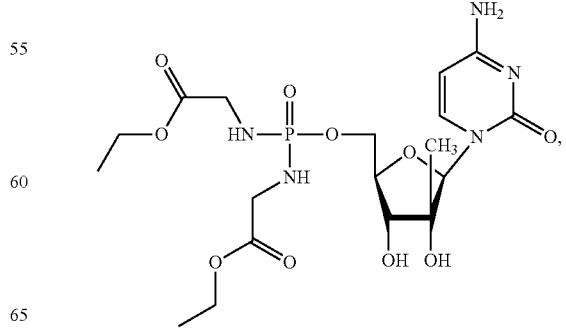

35
-continued
36
-continued
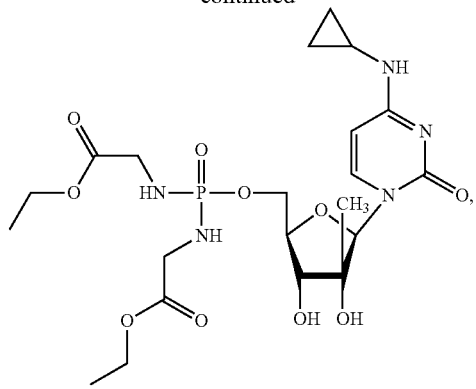
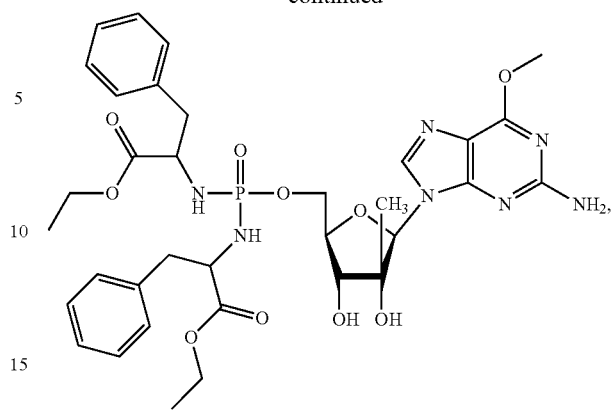

37
-continued
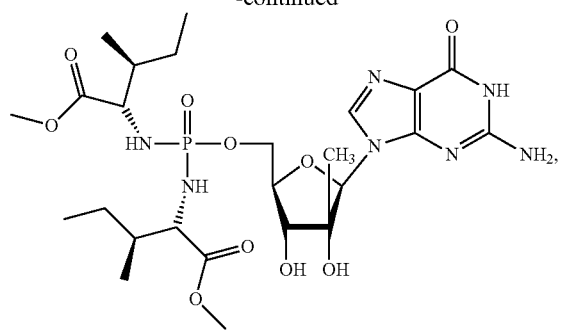
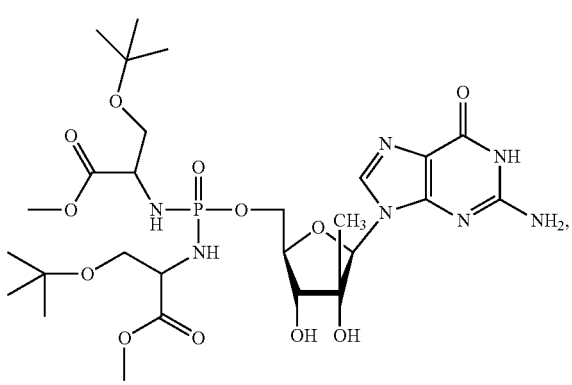
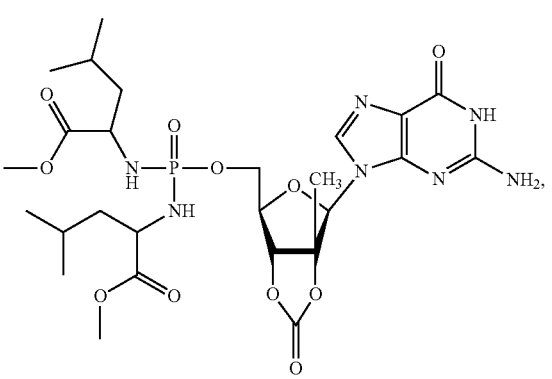
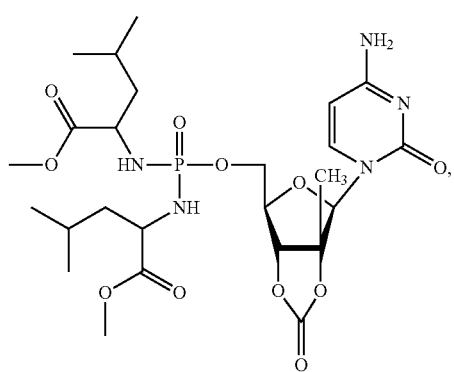
38
-continued
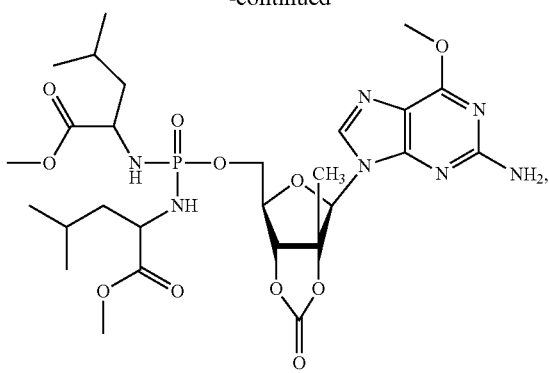
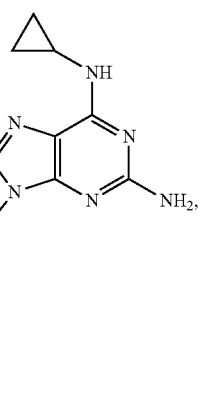
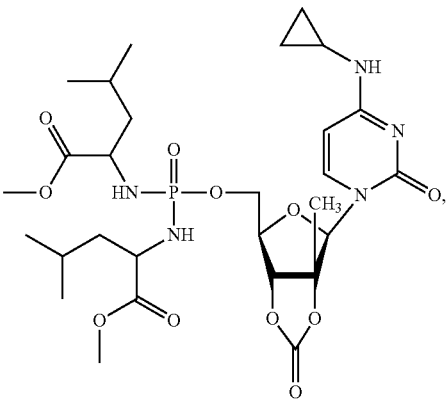

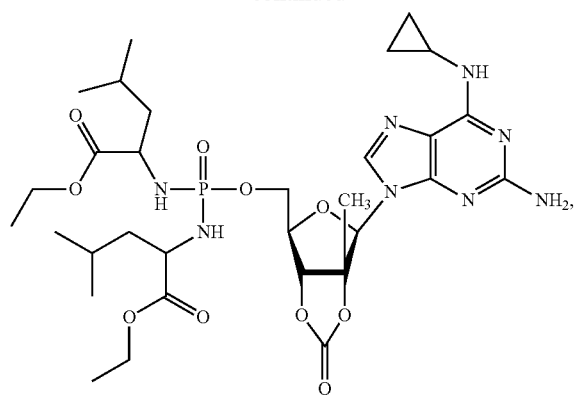
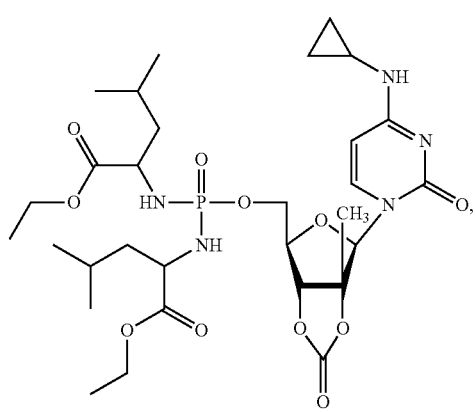
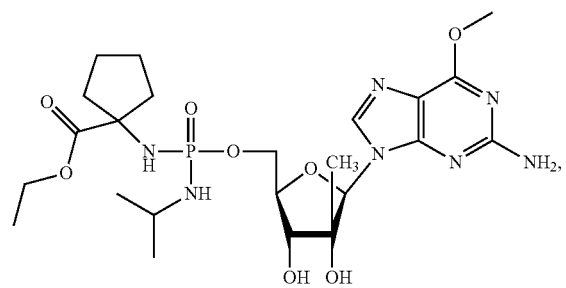
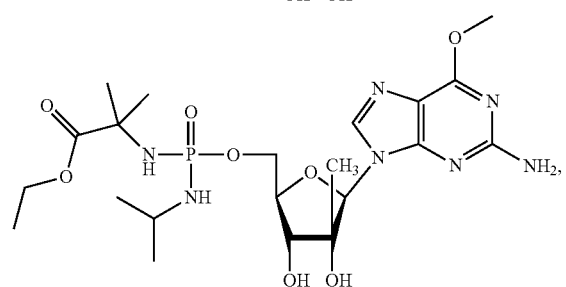
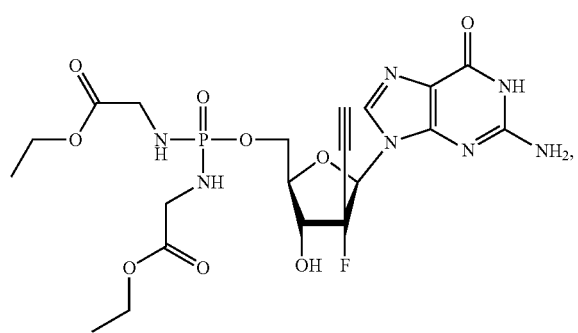
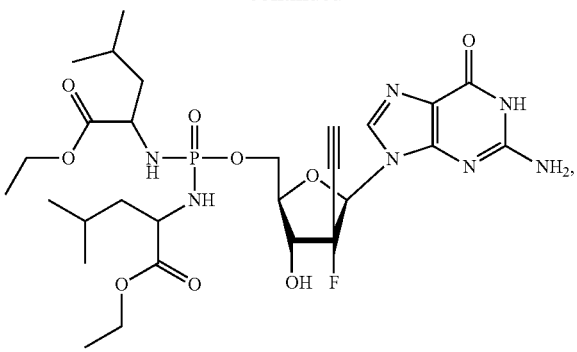
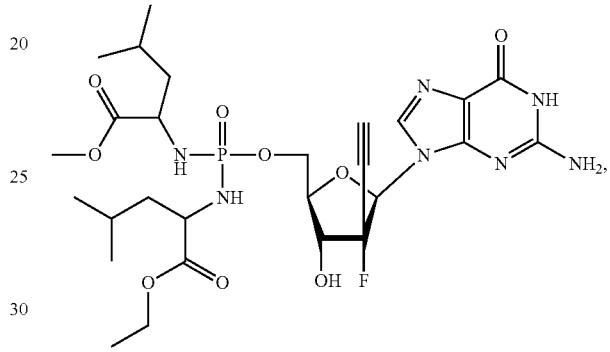
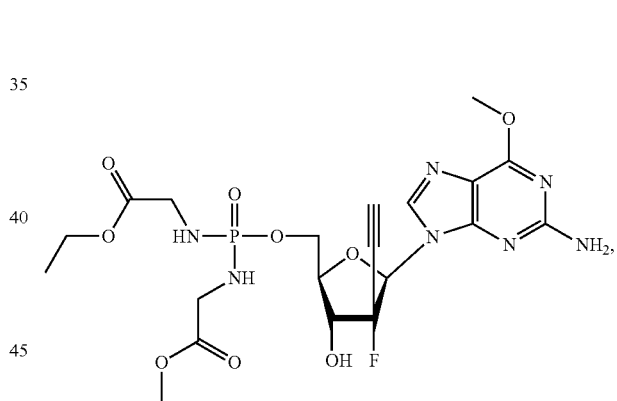
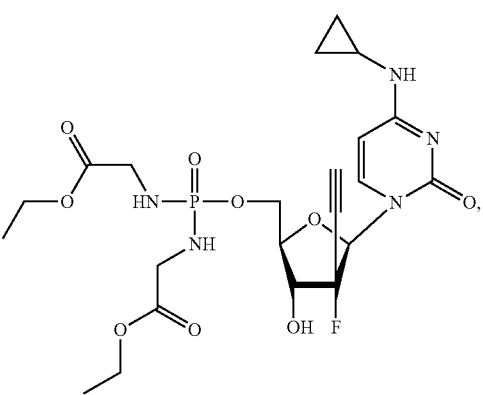

41
-continued
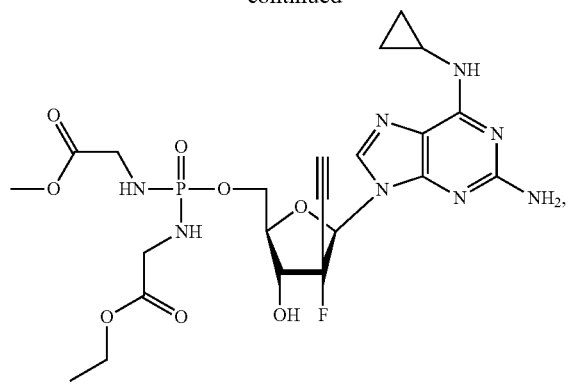
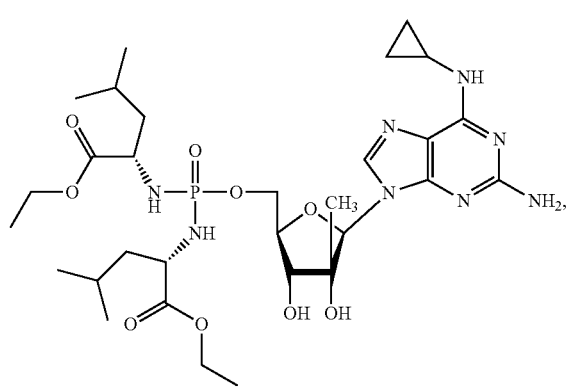
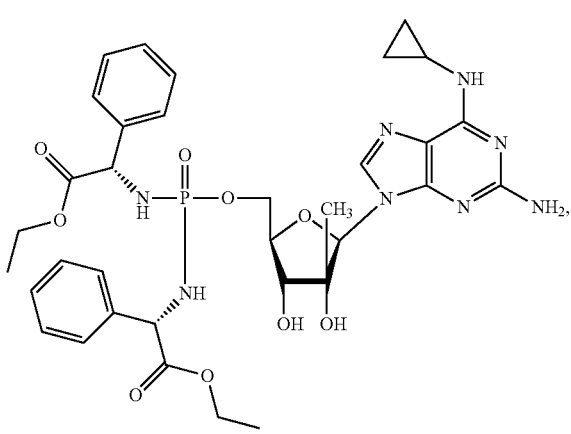
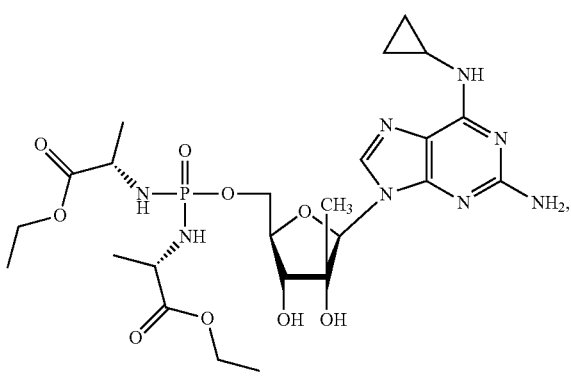
42
-continued
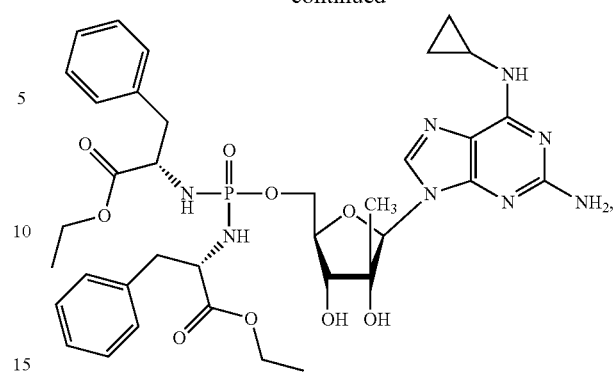
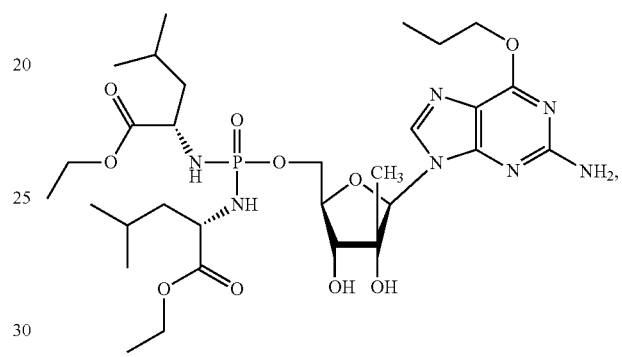
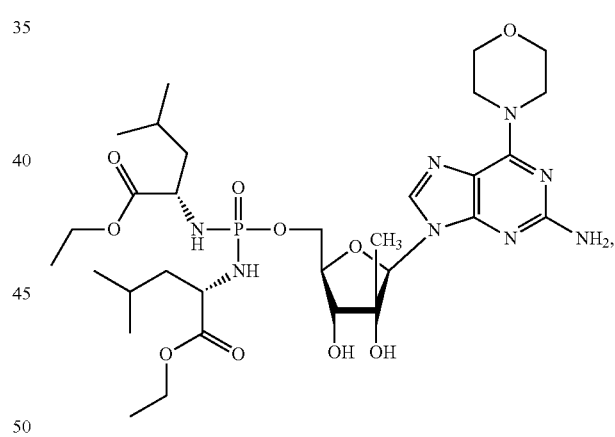
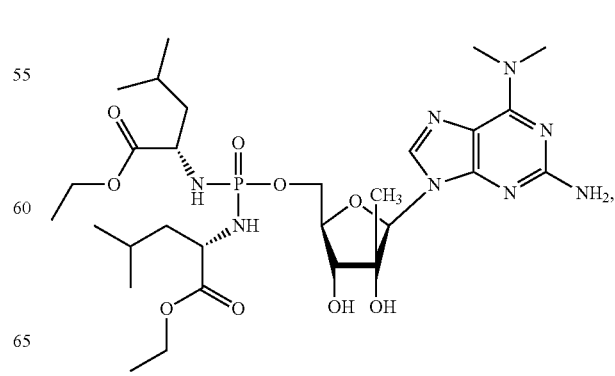

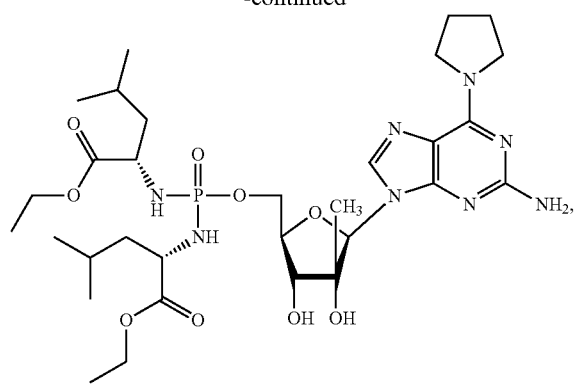
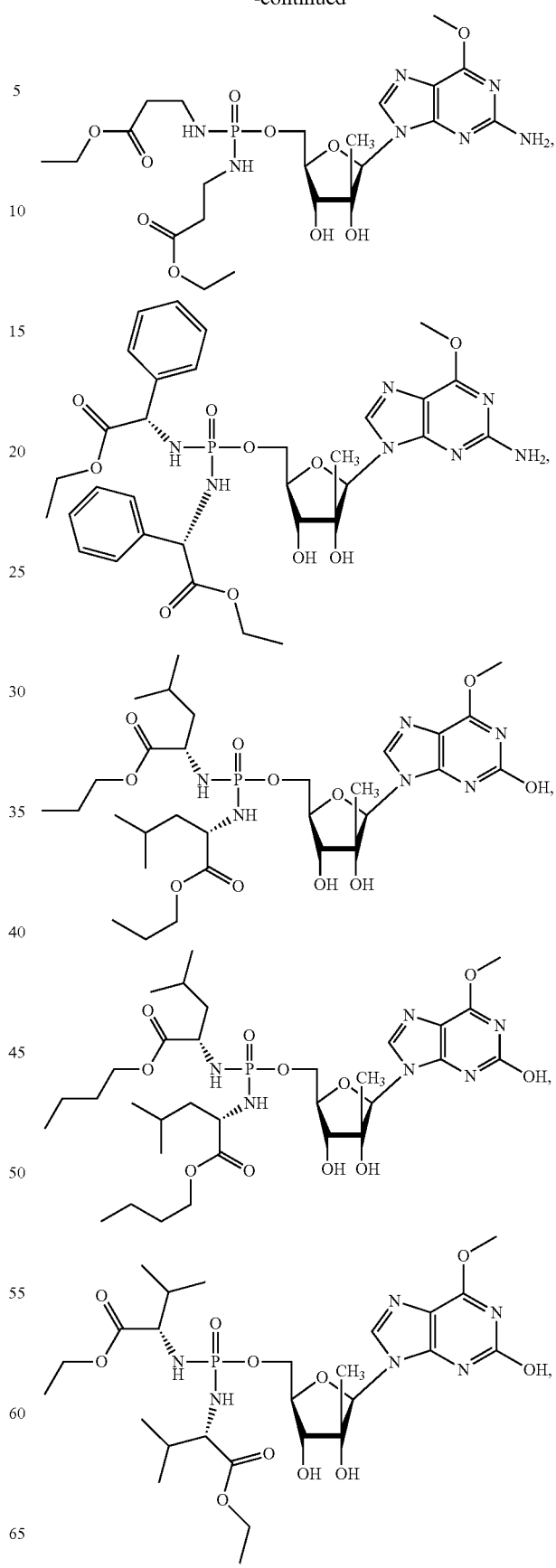

-continued
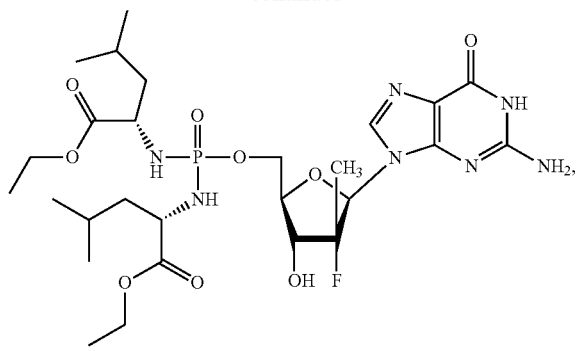
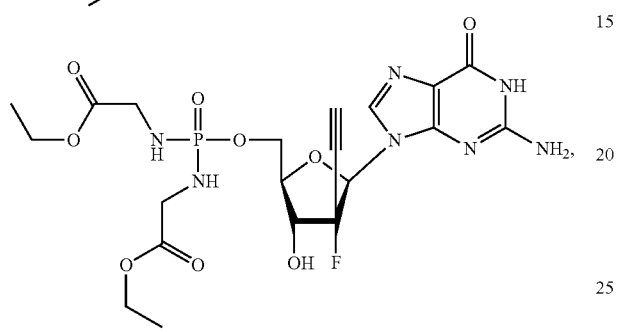
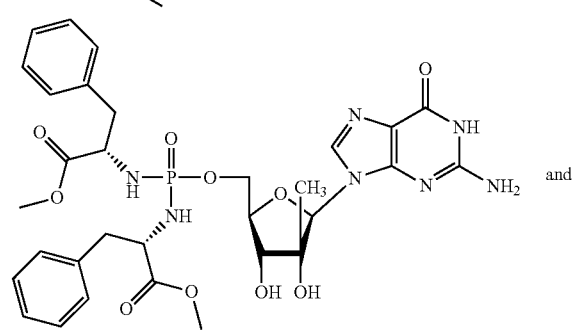
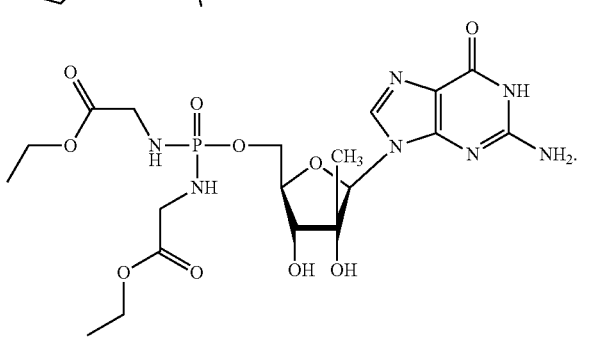
In one embodiment, the nucleosides that can be derivatized to include a phosphoramidate, e.g., at the 5' position include:
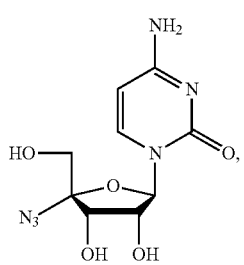
-continued
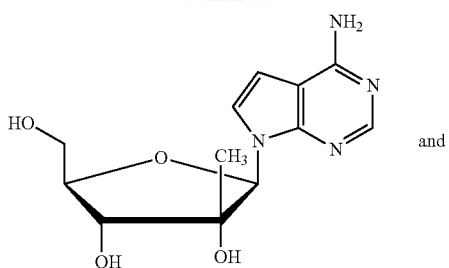
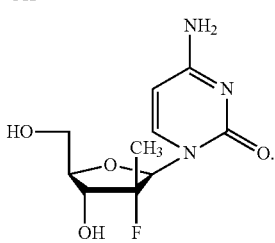
Exemplary nucleoside drugs useful in the treatment of hepatitis C infection that can be derivatized as described herein are:
| Name | Structure |
|---|---|
| Ribavirin | 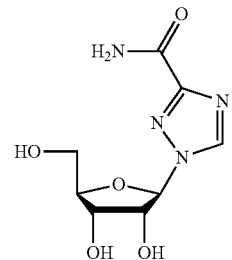 |
| Viramidine | 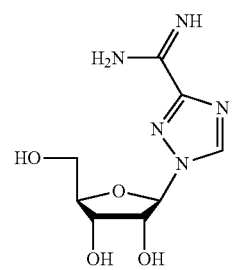 |
| Valopicitabine (NM283) | 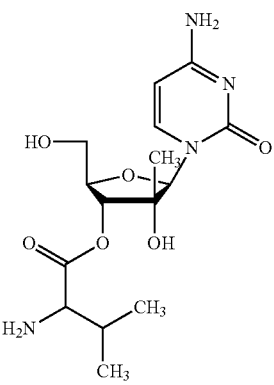 |

| Name | Structure |
|---|---|
| 2'-C-methylcytidine (NM107) | 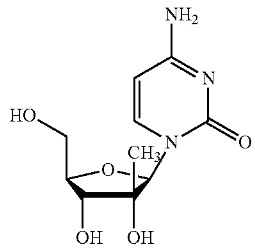 |
| PSI-6130 | 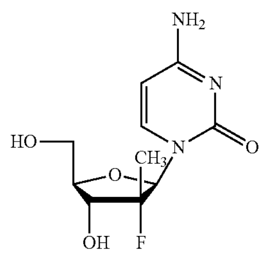 |
| PSI-6206 | 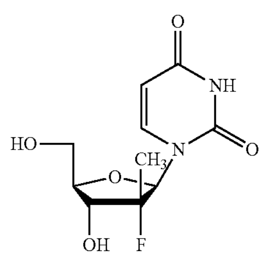 |
| MK-0608 | 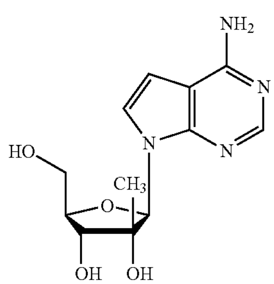 |
| 7-Fluoro-MK-0608 | 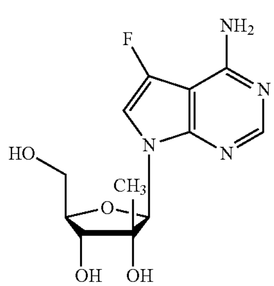 |
| NM108 | 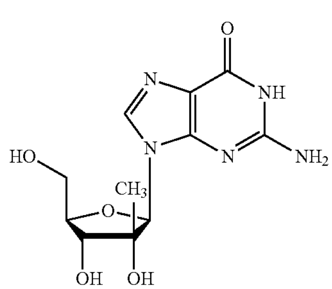 |

| Name | Structure |
|---|---|
| PSI-35938 | 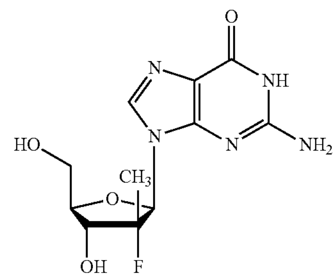 |
| R1479 | 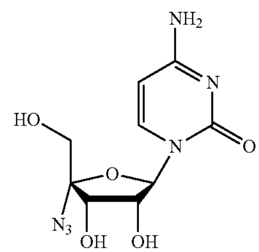 |
| | |
| | |
| | |

Further exemplary anti-viral nucleoside analogs that can be used as R are disclosed in International Publication Nos. WO2005021568, WO2006094347 and WO2006093987; and US Patent Publication No. US20050215510; the disclosure of each of which is incorporated herein by reference in its entirety.

In one embodiment, R is a moiety derivable by removal of a hydrogen from a hydroxy group of an interfering RNA (iRNA) based antivirals, including short interfering RNA (siRNA) based antivirals. Such compounds are described in International Patent Publication Nos. WO/03/070750 and WO 2005/012525; U.S. Pat. Nos. 7,176,304; 7,109,165; 7,041,817; 7,034,009; 7,022,828; 6,852,535 and 6,849,726; and US Patent Publication No. US 2004/0209831; the disclosure of each of which is incorporated herein by reference in its entirety.

In another embodiment, the compound provided herein is a compound of formula:

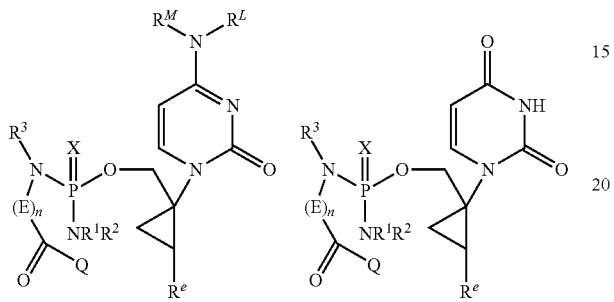

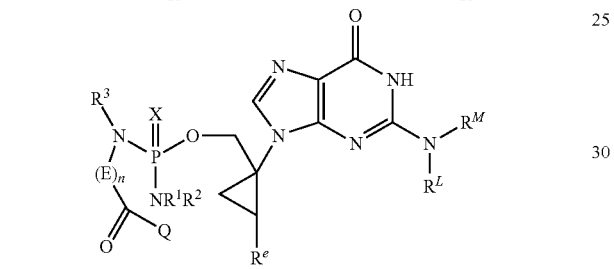

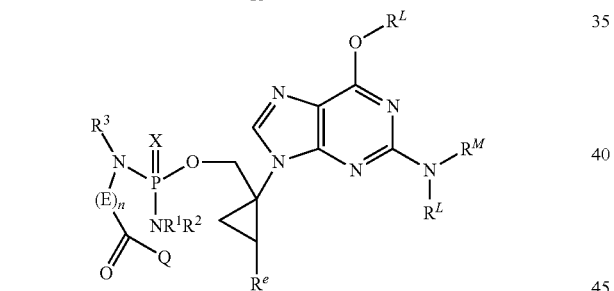

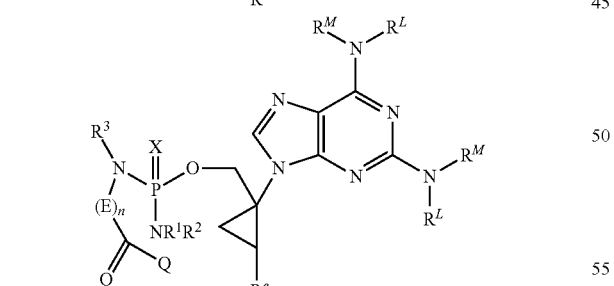

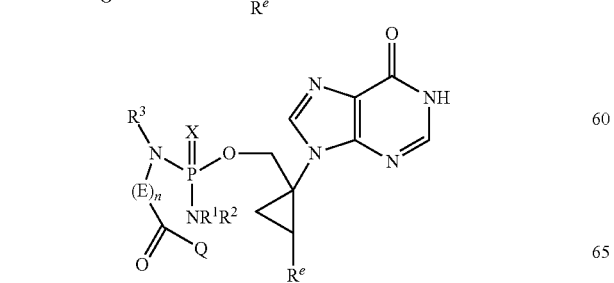

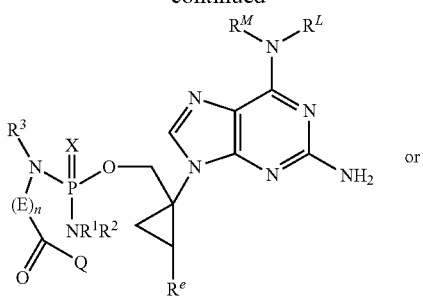

or

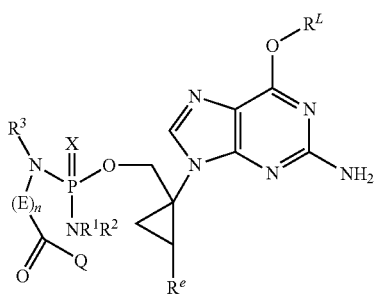

wherein X, E, n, Q, $R^1$, $R^2$ and $R^3$ are as described herein; each $R^e$ is hydrogen, alkyl or cycloalkyl; each $R^L$ is independently hydrogen, alkyl, cycloalkyl, acyl, carbamyl, CO-alkyl, CO-aryl, CO-alkoxyalkyl, CO-aryloxyalkyl, CO-substituted aryl, sulfonate ester, alkyl sulfonyl, aryl sulfonyl, arylalkyl sulfonyl, a lipid, a phospholipid, an amino acid or a carbohydrate; and each $R^M$ is independently hydrogen or alkyl; or $R^L$ and $R^M$ together with the N atom to which they are attached from 5-membered heterocyclyl.

In certain embodiments, $R^e$ is methyl, ethyl or propyl.

In certain embodiments, R is a moiety derivable by removal of a hydrogen from a hydroxy group of a nucleoside described in U.S. Patent Application Publication No. US 2006/0111324 A1, the content of which is hereby incorporated by reference in its entirety.

In another embodiment, the compound provided herein is a compound of formula:

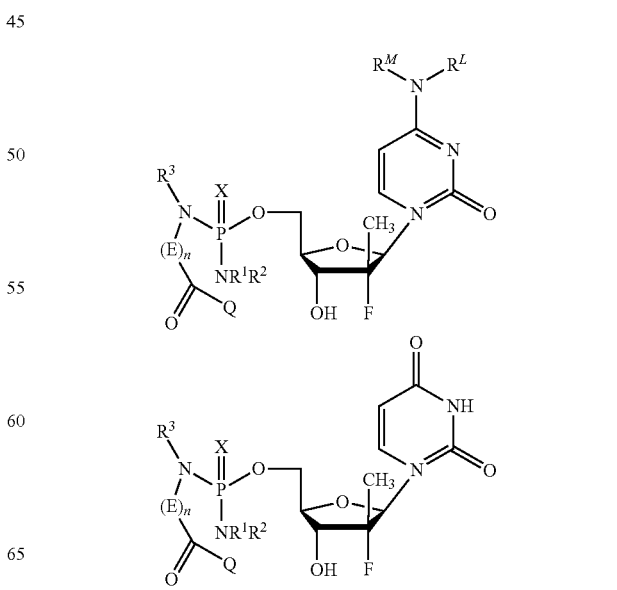

-continued

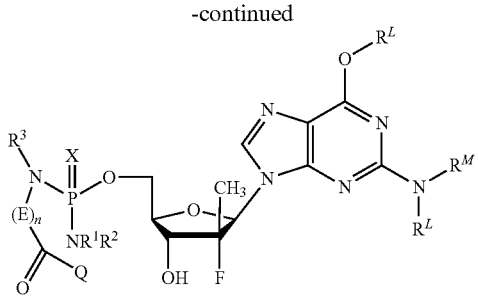

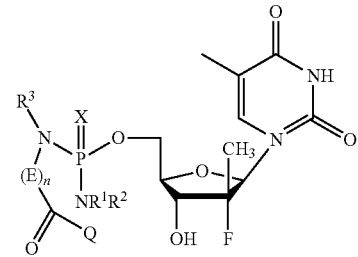

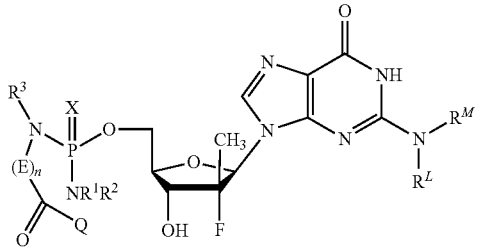

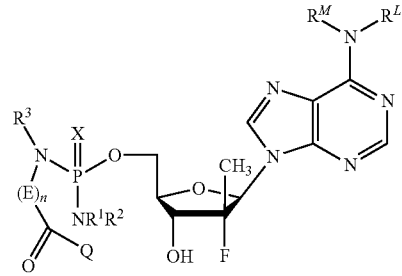

or

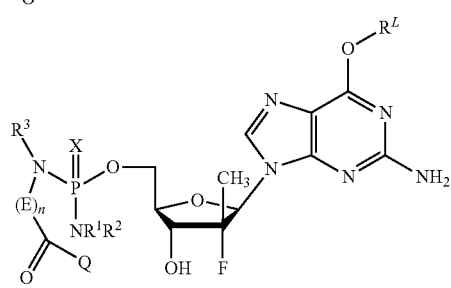

wherein X, E, n, Q, $R^1$, $R^2$ and $R^3$ are as described herein; each $R^L$ is independently hydrogen, alkyl, cycloalkyl, acyl, carbamyl, CO-alkyl, CO-aryl, CO-alkoxyalkyl, CO-aryloxyalkyl, CO-substituted aryl, sulfonate ester, alkyl sulfonyl, aryl sulfonyl, arylalkyl sulfonyl, a lipid, a phospholipid, an amino acid or a carbohydrate; and each $R^M$ is independently hydrogen or alkyl; or $R^L$ and $R^M$ together with the N atom to which they are attached from 5-membered heterocyclyl.

In another embodiment, $R^L$ is hydrogen.

In another embodiment, $R^M$ is hydrogen.

In another embodiment, the compound provided herein is a compound of formula:

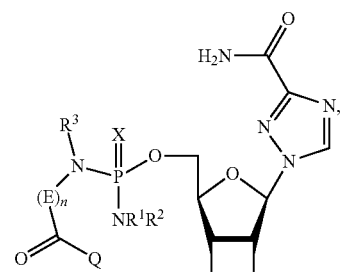

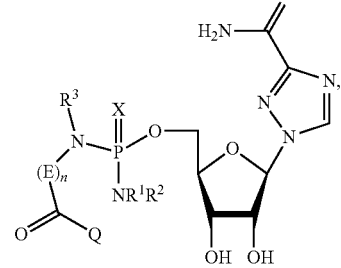

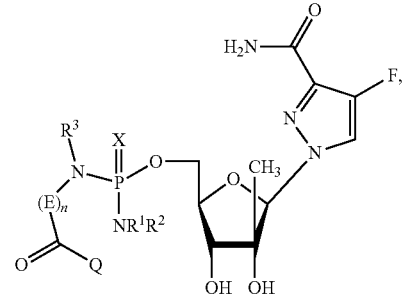

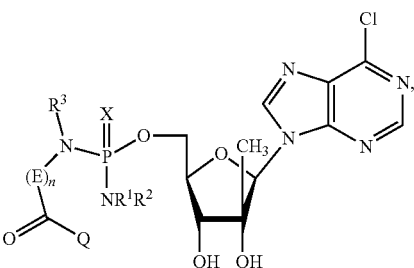

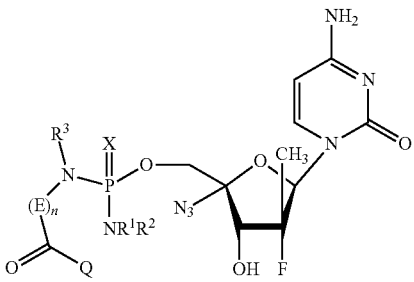

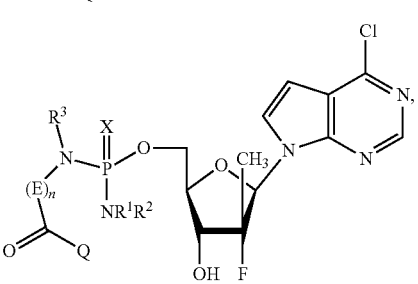

-continued

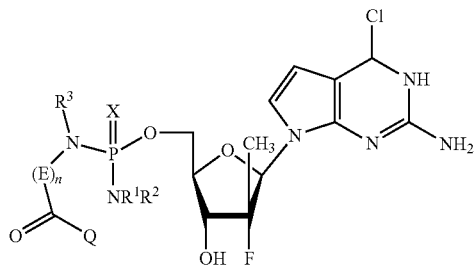

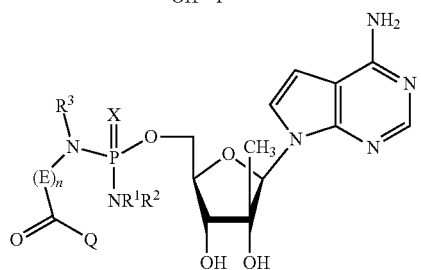

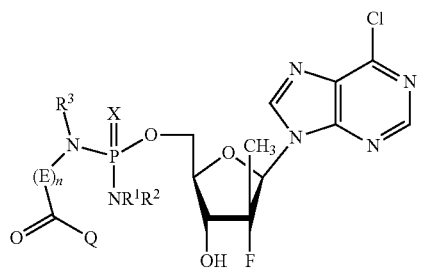

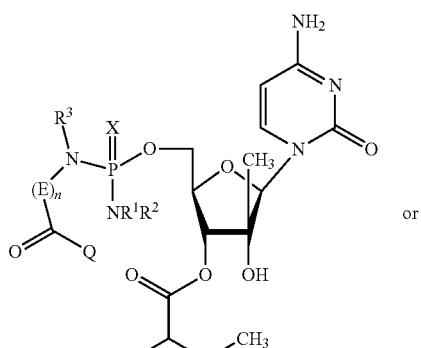

or

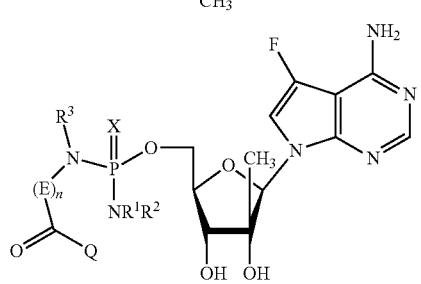

wherein X, E, n, Q, $R^1$, $R^2$ and $R^3$ are each as described herein.

In another embodiment, the compound provided herein is a compound of formula:

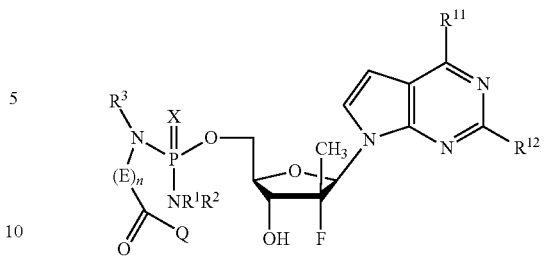

wherein X, E, n, Q, $R^1$, $R^2$ and $R^3$ are each as described herein; and $R^{11}$ and $R^{12}$ are each independently hydrogen, hydroxy, alkoxy, amino, alkylamino, dialkylamino, thioalkyl, F, Cl, Br, or I.

In one embodiment, R is a moiety derivable by removal of a hydrogen from a hydroxy group of a natural nucleoside. In one embodiment, R is a moiety derivable by removal of a hydrogen from a hydroxy group of a 2'- or 3'-prodrug of a biologically active 1', 2', 3' or 4'C-branched β-D nucleoside. The term 1', 2', 3' or 4'C-branched, as used in this specification, includes a nucleoside that has an additional non-natural substituent in the 1', 2', 3' or 4'-position (i.e., carbon is bound to four nonhydrogen substituents). The term 2'-prodrug, as used herein, includes a 1', 2', 3' or 4' C-branched-β-D nucleoside that has a biologically cleavable moiety at the 2'-position, including, but not limited to acyl, and in one embodiment, a natural or synthetic D or L amino acid, in one embodiment, an L-amino acid. The term 3'-prodrug, as used herein, includes a 1', 2', 3' or 4' C-branched-β-D nucleoside that has a biologically cleavable moiety at the 3'-position, including, but not limited to acyl, and in one embodiment, a natural or synthetic D or L amino acid, in one embodiment, an L-amino acid. In one embodiment, the amino acid is valine.

Examples of prodrugs (that can be further derivatized as described herein to include a phosphoramidate moiety, for example, at the 5' position) include 2'-L-valine ester of β-D-2'-C-methyl-cytidine; 2'-L-valine ester of β-D-2'-C-methyl-thymidine; 2'-L-valine ester of β-D-2'-C-methyl-adenosine; 2'-L-valine ester of β-D-2'-C-methyl-guanosine; 2'-L-valine ester of β-D-2'-C-methyl-5-fluorocytidine; 2'-L-valine ester of β-D-2'-C-methyl-uridine; 2'-acetyl ester of β-D-2'-C-methyl-cytidine; 2'-acetyl ester of β-D-2'-C-methyl-thymidine; 2'-acetyl ester of β-D-2'-C-methyl-adenosine; 2'-acetyl ester of β-D-2'-C-methyl-guanosine; 2'-acetyl ester of β-D-2'-C-methyl-5-fluoro-cytidine; and 2'-esters of β-D-2'-C-methyl-(cytidine, 5-fluorocytidine, guanosine, uridine, adenosine, or thymidine) wherein (i) the 2' ester is an amino acid ester; or (ii) the 2' ester is an alkyl or aryl ester.

Further examples of prodrugs are 3'-L-valine ester of β-D-2'-C-methyl-cytidine; 3'-L-valine ester of β-D-2'-C-methyl-thymidine; 3'-L-valine ester of β-D-2'-C-methyl-adenosine; 3'-L-valine ester of β-D-2'-C-methyl-guanosine; 3'-L-valine ester of β-D-2'-C-methyl-5-fluorocytidine; 3'-L-valine ester of β-D-2'-C-methyl-uridine; 3'-acetyl ester of β-D-2'-C-methyl-cytidine; 3'-acetyl ester of β-D-2'-C-methyl-thymidine; 3'-acetyl ester of β-D-2'-C-methyl-adenosine; 3'-acetyl ester of β-D-2'-C-methyl-guanosine; 3'-acetyl ester of β-D-2'-C-methyl-5-fluoro-cytidine; and 3'-esters of β-D-2'-C-methyl-(cytidine, 5-fluorocytidine, guanosine, uridine, adenosine, or thymidine) wherein (i) the 3' ester is an amino acid ester; or (ii) the 3' ester is an alkyl or aryl ester.

Additional examples of prodrugs include 2',3'-L-divaline ester of β-D-2'-C-methyl-cytidine (dival-2'-Me-L-dC); 2',3'-L-divaline ester of β-D-2'-C-methyl-thymidine; 2',3'-L-divaline ester of β-D-2'-C-methyl-adenosine; 2',3'-L-divaline ester of β-D-2'-C-methyl-guanosine; 2',3'-L-divaline ester of β-D-2'-C-methyl-5-fluoro-cytidine; 2',3'-L-divaline ester of β-D-2'-C-methyl-uridine; 2',3'-diacetyl ester of β-D-2'-C-methyl-cytidine; 2',3'-diacetyl ester of β-D-2'-C-methyl-thymidine; 2',3'-diacetyl ester of β-D-2'-C-methyl-adenosine; 2',3'-diacetyl ester of β-D-2'-C-methyl-guanosine; 2',3'-diacetyl ester of β-D-2'-C-methyl-5-fluoro-cytidine; and 2',3'-diesters of β-D-2'-C-methyl-(cytidine, 5-fluorocytidine, guanosine, uridine, adenosine, or thymidine) wherein (i) the 2' ester is an amino acid ester and the 3'-ester is an alkyl or aryl ester; (ii) both esters are amino acid esters; (iii) both esters are independently alkyl or aryl esters; or (iv) the 2' ester is an alkyl or aryl ester and the 3'-ester is an amino acid ester.

Optically Active Compounds

It is appreciated that compounds provided herein have several chiral centers and may exist in and be isolated in optically active and racemic forms. Some compounds may exhibit polymorphism. It is to be understood that any racemic, optically-active, diastereomeric, polymorphic, or stereoisomeric form, or mixtures thereof, of a compound provided herein, which possess the useful properties described herein is within the scope of the invention. It being well known in the art how to prepare optically active forms (for example, by resolution of the racemic form by recrystallization techniques, by synthesis from optically-active starting materials, by chiral synthesis, or by chromatographic separation using a chiral stationary phase).

In particular, since the 1' and 4' carbons of a nucleoside are chiral, their nonhydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring β-D nucleosides), cis (with both groups "down", which is a nonnaturally occurring β-L configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the non-naturally occurring configuration.

Likewise, most amino acids are chiral (designated as L or D, wherein the L enantiomer is the naturally occurring configuration) and can exist as separate enantiomers.

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In some embodiments, compositions of phosphoramidate compounds are provided that are substantially free of a designated enantiomer of that nucleoside. In one embodiment, in the methods and compounds of this invention, the compounds are substantially free of enantiomers. In some embodiments, the composition includes that includes a compound that is at least 85, 90%, 95%, 98%, 99% to 100% by weight, of the compound, the remainder comprising other chemical species or enantiomers.

Isotopically Enriched Compounds

Also provided herein are isotopically enriched compounds, including but not limited to isotopically enriched phosphoramidate nucleoside compounds.

Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sufur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Preparation of Compounds

The compounds provided herein can be prepared, isolated or obtained by any method apparent to those of skill in the art. Exemplary methods of preparation are described in detail in the examples below. In certain embodiments, compounds provided herein can be prepared according to Scheme 1 or 2 below:

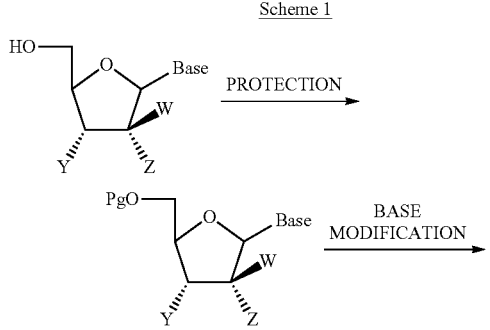

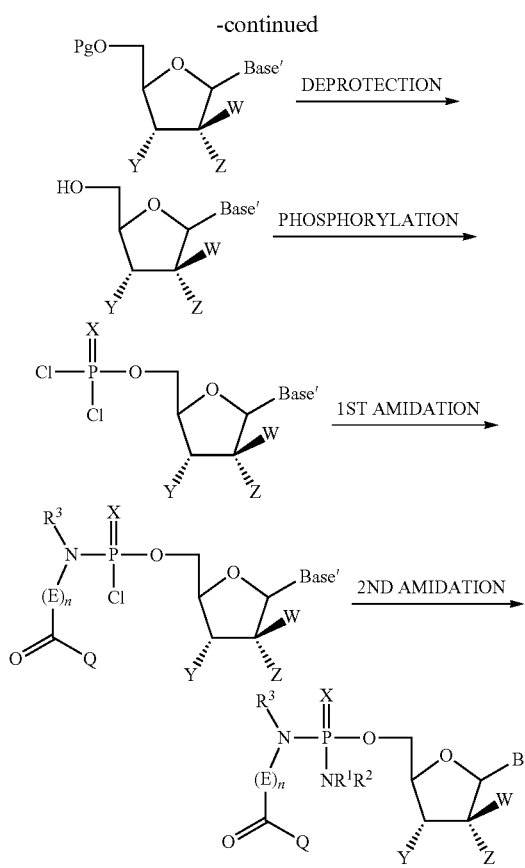
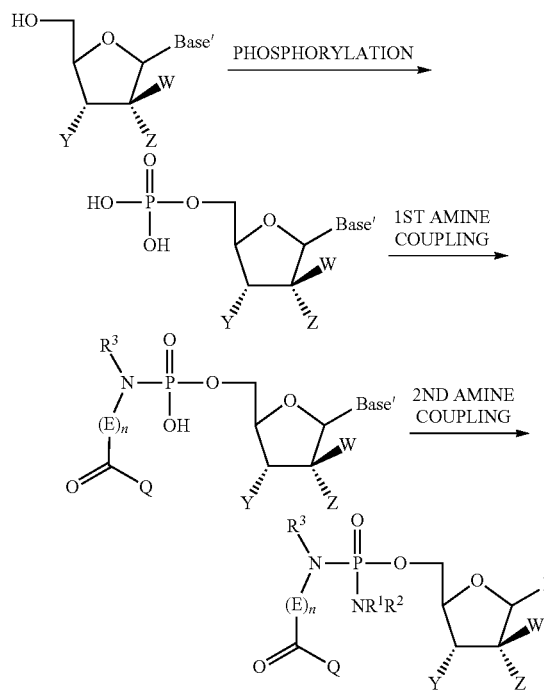
In certain embodiments, one or more protection or deprotection steps may be included in the methods of preparation described in Schemes 1 and 2, wherein X, Y, Z, W, E, n, Q, R¹, R² and R³ are each as described herein; and Base' is the same as defined for Base.
In certain embodiments, compounds provided herein can be prepared according to Scheme 3 or 4 below:
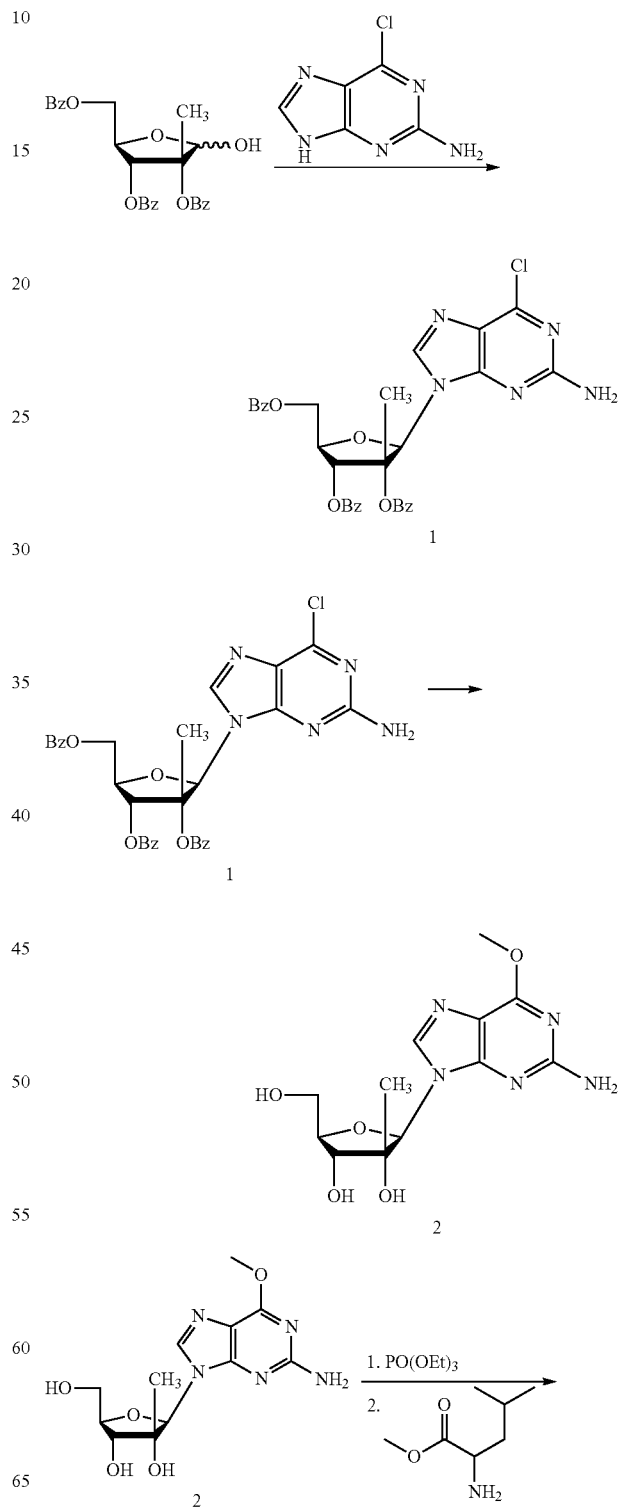

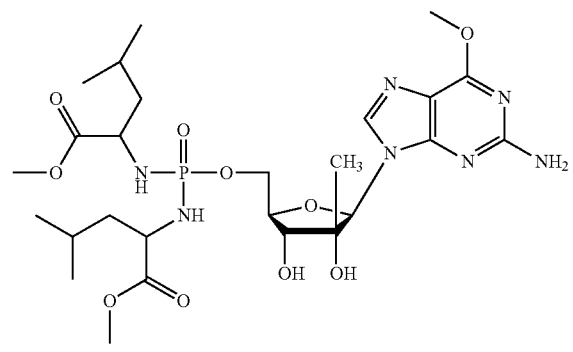

3

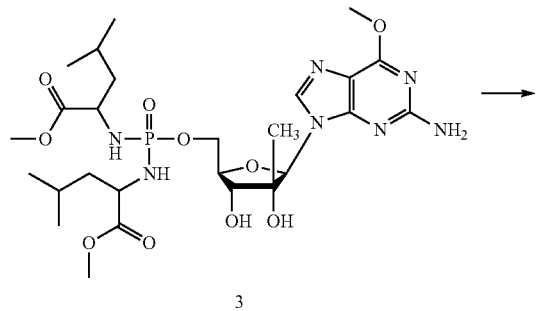

3

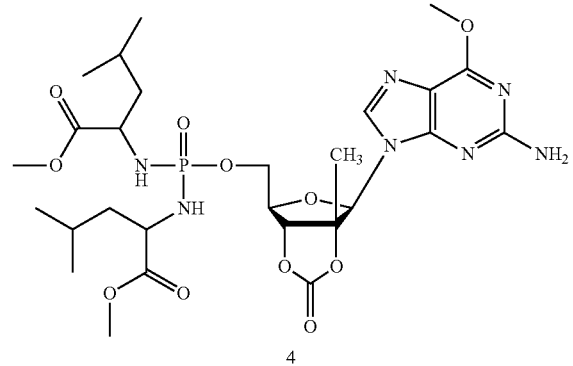

4

Scheme 4

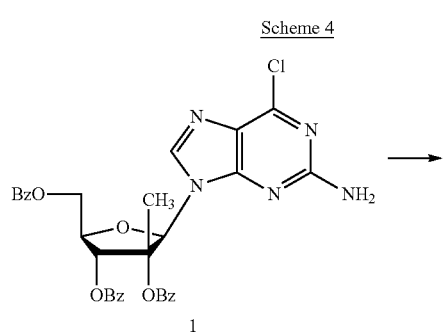

1

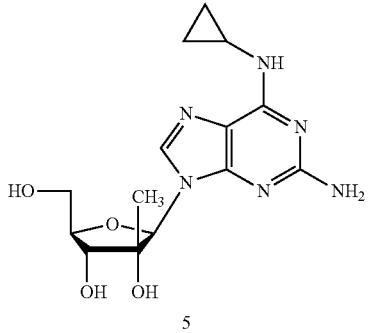

5

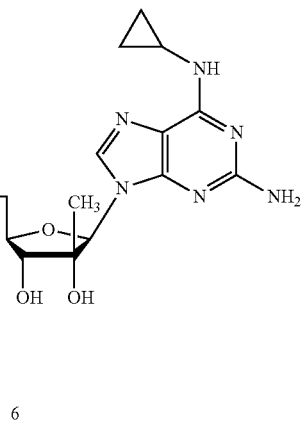

5

6

In addition, certain nucleosides and analogs thereof and prodrugs thereof can be prepared according to methods described in U.S. Pat. Nos. 6,812,219; 7,105,493; 7,101,861; 6,914,054; 6,555,676; 7,202,224; 7,105,499; 6,777,395; 6,914,054; 7,192,936; US publication Nos. 2005203243; 2007087960; 2007060541; 2007060505; 2007060504; 2007060503; 2007060498; 2007042991; 2007042990; 2007042940; 2007042939 and 2007037735; International Publication Nos. WO 04/003000; WO 04/022999; WO 04/002422; WO 01/90121 and WO 01/92282. Other patents/patent applications disclosing nucleoside analogs to treat hepatitis C virus that can be derivatized as described herein include: PCT/CA00/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002); PCT/US02/03086 (WO 02/057287; filed Jan. 18, 2002); U.S. Pat. Nos. 7,202,224; 7,125,855; 7,105,499 and 6,777,395 by Merck & Co., Inc.; PCT/EP01/09633 (WO 02/18404; published Aug. 21, 2001); US 2006/0040890; 2005/0038240; 2004/0121980; U.S. Pat. Nos. 6,846,810; 6,784,166 and 6,660,721 by Roche; PCT Publication Nos. WO 01/79246 (filed Apr. 13, 2001), WO 02/32920 (filed Oct.

18, 2001) and WO 02/48165; US 2005/0009737 and US 2005/0009737; U.S. Pat. Nos. 7,094,770 and 6,927,291 by Pharmasset, Ltd. Contents of these references are hereby incorporated by reference in their entireties.

Pharmaceutical Compositions and Methods of Administration

Phosphoramidate compounds of a variety of therapeutic agents can be formulated into pharmaceutical compositions using methods available in the art and those disclosed herein. Such compounds can be used in some embodiments to enhance delivery of the drug to the liver. Therapeutic agents that can be derivatized to phosphoramidate compound form include any anti-viral agent that includes, or has been derivatized to include a reactive group for attachment of the phosphoramidate moiety, including but not limited to nucleosides and nucleoside analogues including acyclic nucleosides. Any of the compounds disclosed herein can be provided in the appropriate pharmaceutical composition and be administered by a suitable route of administration.

The methods provided herein encompass administering pharmaceutical compositions containing at least one compound as described herein, including a compound of general Formula I or II, if appropriate in the salt form, either used alone or in the form of a combination with one or more compatible and pharmaceutically acceptable carriers, such as diluents or adjuvants, or with another anti-HCV agent.

In certain embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art.

In clinical practice the active agents provided herein may be administered by any conventional route, in particular orally, parenterally, rectally or by inhalation (e.g. in the form of aerosols). In certain embodiments, the compound provided herein is administered orally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In one embodiment, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, for example, in the U.S. Pharmocopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, for example, an animal subject, such as a mammalian subject, for example, a human subject.

A pharmaceutical composition is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intratumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington's Pharmaceutical Sciences, 20th ed., Mack Publishing, Easton Pa. (2000).

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 20th ed., Mack Publishing, Easton Pa. (2000).

In certain embodiments, the oral dosage forms are solid and prepared under anhydrous conditions with anhydrous ingredients, as described in detail in the sections above. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In one embodiment, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321: 574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In one embodiment, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, $16^{th}$, $18th$ and $20^{th}$ eds., Mack Publishing, Easton Pa. (1980, 1990 & 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, $16^{th}$, $18th$ and $20^{th}$ eds., Mack Publishing, Easton Pa. (1980, 1990 & 2000).

Depending on the specific tissue to be treated, additional components may be used prior to, in conjunction with, or subsequent to treatment with active ingredients provided. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, the doctor will determine the posology which he considers most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating or preventing an HCV infection in a subject by administering, to a subject in need thereof, an effective amount of a compound provided herein, or a pharmaceutically acceptable salt thereof. The amount of the compound or composition which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the conditions described herein lie within the range of from about 0.1 mg to about 1000 mg per day, given as a single once-a-day dose or as divided doses throughout a day. In one embodiment, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiment, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses.

In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable salt thereof, in a form suitable for administration. Such forms are described in detail above. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

The dosages of the second agents are to be used in the combination therapies provided herein. In certain embodiments, dosages lower than those which have been or are currently being used to prevent or treat HCV infection are used in the combination therapies provided herein. The recommended dosages of second agents can be obtained from the knowledge of those of skill. For those second agents that are approved for clinical use, recommended dosages are described in, for example, Hardman et al., eds., 1996, Goodman & Gilman's The Pharmacological Basis Of Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J., which are incorporated herein by reference in its entirety.

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound provided herein and a second agent are administered to a patient, for example, a mammal, such as a human, in a sequence and within a time interval such that the compound provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compound provided herein and the second agent are cyclically administered to a patient. Cycling therapy involves the administration of a first agent (e.g., a first prophylactic or therapeutic agents) for a period of time, followed by the administration of a second agent and/or third agent (e.g., a second and/or third prophylactic or therapeutic agents) for a period of time and repeating this sequential administration. Cycling therapy can reduce the development of resistance to one or more of the therapies, avoid or reduce the side effects of one of the therapies, and/or improve the efficacy of the treatment.

In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In one embodiment, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of a liver disorder such as HCV infections. The kits can include a compound or composition provided herein, a second agent or composition, and instructions providing information to a health care provider regarding usage for treating the disorder.

Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Methods of Use

The phosphoramidate compounds of a variety of therapeutic agents can be formed using methods available in the art and those disclosed herein. Such compounds can be used in some embodiments to enhance delivery of the drug to the liver.

Therapeutic agents that can be derivatized to a phosphoramidate compound form include any anti-viral agent that includes, or has been derivatized to include a reactive group for attachment of the phosphoramidate moiety, including but not limited to nucleosides and nucleoside analogues including acyclic nucleosides.

Advantageously, such phosphoramidate compounds advantageously may have enhanced delivery to the liver. In some embodiments, the compounds permit delivery of an active 5'-monophosphate of a nucleoside to the liver, which can enhance the formation of active triphosphorylated compound.

In one embodiment, provided herein are methods for the treatment and/or prophylaxis of a host infected with Flaviviridae that includes the administration of an effective amount of a compounds provided herein, or a pharmaceutically acceptable salt thereof. In one embodiment, provided herein are methods for treating an HCV infection in a subject. In certain embodiments, the methods encompass the step of administering to the subject in need thereof an amount of a compound effective for the treatment or prevention of an HCV infection in combination with a second agent effective for the treatment or prevention of the infection. The compound can be any compound as described herein, and the second agent can be any second agent described in the art or herein. In certain embodiments, the compound is in the form of a pharmaceutical composition or dosage form, as described elsewhere herein.

Flaviviridae that can be treated are discussed generally in *Fields Virology*, Editors: Fields, B. N., Knipe, D. M., and Howley, P. M., Lippincott-Raven Publishers, Philadelphia, Pa., Chapter 31, 1996. In a particular embodiment of the invention, the Flaviviridae is HCV. In an alternate embodiment of the invention, the Flaviviridae is a flavivirus or pestivirus. Specific flaviviruses include, without limitation: Absettarov, Alfuy, Apoi, Aroa, Bagaza, Banzi, Bouboui, Bussuquara, Cacipacore, Carey Island, Dakar bat, Dengue 1, Dengue 2, Dengue 3, Dengue 4, Edge Hill, Entebbe bat, Gadgets Gully, Hanzalova, Hypr, Ilheus, Israel turkey meningoencephalitis, Japanese encephalitis, Jugra, Jutiapa, Kadam, Karshi, Kedougou, Kokobera, Koutango, Kumlinge, Kunjin, Kyasanur Forest disease, Langat, Louping ill, Meaban, Modoc, Montana myotis leukoencephalitis, Murray valley encephalitis, Naranjal, Negishi, Ntaya, Omsk hemorrhagic fever, Phnom-Penh bat, Powassan, Rio Bravo, Rocio, Royal Farm, Russian spring-summer encephalitis, Saboya, St. Louis encephalitis, Sal Vieja, San Perlita, Saumarez Reef, Sepik, Sokuluk, Spondweni, Stratford, Tembusu, Tyuleniy, Uganda S, Usutu, Wesselsbron, West Nile, Yaounde, Yellow fever, and Zika.

Pestiviruses that can be treated are discussed generally in *Fields Virology*, Editors: Fields, B. N., Knipe, D. M., and Howley, P. M., Lippincott-Raven Publishers, Philadelphia, Pa., Chapter 33, 1996. Specific pestiviruses include, without limitation: bovine viral diarrhea virus ("BVDV"), classical swine fever virus ("CSFV," also called hog cholera virus), and border disease virus ("BDV").

In certain embodiments, the subject can be any subject infected with, or at risk for infection with, HCV. Infection or risk for infection can be determined according to any technique deemed suitable by the practitioner of skill in the art. In one embodiment, subjects are humans infected with HCV.

In certain embodiments, the subject has never received therapy or prophylaxis for an HCV infection. In further embodiments, the subject has previously received therapy or prophylaxis for an HCV infection. For instance, in certain embodiments, the subject has not responded to an HCV therapy. For example, under current interferon therapy, up to 50% or more HCV subjects do not respond to therapy. In certain embodiments, the subject can be a subject that received therapy but continued to suffer from viral infection or one or more symptoms thereof. In certain embodiments, the subject can be a subject that received therapy but failed to achieve a sustained virologic response. In certain embodiments, the subject has received therapy for an HCV infection but has failed to show, for example, a 2 $\log_{10}$ decline in HCV RNA levels after 12 weeks of therapy. It is believed that subjects who have not shown more than 2 $\log_{10}$ reduction in serum HCV RNA after 12 weeks of therapy have a 97-100% chance of not responding.

In certain embodiments, the subject is a subject that discontinued an HCV therapy because of one or more adverse events associated with the therapy. In certain embodiments, the subject is a subject where current therapy is not indicated. For instance, certain therapies for HCV are associated with neuropsychiatric events. Interferon (IFN)-alfa plus ribavirin is associated with a high rate of depression. Depressive symptoms have been linked to a worse outcome in a number of medical disorders. Life-threatening or fatal neuropsychiatric events, including suicide, suicidal and homicidal ideation, depression, relapse of drug addiction/overdose, and aggressive behavior have occurred in subjects with and without a previous psychiatric disorder during HCV therapy. Interferon-induced depression is a limitation for the treatment of chronic hepatitis C, especially for subjects with psychiatric disorders. Psychiatric side effects are common with interferon therapy and responsible for about 10% to 20% of discontinuations of current therapy for HCV infection.

Accordingly, provided are methods of treating or preventing an HCV infection in subjects where the risk of neuropsychiatric events, such as depression, contraindicates treatment with current HCV therapy. In one embodiment, provided are methods of treating or preventing HCV infection in subjects where a neuropsychiatric event, such as depression, or risk of such indicates discontinuation of treatment with current HCV therapy. Further provided are methods of treating or preventing HCV infection in subjects where a neuropsychiatric event, such as depression, or risk of such indicates dose reduction of current HCV therapy.

Current therapy is also contraindicated in subjects that are hypersensitive to interferon or ribavirin, or both, or any other component of a pharmaceutical product for administration of interferon or ribavirin. Current therapy is not indicated in subjects with hemoglobinopathies (e.g., thalassemia major, sickle-cell anemia) and other subjects at risk from the hematologic side effects of current therapy. Common hematologic side effects include bone marrow suppression, neutropenia and thrombocytopenia. Furthermore, ribavirin is toxic to red blood cells and is associated with hemolysis. Accordingly, in one embodiment, provided are methods of treating or preventing HCV infection in subjects hypersensitive to interferon or ribavirin, or both, subjects with a hemoglobinopathy, for instance thalassemia major subjects and sickle-cell anemia subjects, and other subjects at risk from the hematologic side effects of current therapy.

In certain embodiments, the subject has received an HCV therapy and discontinued that therapy prior to administration of a method provided herein. In further embodiments, the subject has received therapy and continues to receive that therapy along with administration of a method provided herein. The methods can be co-administered with other therapy for HBC and/or HCV according to the judgment of one of skill in the art. In certain embodiments, the methods or compositions provided herein can be co-administered with a reduced dose of the other therapy for HBC and/or HCV.

In certain embodiments, provided are methods of treating a subject that is refractory to treatment with interferon. For instance, in some embodiments, the subject can be a subject that has failed to respond to treatment with one or more agents selected from the group consisting of interferon, interferon α, pegylated interferon α, interferon plus ribavirin, interferon α plus ribavirin and pegylated interferon α plus ribavirin. In some embodiments, the subject can be a subject that has responded poorly to treatment with one or more agents selected from the group consisting of interferon, interferon α, pegylated interferon α, interferon plus ribavirin, interferon α plus ribavirin and pegylated interferon α plus ribavirin. A pro-drug form of ribavirin, such as taribavirin, may also be used.

In certain embodiments, the subject has, or is at risk for, co-infection of HCV with HIV. For instance, in the United States, 30% of HIV subjects are co-infected with HCV and evidence indicates that people infected with HIV have a much more rapid course of their hepatitis C infection. Maier and Wu, 2002, *World J Gastroenterol* 8:577-57. The methods provided herein can be used to treat or prevent HCV infection in such subjects. It is believed that elimination of HCV in these subjects will lower mortality due to end-stage liver disease. Indeed, the risk of progressive liver disease is higher in subjects with severe AIDS-defining immunodeficiency than in those without. See, e.g., Lesens et al., 1999, *J Infect Dis* 179:1254-1258. In one embodiment, compounds provided herein have been shown to suppress HIV in HIV subjects. Thus, in certain embodiments, provided are methods of treating or preventing HIV infection and HCV infection in subjects in need thereof.

In certain embodiments, the compounds or compositions are administered to a subject following liver transplant. Hepatitis C is a leading cause of liver transplantation in the U.S, and many subjects that undergo liver transplantation remain HCV positive following transplantation. In one embodiment, provided are methods of treating such recurrent HCV subjects with a compound or composition provided herein. In certain embodiments, provided are methods of treating a subject before, during or following liver transplant to prevent recurrent HCV infection.

Assay Methods

Compounds can be assayed for HCV activity according to any assay known to those of skill in the art.

Further, compounds can be assayed for accumulation in liver cells of a subject according to any assay known to those of skill in the art. In certain embodiments, a compound can be administered to the subject, and a liver cell of the subject can be assayed for the compound or a derivative thereof, e.g. a nucleoside, nucleoside phosphate or nucleoside triphosphate derivative thereof.

In one embodiment, a phosphoramidate nucleoside compound is administered to cells, such as liver cells, in vivo or in vitro, and the nucleoside triphosphate levels delivered intracellularly are measured, to indicate delivery of the compound and triphosphorylation in the cell. The levels of intracellular nucleoside triphosphate can be measured using analytical techniques known in the art. Methods of detecting ddATP are described herein below by way of example, but other nucleoside triphosphates can be readily detected using the appropriate controls, calibration samples and assay techniques.

In one embodiment, ddATP concentrations are measured in a sample by comparison to calibration standards made from control samples. The ddATP concentrations in a sample can be measured using an analytical method such as HPLC LC MS. In one embodiment, a test sample is compared to a calibration curve created with known concentrations of ddATP to thereby obtain the concentration of that sample.

In one embodiment, the samples are manipulated to remove impurities such as salts ($Na^+$, $K^+$, etc.) before analysis. In one embodiment, the lower limit of quantitation is about ~0.2 pmol/mL for hepatocyte cellular extracts particularly where reduced salt is present.

In one embodiment, the method allows successfully measuring triphosphate nucleotides formed at levels of 1-10,000 pmol per million cells in e.g. cultured hepatocytes and HepG2 cells.

Second Therapeutic Agents

In certain embodiments, the compounds and compositions provided herein are useful in methods of treatment of a liver disorder, that comprises further administration of a second agent effective for the treatment of the disorder, such as HCV infection in a subject in need thereof. The second agent can be any agent known to those of skill in the art to be effective for the treatment of the disorder, including those currently approved by the FDA.

In certain embodiments, a compound provided herein is administered in combination with one second agent. In further embodiments, a second agent is administered in combination with two second agents. In still further embodiments, a second agent is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The active compounds provided herein can be administered in combination or alternation with another therapeutic agent, in particular an anti-HCV agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. In certain embodiments, an anti-HCV (or anti-pestivirus or anti-flavivirus) compound that exhibits an $EC_{50}$ of 10-15 μM. In one embodiment, less than 1-5 μM, is desirable.

It has been recognized that drug-resistant variants of flaviviruses, pestiviruses or HCV can emerge after prolonged treatment with an antiviral agent. Drug resistance most typically occurs by mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Any of the viral treatments described in the Background of the Invention can be used in combination or alternation with the compounds described in this specification. Nonlimiting examples of second agents include:

HCV Protease inhibitors: Examples include Medivir HCV Protease Inhibitor (HCV-PI or TMC435) (Medivir/Tibotec); MK-7009 (Merck), RG7227 (ITMN-191) (Roche/Pharmasset/InterMune), boceprevir (SCH 503034) (Schering), SCH 446211 (Schering), narlaprevir SCH900518 (Schering/ Merck), ABT-450 (Abbott/Enanta), ACH-1625 (Achillion), BI 201335 (Boehringer Ingelheim), PHX1766 (Phenomix), VX-500 (Vertex) and telaprevir (VX-950) (Vertex). Further examples of protease inhibitors include substrate-based NS3 protease inhibitors (Attwood et al., Antiviral peptide derivatives, PCT WO 98/22496, 1998; Attwood et al., *Antiviral Chemistry and Chemotherapy* 1999, 10, 259-273; Attwood et al., Preparation and use of amino acid derivatives as anti-viral agents, German Patent Pub. DE 19914474; Tung et al., Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, Hepatitis C inhibitor peptide analogues, PCT WO 99/07734); Non-substrate-based NS3 protease inhibitors such as 2,4,6-trihydroxy-3-nitro-benzamide derivatives (Sudo K. et al., *Biochemical and Biophysical Research Communications*, 1997, 238, 643-647; Sudo K. et al., *Antiviral Chemistry and Chemotherapy*, 1998, 9, 186), including RD3-4082 and RD3-4078, the former substituted on the amide with a 14 carbon chain and the latter processing a para-phenoxyphenyl group; and Sch 68631, a phenanthrenequinone, an HCV protease inhibitor (Chu M. et al., *Tetrahedron Letters* 37:7229-7232, 1996).

SCH 351633, isolated from the fungus *Penicillium griseofulvum*, was identified as a protease inhibitor (Chu M. et al., *Bioorganic and Medicinal Chemistry Letters* 9:1949-1952). Eglin c, isolated from leech, is a potent inhibitor of several serine proteases such as *S. griseus* proteases A and B, α-chymotrypsin, chymase and subtilisin. Qasim M. A. et al., *Biochemistry* 36:1598-1607, 1997.

U.S. patents disclosing protease inhibitors for the treatment of HCV include, for example, U.S. Pat. No. 6,004,933 to Spruce et al., which discloses a class of cysteine protease inhibitors for inhibiting HCV endopeptidase 2; U.S. Pat. No. 5,990,276 to Zhang et al., which discloses synthetic inhibitors of hepatitis C virus NS3 protease; U.S. Pat. No. 5,538,865 to Reyes et a; WO 02/008251 to Corvas International, Inc, and U.S. Pat. No. 7,169,760, US2005/176648, WO 02/08187 and WO 02/008256 to Schering Corporation. HCV inhibitor tripeptides are disclosed in U.S. Pat. Nos. 6,534,523, 6,410,531, and 6,420,380 to Boehringer Ingelheim and WO 02/060926 to Bristol Myers Squibb. Diaryl peptides as NS3 serine protease inhibitors of HCV are disclosed in WO 02/48172 and U.S. Pat. No. 6,911,428 to Schering Corporation. Imidazoleidinones as NS3 serine protease inhibitors of HCV are disclosed in WO 02/08198 and U.S. Pat. No. 6,838,475 to Schering Corporation and WO 02/48157 and U.S. Pat. No. 6,727,366 to Bristol Myers Squibb. WO 98/17679 and U.S. Pat. No. 6,265,380 to Vertex Pharmaceuticals and WO 02/48116 and U.S. Pat. No. 6,653,295 to Bristol Myers Squibb also disclose HCV protease inhibitors. Further examples of HCV serine protease inhibitors are provided in U.S. Pat. No. 6,872,805 (Bristol-Myers Squibb); WO 2006000085 (Boehringer Ingelheim); U.S. Pat. No. 7,208,600 (Vertex); US 2006/0046956 (Schering-Plough); WO 2007/001406 (Chiron); US 2005/0153877; WO 2006/119061 (Merck); WO 00/09543 (Boehringer Ingelheim), U.S. Pat. No. 6,323,180 (Boehringer Ingelheim) WO 03/064456 (Boehringer Ingelheim), U.S. Pat. No. 6,642,204 (Boehringer Ingelheim), WO 03/064416 (Boehringer Ingelheim), U.S. Pat. No. 7,091,184 (Boehringer Ingelheim), WO 03/053349 (Bristol-Myers Squibb), U.S. Pat. No. 6,867,185, WO 03/099316 (Bristol-Myers Squibb), U.S. Pat. No. 6,869,964, WO 03/099274 (Bristol-Myers Squibb), U.S. Pat. No. 6,995,174, WO 2004/032827 (Bristol-Myers Squibb), U.S. Pat. No. 7,041,698, WO 2004/043339 and U.S. Pat. No. 6,878,722 (Bristol-Myers Squibb).

Thiazolidine derivatives which show relevant inhibition in a reverse-phase HPLC assay with an NS3/4A fusion protein and NS5A/5B substrate (Sudo K. et al., *Antiviral Research*, 1996, 32, 9-18), especially compound RD-1-6250, possessing a fused cinnamoyl moiety substituted with a long alkyl chain, RD4 6205 and RD4 6193;

Thiazolidines and benzanilides identified in Kakiuchi N. et al., J. EBS Letters 421, 217-220; Takeshita N. et al., *Analytical Biochemistry*, 1997, 247, 242-246;

A phenanthrenequinone possessing activity against protease in a SDS-PAGE and autoradiography assay isolated from the fermentation culture broth of *Streptomyces* sp., SCH 68631 (Chu M. et al., *Tetrahedron Letters*, 1996, 37, 7229-7232), and SCH 351633, isolated from the fungus *Penicillium griseofulvum*, which demonstrates activity in a scintillation proximity assay (Chu M. et al., *Bioorganic and Medicinal Chemistry Letters* 9, 1949-1952);

Helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

HCV polymerase inhibitors, including nucleoside and non-nucleoside polymerase inhibitors, such as ribavirin, viramidine, clemizole, filibuvir (PF-00868554), HCV POL, NM 283 (valopicitabine), MK-0608, 7-Fluoro-MK-0608, MK-3281, IDX-375, ABT-072, ABT-333, ANA598, BI 207127, GS 9190, PSI-6130, R1626, PSI-6206, PSI-35938, PSI-7851, PSI-7977, RG1479, RG7128, HCV-796 VCH-759 or VCH-916.

Gliotoxin (Ferrari R. et al., *Journal of Virology*, 1999, 73, 1649-1654), and the natural product cerulenin (Lohmann V. et al., *Virology*, 1998, 249, 108-118);

Interfering RNA (iRNA) based antivirals, including short interfering RNA (siRNA) based antivirals, such as Sirna-034 and others described in International Patent Publication Nos. WO/03/070750 and WO 2005/012525, and US Patent Publication No. US 2004/0209831.

Antisense phosphorothioate oligodeoxynucleotides (S-ODN) complementary to sequence stretches in the 5' non-coding region (NCR) of the virus (Alt M. et al., *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 1999, 181, 251-257);

Inhibitors of IRES-dependent translation (Ikeda N et al., Agent for the prevention and treatment of hepatitis C, Japanese Patent Pub. JP-08268890; Kai Y. et al., Prevention and treatment of viral diseases, Japanese Patent Pub. JP-10101591);

HCV entry inhibitors, such as celgosivir (MK-3253) (MIGENIX Inc.), SP-30 (Samaritan Pharmaceuticals), ITX4520 (iTherX), ITX5061 (iTherX), PRO-206 (Progenics Pharmaceuticals) and other entry inhibitors by Progenics Pharmaceuticals, e.g., as disclosed in U.S. Patent Publication No. 2006/0198855.

Ribozymes, such as nuclease-resistant ribozymes (Maccjak, D. J. et al., *Hepatology* 1999, 30, abstract 995) and those disclosed in U.S. Pat. No. 6,043,077 to Barber et al., and U.S. Pat. Nos. 5,869,253 and 5,610,054 to Draper et al.; and Nucleoside analogs have also been developed for the treatment of Flaviviridae infections.

In certain embodiments, the compounds provided herein can be administered in combination with any of the compounds described by Idenix Pharmaceuticals in International Publication Nos. WO 01/90121, WO 01/92282, WO 2004/003000, 2004/002422 and WO 2004/002999.

Other patent applications disclosing the use of certain nucleoside analogs that can be used as second agents to treat hepatitis C virus include: PCT/CA00/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002); PCT/US02/03086 (WO 02/057287; filed Jan. 18, 2002); U.S. Pat. Nos. 7,202,224; 7,125,855; 7,105,499 and 6,777,395 by Merck & Co., Inc.; PCT/EP01/09633 (WO 02/18404; published Aug. 21, 2001); US 2006/0040890; 2005/0038240; 2004/0121980; U.S. Pat. Nos. 6,846,810; 6,784,166 and 6,660,721 by Roche; PCT Publication Nos. WO 01/79246 (filed Apr. 13, 2001), WO 02/32920 (filed Oct. 18, 2001) and WO 02/48165; US 2005/0009737; US 2005/0009737; U.S. Pat. Nos. 7,094,770 and 6,927,291 by Pharmasset, Ltd.

Further compounds that can be used as second agents to treat hepatitis C virus are disclosed in PCT Publication No. WO 99/43691 to Emory University, entitled "2'-Fluoronucleosides". The use of certain 2'-fluoronucleosides to treat HCV is disclosed.

Other miscellaneous compounds that can be used as second agents include 1-amino-alkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056,961), and piperidenes (U.S. Pat. No. 5,830,905 to Diana et al.).

Exemplar); Second Therapeutic Agents for Treatment of HCV

In one embodiment, one or more compounds provided herein can be administered in combination or alternation with an anti-hepatitis C virus interferon, such as Intron A® (interferon alfa-2b) and Pegasys® (Peginterferon alfa-2a); Roferon A® (Recombinant interferon alfa-2a), Infergen® (consensus interferon; interferon alfacon-1), PEG-Intron® (pegylated interferon alfa-2b) and Pegasys® (pegylated interferon alfa-2a).

In one embodiment, the anti-hepatitis C virus interferon is infergen, IL-29 (PEG-Interferon lambda), R7025 (Maxy-alpha), Belerofon, Oral Interferon alpha, BLX-883 (Locteron), omega interferon, multiferon, medusa interferon, Albuferon or REBIF®.

In one embodiment, one or more compounds provided herein can be administered in combination or alternation with an anti-hepatitis C virus polymerase inhibitor, such as ribavirin, viramidine, HCV POL, NM 283 (valopicitabine), MK-0608, 7-Fluoro-MK-0608, PSI-6130, R1626, PSI-6206, PSI-35938, R1479, HCV-796 or R7128.

In certain embodiments, the one or more compounds provided herein can be administered in combination with ribavarin and an anti-hepatitis C virus interferon, such as Intron A® (interferon alfa-2b) and Pegasys® (Peginterferon alfa-2a); Roferon A® (Recombinant interferon alfa-2a), Infergen® (consensus interferon; interferon alfacon-1), PEG-Intron® (pegylated interferon alfa-2b) and Pegasys® (pegylated interferon alfa-2a).

In one embodiment, one or more compounds provided herein can be administered in combination or alternation with an anti-hepatitis C virus protease inhibitor such as ITMN-191, SCH 503034, VX950 (telaprevir) or Medivir HCV Protease Inhibitor.

In one embodiment, one or more compounds provided herein can be administered in combination or alternation with an anti-hepatitis C virus vaccine, such as TG4040, PeviPRO™, CGI-5005, HCV/MF59, GV1001, IC41 or INNO0101 (E1).

In one embodiment, one or more compounds provided herein can be administered in combination or alternation with an anti-hepatitis C virus monoclonal antibody, such as AB68 or XTL-6865 (formerly HepX-C); or an anti-hepatitis C virus polyclonal antibody, such as cicavir.

In one embodiment, one or more compounds provided herein can be administered in combination or alternation with an anti-hepatitis C virus immunomodulator, such as Zadaxin® (thymalfasin), NOV-205 or Oglufanide.

In one embodiment, one or more compounds provided herein can be administered in combination or alternation with Nexavar, doxorubicin, PI-88, amantadine, JBK-122, VGX-410C, MX-3253 (Ceglosivir), Suvus (BIVN-401 or virostat), PF-03491390 (formerly IDN-6556), G126270, UT-231B, DEBIO-025, EMZ702, ACH-0137171, MitoQ, ANA975, AVI-4065, Bavituxinab (Tarvacin), Alinia (nitrazoxanide) or PYN17.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); CDCl$_3$ (deuterated chloroform); AcOH (acetic acid); DCM (dichloromethane); DMSO (dimethylsulfoxide); DMSO-d$_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example 1

Preparation of Compound 3

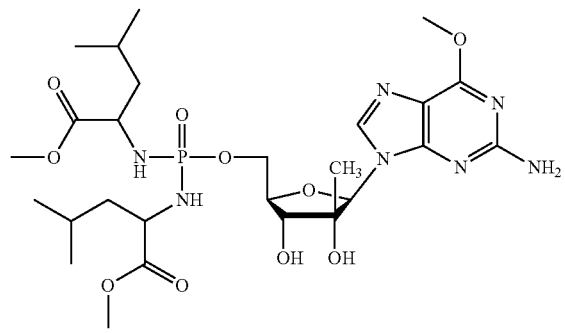

Synthesis of Compound 1:

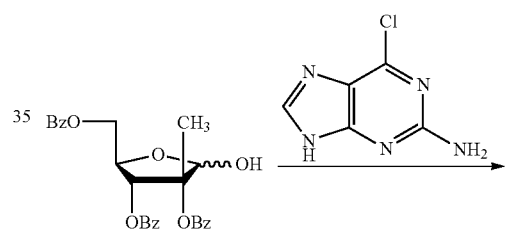

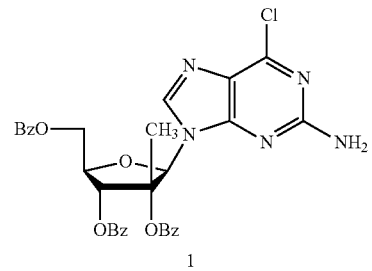

To a stirred suspension of 2-amino-6-chloro-purine (1.8 g, 1.2 eq.) in dry toluene (86 ml) was added N,O-bis(trimethylsilyl)acetamide (8.4 ml, 4 eq.). The mixture was stirred at 120° C. for 30 minutes (complete dissolution). 1,2,3,4-tetra-O-benzoyl-2-C-methyl-D-ribofuranose (5 g, 1 eq.) and trimethylsilyltriflate (3.9 ml, 2.5 eq.) were then added at room temperature and the reaction mixture was stirred at 120° C. for 3 hrs. The mixture was then diluted in DCM, washed twice with saturated NaHCO$_3$ solution and NaCl solution, and was purified by silica gel chromatography (Petroleum Ether/EtOAc) to give compound 1 in 45% yield. MS (ESI, EI$^+$) m/z=628 (MH$^+$).

Synthesis of Compound 2:

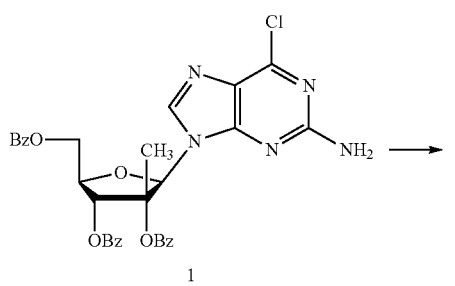

To a stirred solution of Compound 1 (17 g, 1 eq.) in MeOH (270 ml, 10 ml/mol) was added NaOCH$_3$ (64 g, 4.4 eq.) at room temperature. The reaction mixture was stirred at room temperature for 1 hour. AcOH was added to neutralize the mixture, the mixture was concentrated under reduced pressure, and purified by silica gel chromatography (C$_{18}$ column, H$_2$O/MeOH) to give Compound 2 in 74% yield. $^1$H NMR (DMSO-d$_6$, 400 MHz) δ (ppm): 0.77 (s, 3H), 3.67 (d, J=11.40 Hz, 1H), 3.77-3.86 (m, 2H), 3.94 (s, 3H), 3.98 (d, J=9.20 Hz, 1H), 5.26 (s, 2H), 5.60 (brs, 1H), 5.81 (s, 1H), 6.46 (s, 2H), 8.20 (s, 1H); MS (ESI, EI$^+$) m/z=312 (MH$^+$).

Synthesis of Compound 3:

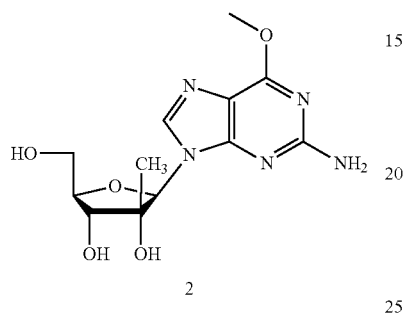

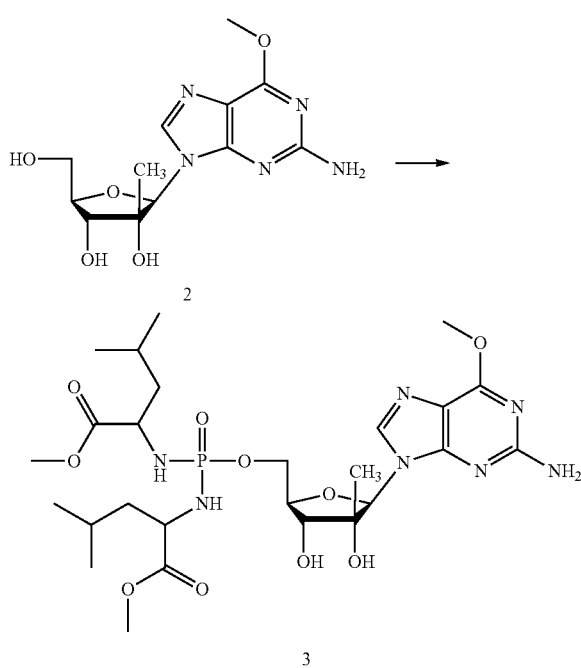

Compound 2 (200 mg, 1 eq.) was dissolved in PO(OEt)$_3$ (1 ml). POCl$_3$ (70 µl, 1.5 eq.) was then added drop wise to the mixture at 0° C. The reaction mixture was stirred at 0° C. for 30 min. L-Leucine methyl ester hydrochloride (548 mg, 5 eq.), PO(OEt)$_3$ in acetonitrile (600 µl/2.5 ml) and Et$_3$N (900 µl, 10 eq.) were then added at 0° C. and stirred for 30 minutes. The mixture was filtered, concentrated under reduced pressure and purified by silica gel chromatography (C$_{18}$ column, H$_2$O/MeOH) to yield Compound 3 as a white solid in 6% yield. $^1$H NMR (DMSO-d$_6$, 400 MHz) δ (ppm) 0.86 (t, J=5.93 Hz, 6H), 0.91 (dd, J=6.50 Hz and J=3.50 Hz, 6H), 0.98 (s, 3H), 1.29 (s, 3H), 1.43-1.52 (m, 4H), 1.68-1.74 (m, 2H), 3.50-3.71 (m, 7H), 3.80-3.89 (m, 2H), 4.05 (s, 3H), 4.14-4.18 (m, 1H), 4.28-4.30 (m, 1H), 4.34-4.38 (m, 2H), 5.97 (s, 1H), 7.98 (s, 1H). $^{31}$P NMR (DMSO-d$_6$, 162 MHz) δ (ppm) 13.96 (s, 1P). MS (ESI, EI$^+$) m/z=647 (MH$^+$).

Example 2

Preparation of Compound 4

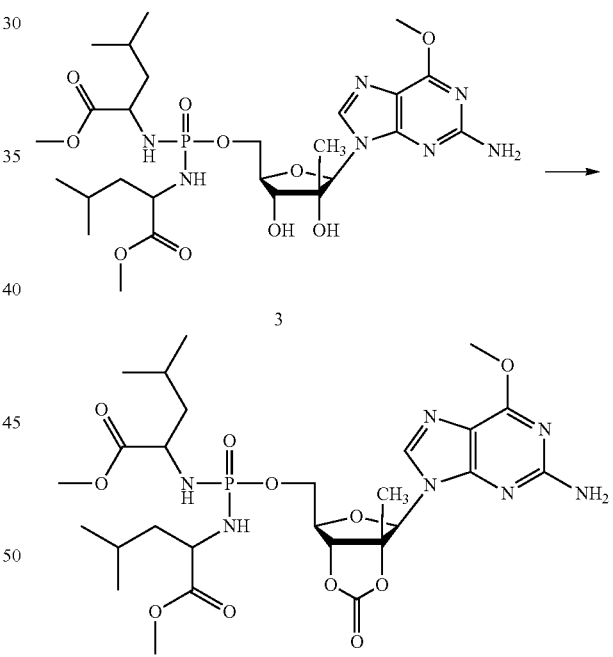

Carbonyldiimidazole (10 mg, 2 eq.) was poured onto a solution of Compound 3 (20 mg, 1 eq.) in anhydrous DMF (400 µl) at 0° C. The reaction mixture was stirred at 0° C. for 15 min and at room temperature for 2 hrs. The crude material was then purified by silica gel chromatography (C$_{18}$, H$_2$O/MeOH) to give Compound 4 as a white solid in 62% yield. MS (ESI, EI$^+$) m/z=673 (MH$^+$).

Example 3

Preparation of Compound 6

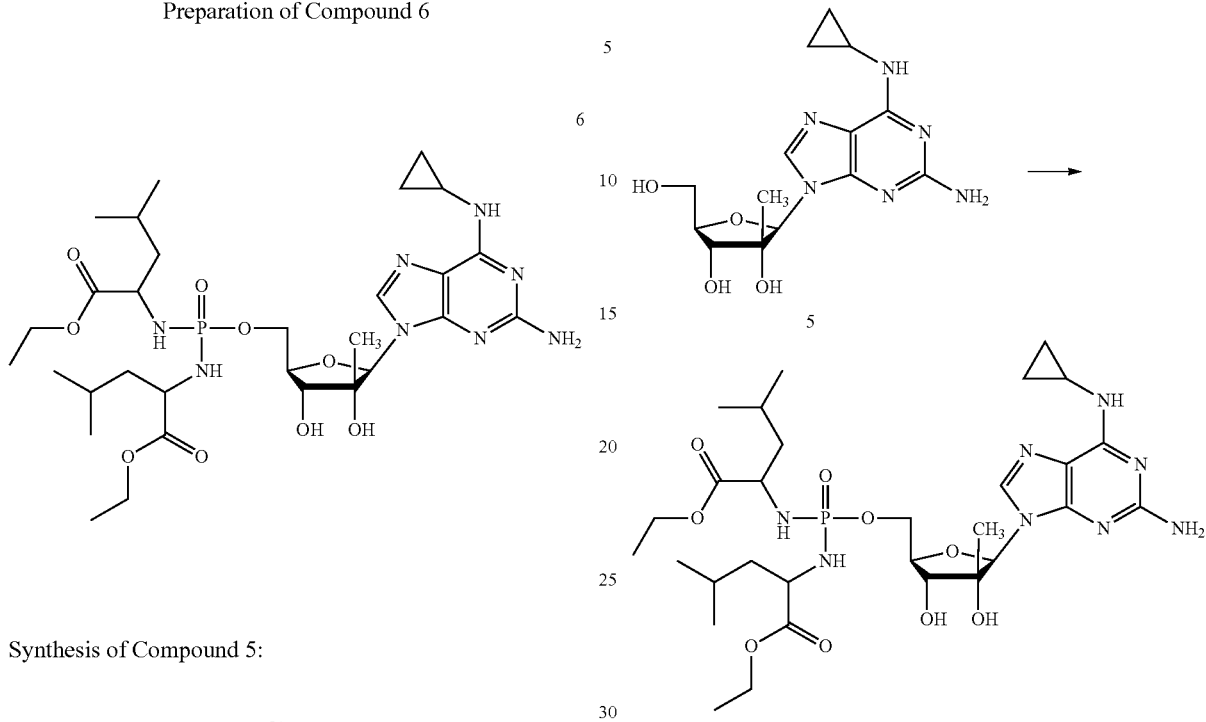

Synthesis of Compound 5:

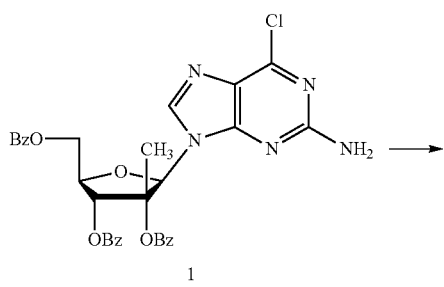

To a stirred solution of Compound 1 (1 g, 1 eq.) in EtOH (13 ml) was added cyclopropylamine (1.1 ml, 10 eq.) at room temperature. The reaction mixture was refluxed for 16 hours, cooled to room temperature and concentrated under reduced pressure. The crude material was used as is in the next step.

The crude product of the previous step (1 eq.) was dissolved in MeOH (32 ml). NaOMe (290 mg, 3.3 eq.) was then added to the mixture at room temperature. The reaction mixture was stirred at room temperature for 2 hrs, neutralized with AcOH to pH 7 and purified by silica gel chromatography ($C_{18}$ DCM/MeOH) to yield Compound 5 as a white solid in 93% yield. MS (ESI, EI$^+$) m/z=337 (MH$^+$).

Synthesis of Compound 6:

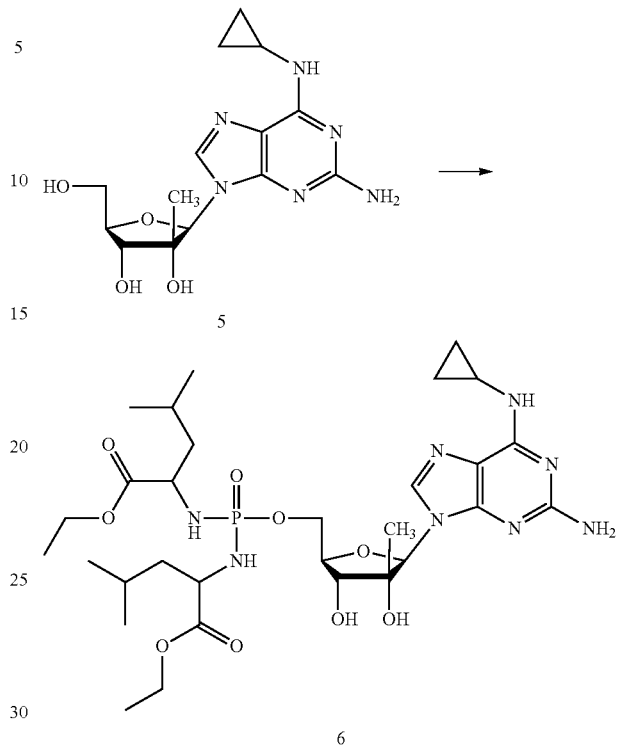

Compound 6 was prepared from Compound 5 (300 mg, 1 eq.) and L-Leucine ethyl ester hydrochloride following the procedure as described for Compound 3 to give Compound 6 as white powder in 23% yield. MS (ESI, EI$^+$) m/z=700 (MH$^+$).

Example 4

Preparation of Compound 7

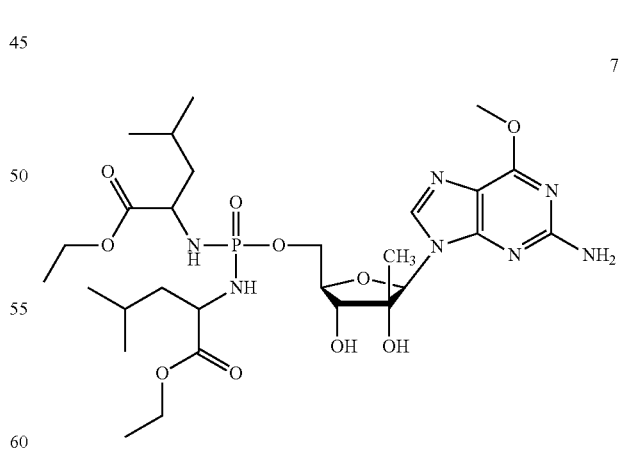

Compound 7 was synthesized from Compound 2 (100 mg, 1 eq.) and L-Leucine ethyl ester hydrochloride following the procedure as described for Compound 3 to give Compound 7 as white powder in 44% yield. $^1$H NMR (DMSO-d$_6$, 400 MHz) δ (ppm) 0.79-0.86 (m, 15H), 1.11-1.17 (m, 6H), 1.39 (m, 4H), 1.68 (m, 2H), 3.65 (m, 2H), 3.94 (s, 3H), 4.01-4.06

(m, 7H); 4.07 (m, 1H), 4.46-4.65 (m, 2H), 5.16 (s, 1H), 5.35 (s, 1H), 5.83 (s, 1H), 6.48 (s, 2H), 7.89 (s, 1H). $^{31}$P NMR (DMSO-d$_6$, 162 MHz) δ (ppm) 12.95 (s, 1P). MS (ESI, EI$^+$) m/z=675 (MH$^+$).

Example 5

Preparation of Compound 8

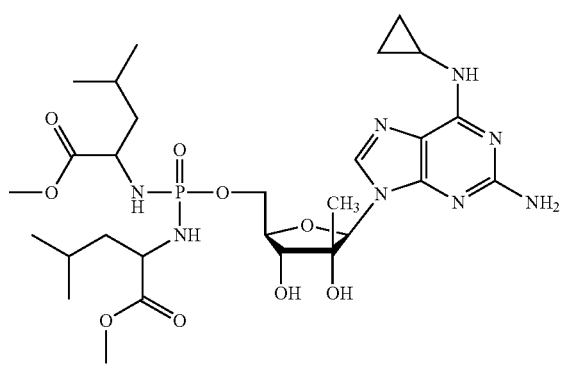

8

Compound 8 was prepared from Compound 5 (300 mg, 1 eq.) and L-Leucine methyl ester hydrochloride (810 mg, 5 eq.) following the procedure as described for Compound 3 to give Compound 8 as white powder in 9% yield. MS (ESI, EI$^+$) m/z=672 (MH$^+$)

Example 6

Preparation of Compound 9

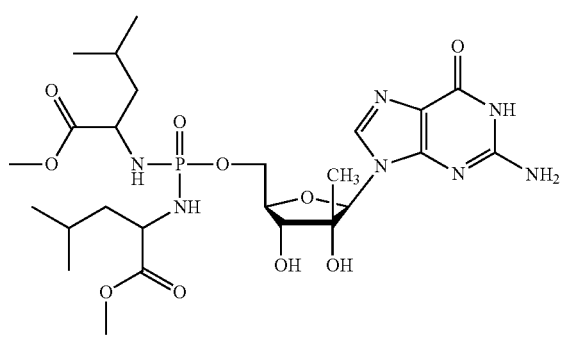

9

Compound 9 was synthesized from 2'-C-methylguanosine (300 mg, 1 eq.) and L-Leucine methyl ester hydrochloride (917 mg, 5 eq.) following the procedure as described for Compound 3 to give Compound 9 as white powder in 13% yield. MS (ESI, EI$^+$) m/z=632 (MH$^+$).

Example 7

Preparation of Compound 10

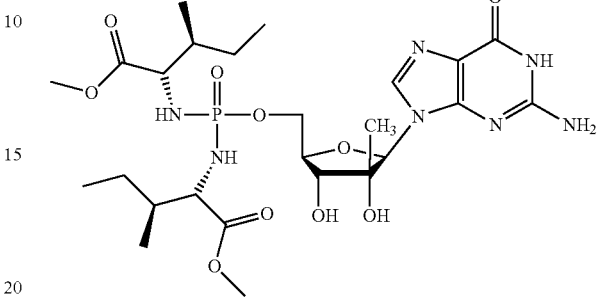

10

Compound 2 (1 ml, 1 eq.) was added to a stirred solution of L-isoleucine methyl ester hydrochloride (500 mg, 5 eq.) in Et$_3$N (800 µl, 10 eq.) and anhydrous THF (5 ml). The reaction mixture was stirred at room temperature under argon atmosphere for 2 hours. MeOH (10 ml) was added and the mixture was concentrated under reduced pressure. EtOAc and H$_2$O were added and the organic layer was separated, washed with H$_2$O, dried over Na$_2$SO$_4$, filtered and evaporated. The crude material was purified by semi-preparative chromatography to give Compound 10 as a white powder after lyophilization in 14% yield.

$^1$H NMR (DMSO-d$_6$, 400 MHz) δ (ppm). $^{31}$P NMR (DMSO-d$_6$, 162 MHz) δ (ppm). MS (ESI, EI$^+$) m/z=632 (MH$^+$).

Example 8

Preparation of Compound 11

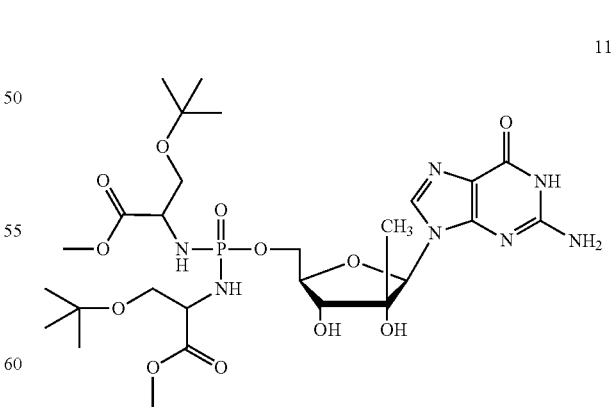

11

Compound 11 was prepared from Compound 2 (660 µl, 1 eq) following the procedure as described for Compound 10 to give Compound 11 as white powder in 3% yield. MS (ESI, EI$^+$) m/z=626 (MH$^+$).

Example 9

Preparation of Compound 12

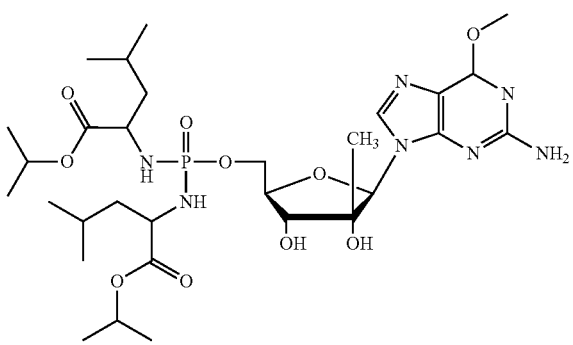

12

A mixture of L-Leucine (1 g, 1 eq.), SOCl$_2$ (1.7 ml, 3 eq.) in isopropanol (15 ml) was stirred under microwave irradiation at 100° C. for 1 hour. Solvent was then evaporated, the residue filtered and Et$_2$O was added to give L-Leucine isopropyl ester as a yellow oil in 71% yield. $^1$H NMR (DMSO-d$_6$, 400 MHz) δ (ppm): 0.88 (dd, J=6.41 Hz and J=2.14 Hz, 6H), 1.22 (t, J=6.03 Hz, 6H), 1.60-1.75 (m, 3 H), 3.82 (t, J=7.10 Hz, 1H), 4.97 (m, 1H), 8.61 (s, 2H).

Compound 12 was prepared from Compound 2 (200 mg, 1 eq.) and L-Leucine isopropyl ester (550 mg, 5 eq.) following the procedure as described for Compound 3 to give Compound 12 as white powder in 10% yield. MS (ESI, EI$^+$) m/z=703 (MH$^+$). $^{31}$P NMR (CDCl$_3$, 162 MHz) δ (ppm): 14.49 (s, 1P).

Example 10

Preparation of Compound 13

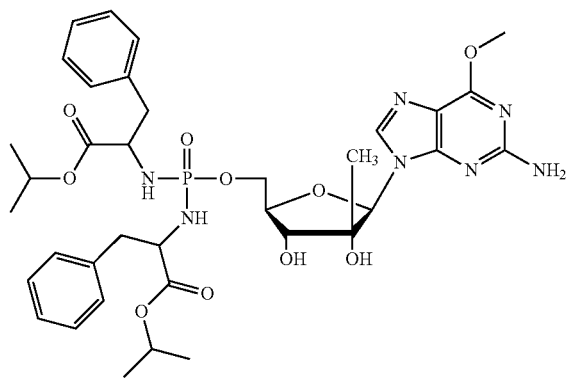

13

2-amino-3-phenyl-propionic acid isopropyl ester was prepared from phenylalanine following the procedure as described for Compound 12 to give a yellow oil in 80% yield. $^1$H NMR (DMSO-d$_6$, 400 MHz) δ (ppm): 0.98 (d, J=6.28 Hz, 3H), 1.12 (d, J=6.28 Hz, 3H), 3.02 (dd, J=13.78 Hz and J=8.50 Hz, 1H), 3.24 (dd, J=13.78 Hz and J=5.42 Hz, 1H), 4.12 (dd, J=8.69 Hz and J=5.42 Hz, 1H), 4.84 (m, 1H), 7.23-7.33 (m, 5H), 8.78 (s, 2H).

Compound 13 was prepared from Compound 2 (200 mg, 1 eq.) and 2-amino-3-phenyl-propionic acid isopropyl ester (660 mg, 5 eq.) following the procedure as described for Compound 3 to give Compound 13 as white powder in 20% yield. MS (ESI, EI$^+$) m/z=771 (MH$^+$). $^{31}$P NMR (CDCl$_3$, 162 MHz) δ (ppm): 13.88 (s, 1P).

Example 11

Preparation of Compound 14

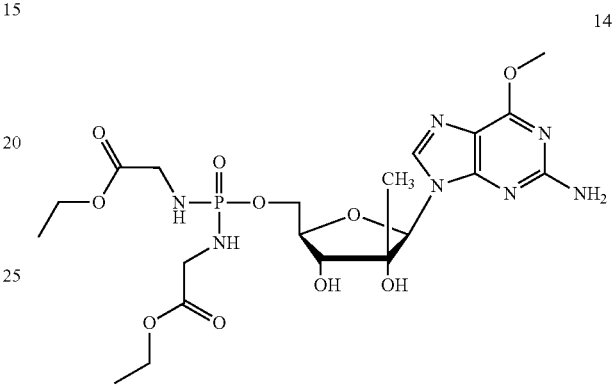

14

Compound 14 was prepared from Compound 2 (200 mg, 1 eq) and glycine ethyl ester hydrochloride (270 mg, 4 eq) following the procedure as described for Compound 3 to give Compound 14 as white powder in 8% yield. MS (ESI, EI$^+$) m/z=563 (MH$^+$). $^{31}$P NMR (DMSO-d$_6$, 162 MHz) δ (ppm): 15.16 (s, 1P).

Example 12

Preparation of Compound 15

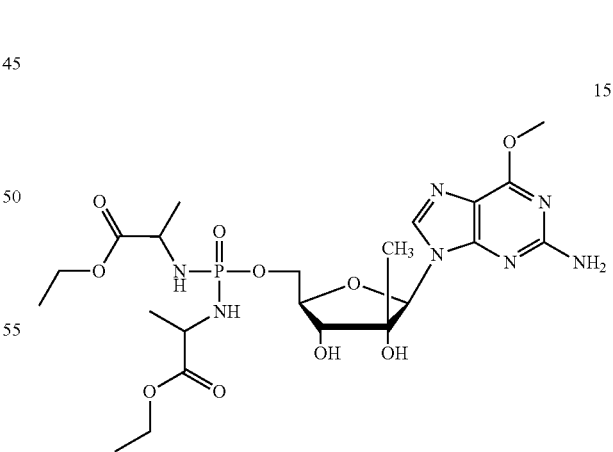

15

Compound 15 was prepared from Compound 2 (150 mg, 1 eq.) and L-alanine ethyl ester hydrochloride (370 mg, 5 eq.) following the procedure as described for Compound 3 to give Compound 15 as white powder in 20% yield. MS (ESI, EI$^+$) m/z=591 (MH$^+$). $^{31}$P NMR (DMSO-d$_6$, 162 MHz) δ (ppm): 12.75 (s, 1P).

Example 13

Preparation of Compound 16

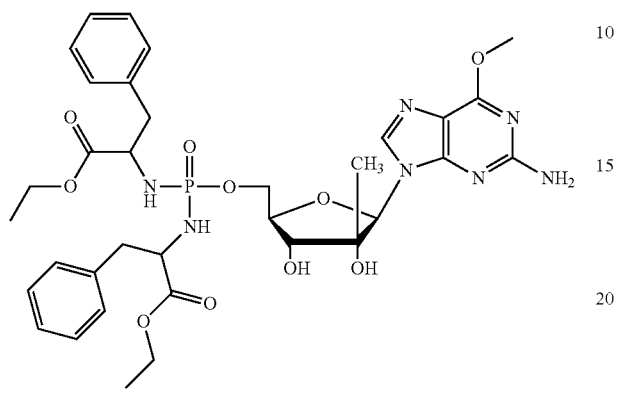

16

Compound 16 was prepared from Compound 2 (300 mg, 1 eq.) and L-phenylalanine ethyl ester hydrochloride (1.1 g, 5 eq.) following the procedure as described for Compound 3 to give Compound 16 as white powder in 40% yield. MS (ESI, EI$^+$) m/z=743 (MH$^+$). $^{31}$P NMR (DMSO-d$_6$, 162 MHz) δ (ppm): 12.12 (s, 1P).

Example 14

Preparation of Compound 17

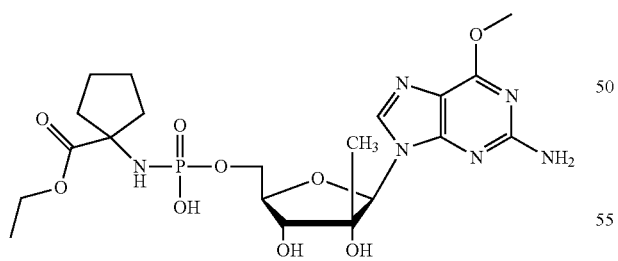

17

Compound 17 was prepared from Compound 2 (1 eq.) and 1-amino-cyclopentane carboxylic acid ethyl ester (5 eq.) following the procedure as described for Compound 3 to give Compound 17 as white powder in 20% yield. MS (ESI, EI$^+$) m/z=532 (MH$^+$). $^{31}$P NMR (DMSO-d$_6$, 162 MHz) δ (ppm): 0.45 (s, 1P).

Example 15

Preparation of Compound 21

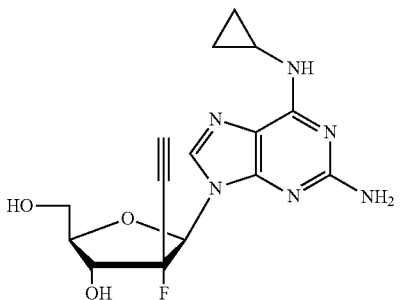

21

Synthesis of Compound 19:

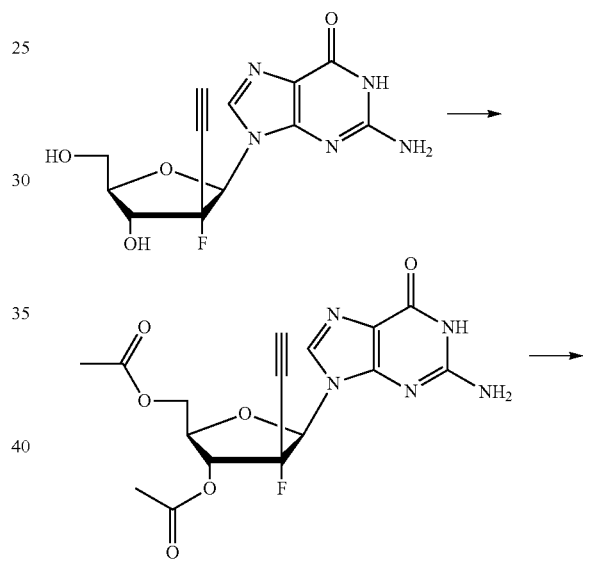

18

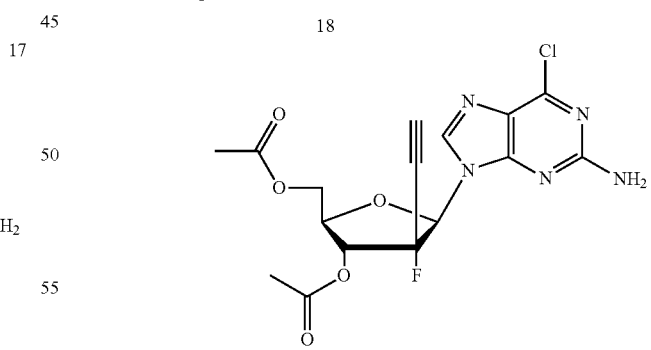

19

A mixture of 2-deoxy-2-fluoro-2-C-ethynyl-β-D-erythro-furanosyl-guanosine (4.5 g, 1 eq.) and acetyl chloride (2.6 ml, 2.5 eq.) in pyridine (180 ml) was stirred at room temperature for 45 minutes. Organics were separated, concentrated under reduced pressure and purified by silica gel chromatography (DCM/MeOH) to give Compound 18 as a beige solid in 55% yield. MS (ESI, EI$^+$) m/z=395 (MH$^+$).

A mixture of Compound 18 (3.2 g, 1 eq.) in POCl$_3$ (10 ml) was stirred under microwave irradiation at 120° C. for 30 minutes. DCM was added and the solution was poured slowly in cold NaHCO$_3$. Organics were separated, concentrated under reduced pressure and purified by silica gel chromatography (DCM/MeOH) to give Compound 19 as a beige solid in 35% yield. MS (ESI, EI$^+$) m/z=412 (MH$^+$).

Synthesis of Compound 21:

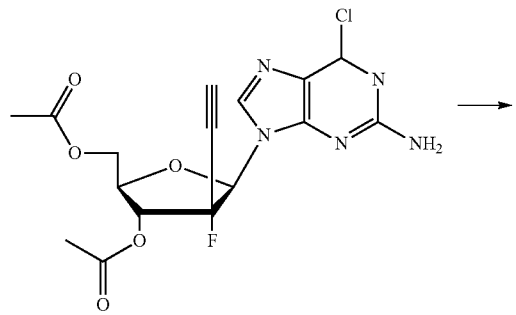

19

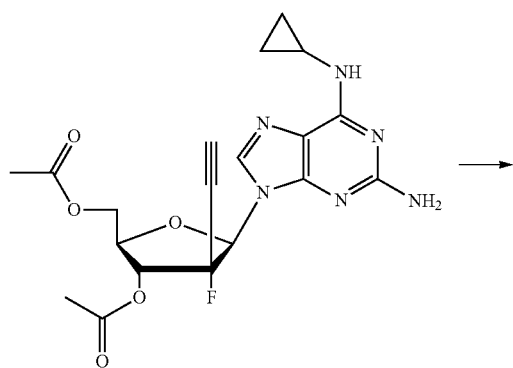

20

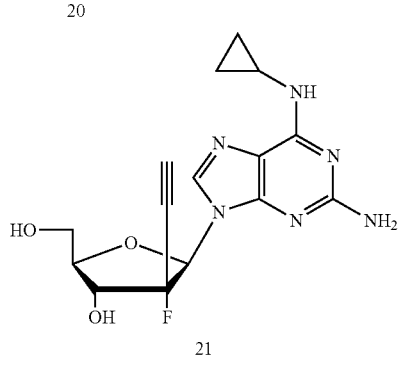

21

Compound 20 was synthesized from Compound 19 (500 mg, 1 eq.) and cyclopropylamine (850 µL, 10 eq.) following the procedure as described for Compound 5 to give Compound 20 as white powder in 80% yield. MS (ESI, EI$^+$) m/z=433 (MH$^+$).

Sodium methoxide (1.8 eq.) and Compound 20 (1 eq.) were mixed together and stirred at 50° C. for 40 minutes. The reaction mixture was purified by silica gel chromatography (MeOH/H$_2$O) to give Compound 21 as a beige solid in 20% yield. MS (ESI, EI$^+$) m/z=449 (MH$^+$).

Example 16

Preparation of Compound 22

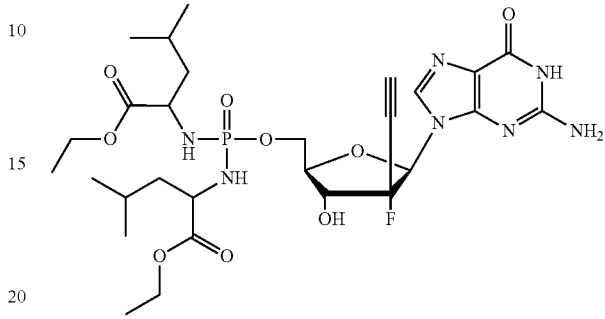

22

Compound 22 was synthesized from 2-deoxy-2-fluoro-2-C ethynyl-β-D-erythro-furanosyl-guanosine (1 eq.) and L-leucine ethyl ester hydrochloride (5 eq.) following the procedure as described for Compound 3 to give Compound 22 as white powder in 15% yield. MS (ESI, EI$^+$) m/z=672 (MH$^+$). $^{31}$P NMR (DMSO-d$_6$, 162 MHz) δ (ppm) 13.16 (s, 1P).

Example 17

Preparation of Compound 23

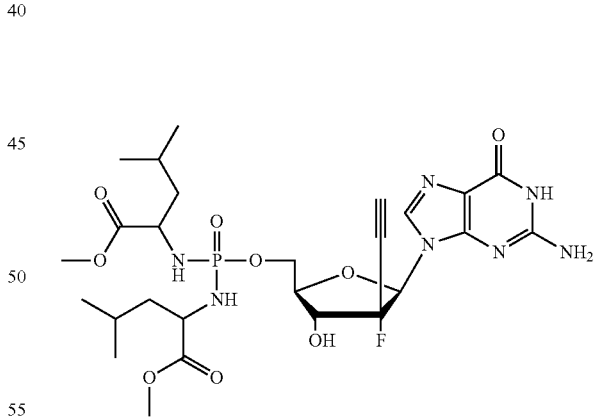

23

Compound 23 was synthesized from 2-deoxy-2-fluoro-2-C ethynyl-B-D-erythro-furanosyl-guanosine (1 eq.) and L-leucine methyl ester hydrochloride (5 eq.) following the procedure as described for Compound 3 to give compound 23 as white powder in 15% yield. MS (ESI, EI$^+$) m/z=644 (MH$^+$). $^{31}$P NMR (DMSO-d$_6$, 162 MHz) δ (ppm) 13.10 (s, 1P).

Example 18

Preparation of Compound 24

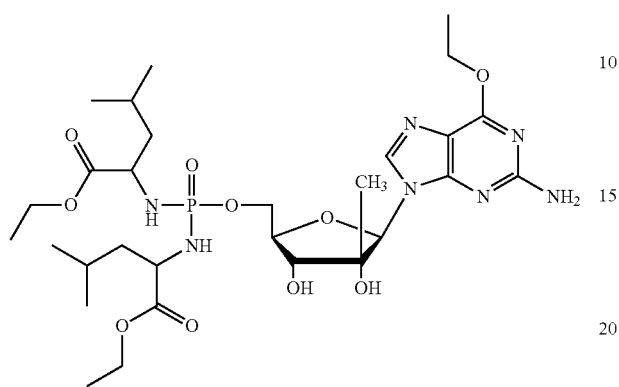

24

2-(2-amino-6-ethoxy-purin-9-yl)-5-hydroxymethyl-3-methyl-tetrahydrofuran-3,4-diol was prepared from Compound 1 (1 g, 1 eq.) and sodium ethoxide (433 mg, 4 eq.) following the procedure as described for Compound 2 to give the product as a pale yellow solid in 15% yield. MS (ESI, EI+) m/z=326 (MH+).

Compound 24 was synthesized from 2-(2-amino-6-ethoxy-purin-9-yl)-5-hydroxymethyl-3-methyl-tetrahydrofuran-3,4-diol (130 mg, 1 eq.) and L-leucine ethyl ester hydrochloride (391 mg, 5 eq.) following the procedure as described for Compound 3 to give Compound 24 as white powder in 40% yield. MS (ESI, EI+) m/z=689 (MH+). $^{31}$P NMR (DMSO-d$_6$, 162 MHz) δ (ppm) 12.94 (s, 1P).

Example 19

Preparation of Compound 25

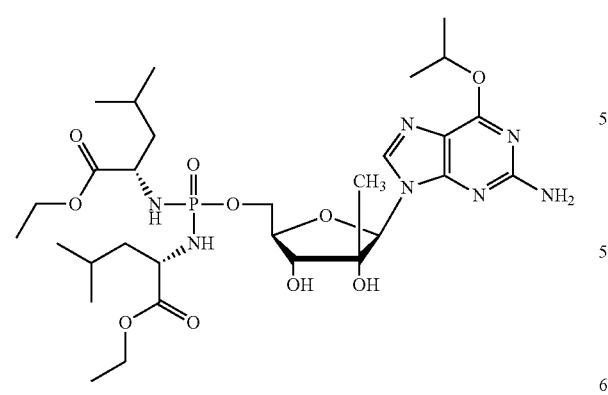

25

2-(2-amino-6-isopropoxy-purin-9-yl)-5-hydroxymethyl-3-methyl-tetrahydrofuran-3,4-diol was prepared from Compound 1 (1 g, 1 eq.) and isopropanol (200 ml, 4 eq.) following the procedure as described for Compound 2 to give the product as a beige solid in 20% yield. MS (ESI, EI+) m/z=340 (MH+).

Compound 25 was synthesized from 2-(2-amino-6-isopropoxy-purin-9-yl)-5-hydroxymethyl-3-methyl-tetrahydrofuran-3,4-diol (140 mg, 1 eq.) and L-leucine ethyl ester hydrochloride (404 mg, 5 eq.) following the procedure as described for Compound 3 to give Compound 25 as white powder in 25% yield. MS (ESI, EI+) m/z=702 (MH+). $^{31}$P NMR (DMSO-d$_6$, 162 MHz) δ (ppm) 12.92 (s, 1P).

Example 20

Preparation of Compound 26

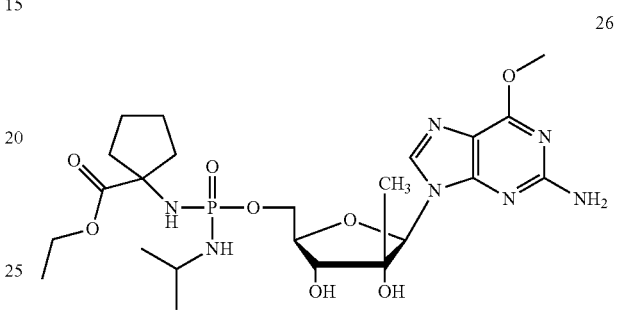

26

Compound 2 (115 mg, 1 eq.) was dissolved in PO(OEt)$_3$ (600 µl). POCl$_3$ (40 µl, 1.5 eq.) was then added dropwise to the mixture at 0° C. The reaction mixture was stirred at 0° C. for 30 min. 1-amino-cyclopentane carboxylic acid ethyl ester (358 mg, 5 eq.), PO(OEt)$_3$ in acetonitrile (200 µl/900 µl) and Et$_3$N (520 µl, 10 eq.) were then added at 0° C. and stirred for 30 min at the same temperature. Isopropylamine (157 µl, 5 eq.) was then added. The reaction mixture was stirred at room temperature for 1 hour. The mixture was filtered, concentrated under reduced pressure and purified by semi-preparative HPLC to provide Compound 26 as a beige solid in 10% yield. MS (ESI, EI+) m/z=572 (MH+); $^{31}$P NMR (DMSO-d$_6$, 162 MHz) δ (ppm) 13.22 (s, 1P).

Example 21

Preparation of Compound 27

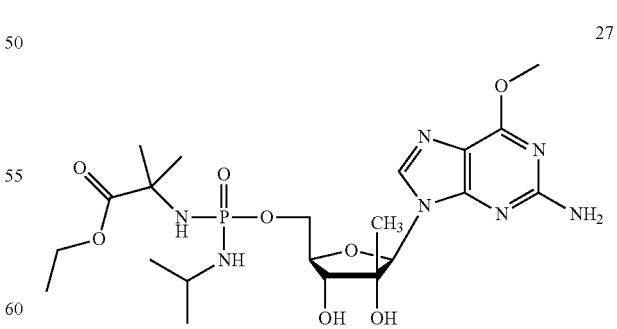

27

Compound 27 was prepared from Compound 2 (155 mg, 1 eq.) and 2-amino-2-methyl propionic acid ethyl ester (416 mg, 5 eq.) following the procedure as described for Compound 26 to give Compound 27 as white powder in 30% yield. MS (ESI, EI+) m/z=546 (MH+).

Example 22

Preparation of Compound 28

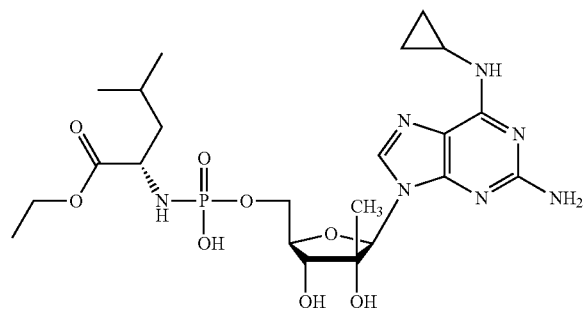

28

Compound 5 (300 mg, 1 eq) was dissolved in PO(OEt)$_3$ (3 ml). POCl$_3$ (150 µl, 1.5 eq.) was then added dropwise to the mixture at 0° C. The reaction mixture was stirred at 0° C. for 2 hrs. L-Leucine ethyl ester hydrochloride (174 mg, 1 eq.) and Et$_3$N (2 ml) were then added at 0° C. and stirred for 2 hrs at room temperature. The mixture was filtered, concentrated under reduced pressure and purified by silica gel chromatography (C$_{18}$ column, H$_2$O/MeOH) to yield Compound 28 as a white solid in 10% yield. $^{31}$P NMR (MeOD, 162 MHz) δ (ppm) 6.56 (s, 1P). MS (ESI, EI$^+$) m/z=558 (MH$^+$).

Example 23

Preparation of Compound 29

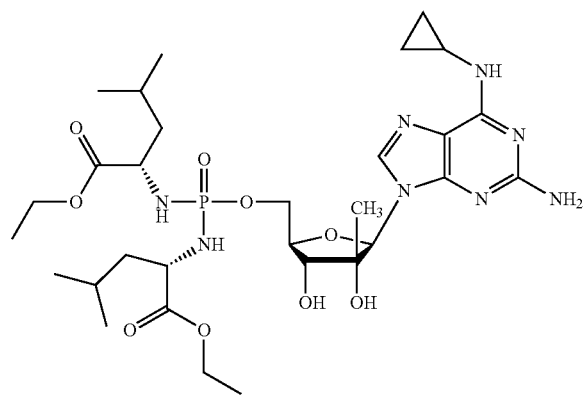

29

Compound 29 was synthesized from Compound 5 (300 mg, 1 eq.) and L-Valine ethyl ester hydrochloride (5 eq.) following the procedure as described for Compound 3 to give Compound 29 as a white powder in 10% yield. $^{31}$P NMR (MeOD, 162 MHz) δ (ppm) 15.22 (s, 1P). MS (ESI, EI$^+$) m/z=671 (MH$^+$).

Example 24

Preparation of Compound 30

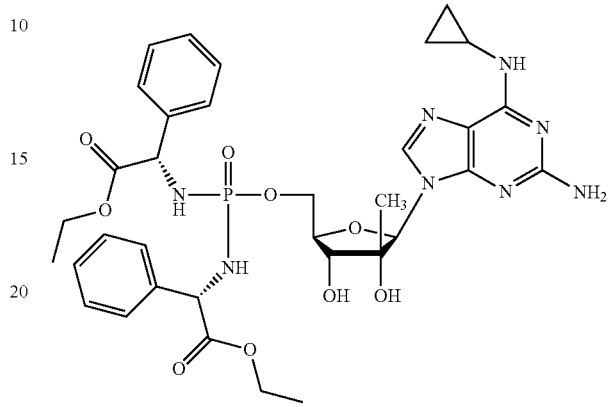

30

Compound 30 was synthesized from Compound 5 (300 mg, 1 eq.) and L-Phenylglycine ethyl ester hydrochloride (5 eq.) following the procedure as described for Compound 3 to give Compound 30 as a white powder in 8% yield. $^{31}$P NMR (MeOD, 162 MHz) δ (ppm) 13.62 (s, 1P). MS (ESI, EI$^+$) m/z=739 (MH$^+$).

Example 25

Preparation of Compound 31

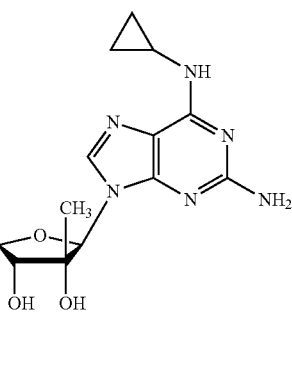

31

Compound 31 was synthesized from Compound 5 (200 mg, 1 eq.) and L-Alanine ethyl ester hydrochloride following the procedure as described for Compound 3 to give Compound 31 as a white powder in 15% yield. $^{31}$P NMR (MeOD, 162 MHz) δ (ppm) 14.02 (s, 1P). MS (ESI, EI$^+$) m/z=616 (MH$^+$).

Example 26

Preparation of Compound 32

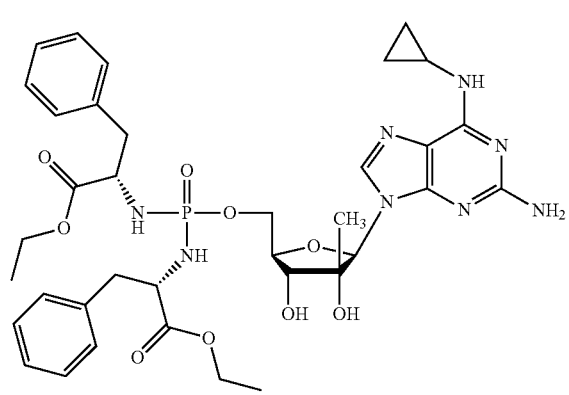

Compound 32 was synthesized from Compound 5 (200 mg, 1 eq.) and L-Phenylalanine ethyl ester hydrochloride following the procedure as described for Compound 3 to give Compound 32 as a white powder in 6% yield. $^{31}$P NMR (MeOD, 162 MHz) δ (ppm) 13.28 (s, 1P). MS (ESI, EI$^+$) m/z=786 (MH$^+$).

Example 27

Preparation of Compound 33

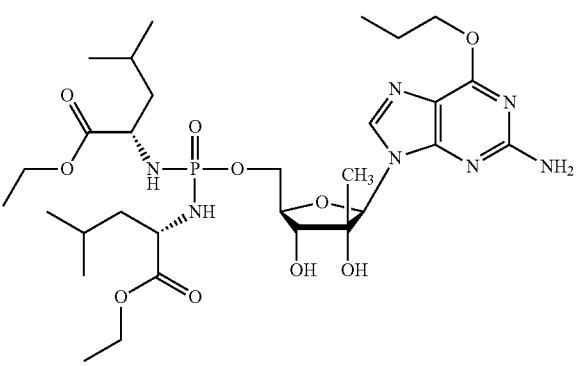

n-Propanol (20 ml) and NaH 60% (636 mg, 10 eq.) were mixed together at 80° C. for 15 minutes. Compound 1 (1 g, 1 eq.) was then added and the reaction mixture was refluxed for 1 hour. The mixture was purified by silica gel chromatography (DCM/MeOH) to give 2-(2-amino-6-propoxy-purin-9-yl)-5-hydroxymethyl-3-methyl-tetrahydrofuran-3,4-diol as a beige solid in 45% yield. MS (ESI, EI$^+$) m/z=340 (MH$^+$).

Compound 33 was synthesized from 2-(2-amino-6-propoxy-purin-9-yl)-5-hydroxymethyl-3-methyl-tetrahydrofuran-3,4-diol (349 mg, 1 eq.) and L-leucine ethyl ester hydrochloride (1 g, 5 eq.) following the procedure as described for Compound 3 to give Compound 33 as a white powder in 15% yield. $^{31}$P NMR (DMSO-d$_6$, 162 MHz) δ (ppm) 14.04 (s, 1P). MS (ESI, EI$^+$) m/z=703 (MH$^+$).

Example 28

Preparation of Compound 34

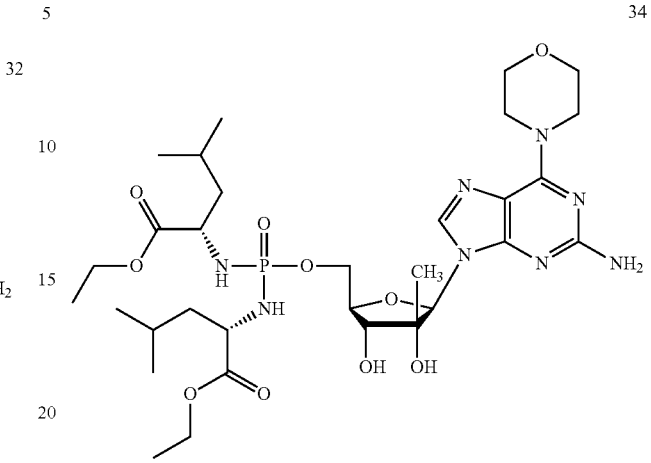

2-(2-amino-6-morpholino-9H-purin-9-yl)-5-(hydroxymethyl)-3-methyltetrahydrofuran-3,4-diol was synthesized from Compound 1 (1 g, 1 eq.) and morpholine (4 eq.) following the procedure as described for Compound 2 to give the product as a beige solid in 53% yield. MS (ESI, EI$^+$) m/z=367 (MH$^+$).

Compound 34 was synthesized from 2-(2-amino-6-morpholino-9H-purin-9-yl)-5-(hydroxymethyl)-3-methyltetrahydrofuran-3,4-diol (100 mg, 1 eq.) and L-leucine ethyl ester hydrochloride (300 mg, 5 eq.) following the procedure as described for Compound 3 to give Compound 34 as a white powder in 15% yield. $^{31}$P NMR (DMSO-d$_6$, 162 MHz) δ (ppm) 14.04 (s, 1P). MS (ESI, EI$^+$) m/z=729 (MH$^+$).

Example 29

Preparation of Compound 35

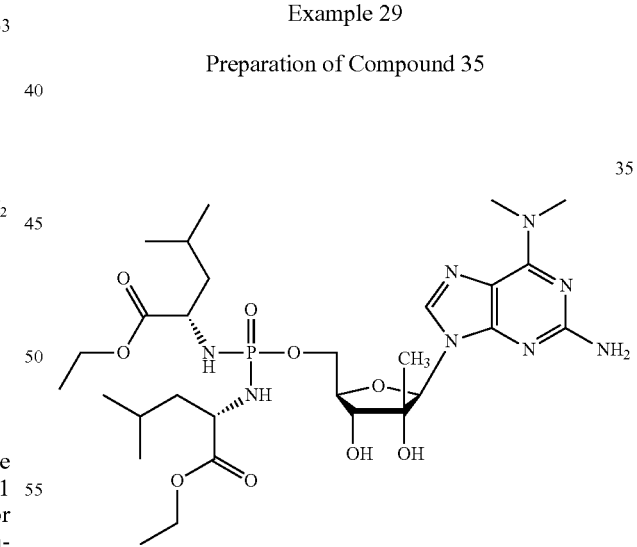

2-(2-amino-6-(dimethylamino)-9H-purin-9-yl)-5-(hydroxymethyl)-3-methyltetrahydrofuran-3,4-diol was synthesized from Compound 1 (1 g, 1 eq.) and dimethylamine (4 eq.) following the procedure as described for Compound 2 to give the product as a beige solid in 60% yield. MS (ESI, EI$^+$) m/z=325 (MH$^+$).

Compound 35 was synthesized from 2-(2-amino-6-(dimethylamino)-9H-purin-9-yl)-5-(hydroxymethyl)-3-methyltetrahydrofuran-3,4-diol (100 mg, 1 eq.) and L-leucine ethyl ester hydrochloride (300 mg, 5 eq.) following the procedure as described for Compound 3 to give Compound 35 as a white powder in 15% yield. $^{31}$P NMR (DMSO-$d_6$, 162 MHz) δ (ppm) 14.16 (s, 1P). MS (ESI, EI$^+$) m/z=687 (MH$^+$).

Example 30

Preparation of Compound 36

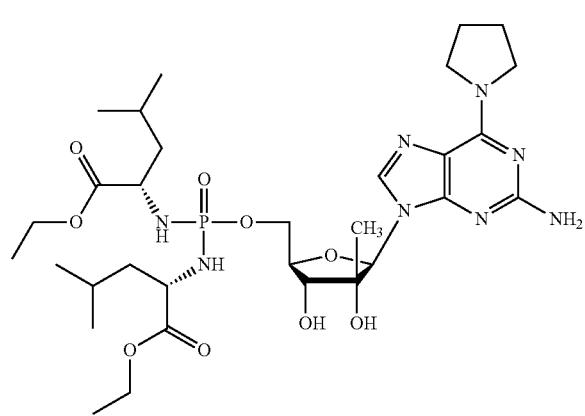

2-(2-amino-6-(pyrrolidin-1-yl)-9H-purin-9-yl)-5-(hydroxymethyl)-3-methyltetrahydrofuran-3,4-diol was synthesized from Compound 1 (1 g, 1 eq.) and pyrrolidine (10 eq.) following the procedure as described for Compound 2 to give the product as a beige solid in 60% yield. MS (ESI, EI$^+$) m/z=351 (MH$^{3o}$)

Compound 36 was synthesized from 2-(2-amino-6-(pyrrolidin-1-yl)-9H-purin-9-yl)-5-(hydroxymethyl)-3-methyltetrahydrofuran-3,4-diol (200 mg, 1 eq.) and L-leucine ethyl ester hydrochloride (558 mg, 5 eq.) following the procedure as described for Compound 3 to give Compound 36 as a white powder in 32% yield. $^{31}$P NMR (DMSO-$d_6$, 162 MHz) δ (ppm) 14.11 (s, 1P). MS (ESI, EI$^+$) m/z=714 (MH$^+$).

Example 31

Preparation of Compound 37

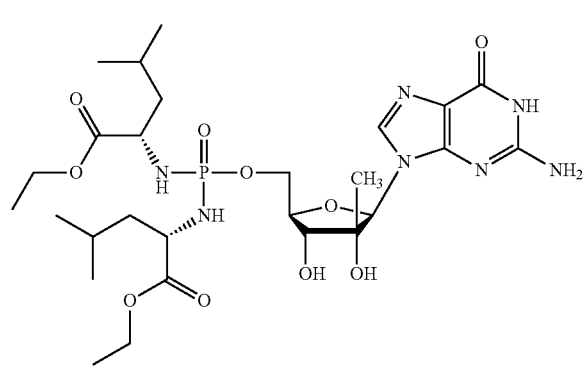

Compound 37 was prepared from 2'-C-methylguanosine (200 mg, 1 eq.) and L-Leucine ethyl ester hydrochloride (655 mg, 5 eq.) following the procedure as described for Compound 3 to give Compound 27 as a white powder in 45% yield. $^{31}$P NMR (DMSO-$d_6$, 162 MHz) δ (ppm) 17.70 (s, 1P). MS (ESI, EI$^+$) m/z=660 (MH$^+$).

Example 32

Preparation of Compound 38

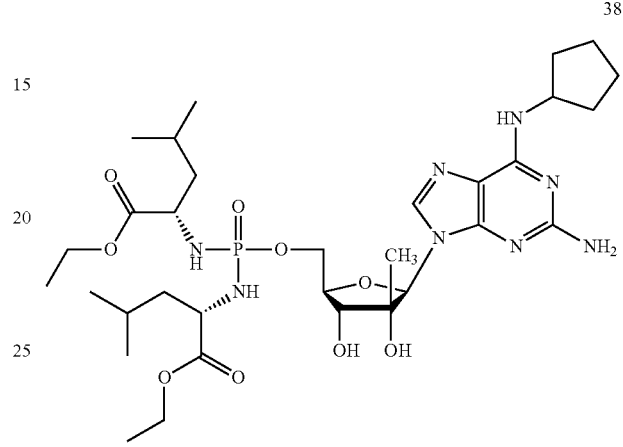

2-(2-amino-6-(cyclopentylamino)-9H-purin-9-yl)-5-(hydroxymethyl)-3-methyltetrahydrofuran-3,4-diol was synthesized from Compound 1 (1 g, 1 eq.) and cyclopentylamine (10 eq.) following the procedure as described for Compound 2 to give the product as a beige solid in 60% yield. MS (ESI, EI$^+$) m/z=365 (MH$^+$).

Compound 38 was synthesized from 2-(2-amino-6-(cyclopentylamino)-9H-purin-9-yl)-5-(hydroxymethyl)-3-methyltetrahydrofuran-3,4-diol (200 mg, 1 eq.) and L-leucine ethyl ester hydrochloride (538 mg, 5 eq.) following the procedure as described for Compound 3 to give Compound 38 as a white powder in 35% yield. $^{31}$P NMR (DMSO-$d_6$, 162 MHz) δ (ppm) 13.93 (s, 1P). MS (ESI, EI$^+$) m/z=727 (MH$^+$).

Example 33

Preparation of Compound 39

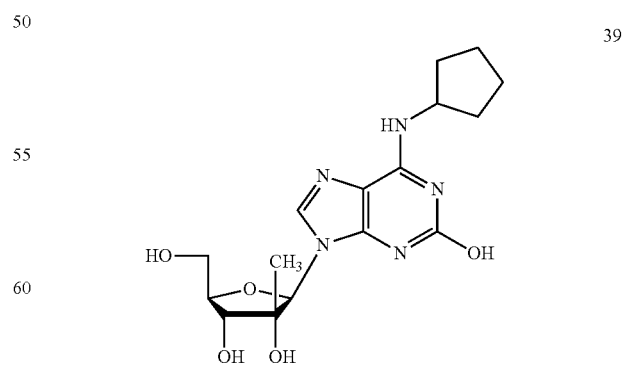

2-(6-(cyclopentylamino)-2-hydroxy-9H-purin-9-yl)-5-(hydroxymethyl)-3-methyltetrahydrofuran-3,4-diol: t-Butyl nitrile (1.6 ml, 4.2 eq.) was added at 0° C. to a stirred solution of Compound 1 (2 g, 1 eq.) in dioxane (60 ml) and H$_2$O (40 ml). The reaction mixture was stirred at room temperature for 16 hours, lyophilisated and used as is in the next step. MS (ESI, EI$^+$) m/z=313 (MH$^+$).

Compound 39 was synthesized from 2-(6-(cyclopentylamino)-2-hydroxy-9H-purin-9-yl)-5-(hydroxymethyl)-3-methyltetrahydrofuran-3,4-diol (500 mg, 1 eq.) and cyclopentylamine (75 mg, 1.1 eq.) following the procedure as described for Compound 2 to give the product as a beige solid in 23% yield. MS (ESI, EI$^+$) m/z=366 (MH$^+$).

Example 34

Preparation of Compound 40

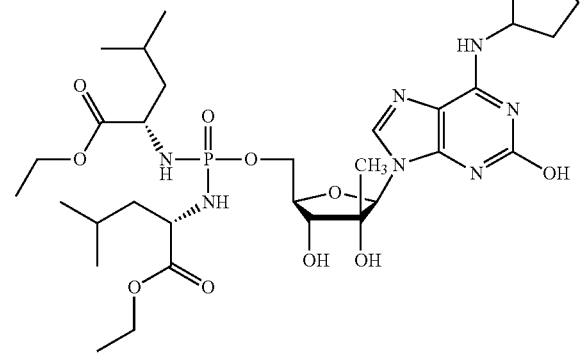

40

Compound 40 was synthesized from Compound 39 (67.1 mg, 1 eq.) and L-leucine ethyl ester hydrochloride (90 mg, 2.5 eq.) following the procedure as described for Compound 3 to give the product as white powder in 10% yield. $^{31}$P NMR (CD$_3$OD, 162 MHz) δ (ppm) 9.14 (s, 1P). MS (ESI, EI$^+$) m/z=728 (MH$^+$).

Example 35

Preparation of Compound 41

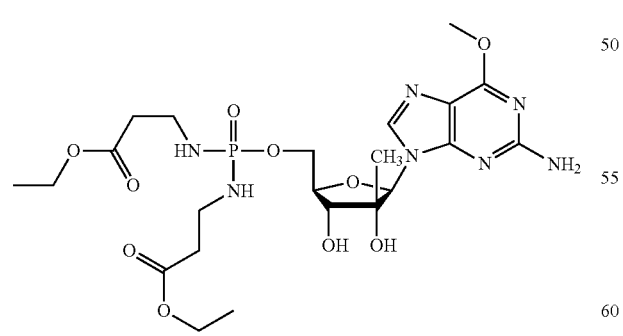

41

Compound 41 was synthesized from Compound 2 (200 mg, 1 eq.) and β-Alanine hydrochloride (246 mg, 2.5 eq.) following the procedure as described for Compound 3 to give the product as a white powder in 80% yield. MS (ESI, EI$^+$) m/z=590 (MH$^+$).

Example 36

Preparation of Compound 42

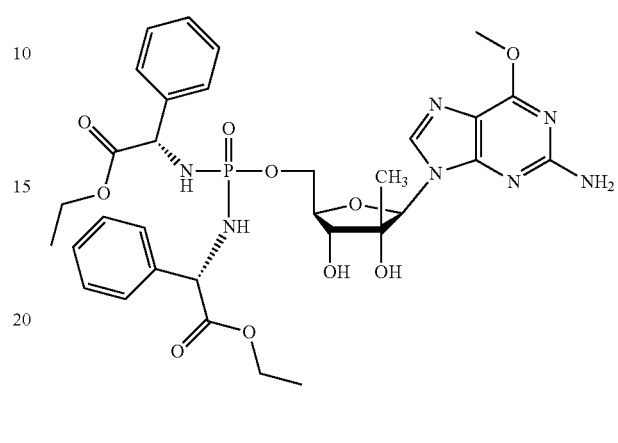

42

Compound 42 was synthesized from Compound 2 (200 mg, 1 eq.) and L-Phenylglycine ethyl ester hydrochloride (345 mg, 3 eq.) following the procedure as described for Compound 3 to give the product as a white powder in 80% yield. $^{31}$P NMR (MeOD, 162 MHz) δ (ppm) 13.64 (s, 1P). MS (ESI, EI$^+$) m/z=714 (MH$^+$).

Example 37

Preparation of Compound 43

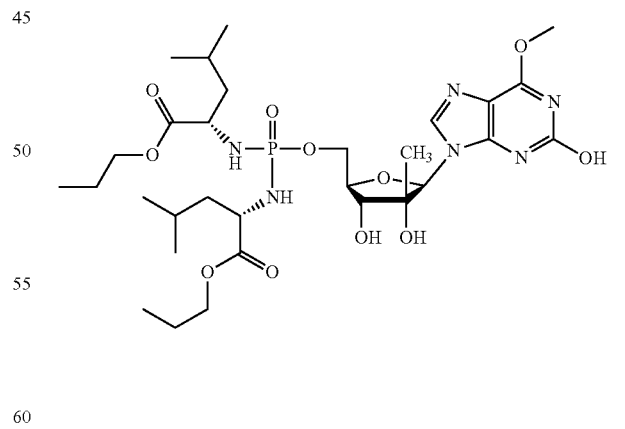

43

Compound 43 was synthesized from Compound 2 (200 mg, 1 eq.) and L-Leucine propyl ester hydrochloride (404 mg, 3 eq.) following the procedure as described for Compound 3 to give the product as a white powder in 10% yield. $^{31}$P NMR (CD$_3$OD, 162 MHz) δ (ppm) 13.98 (s, 1P). MS (ESI, EI$^+$) m/z=702 (MH$^+$).

Example 38

Preparation of Compound 44

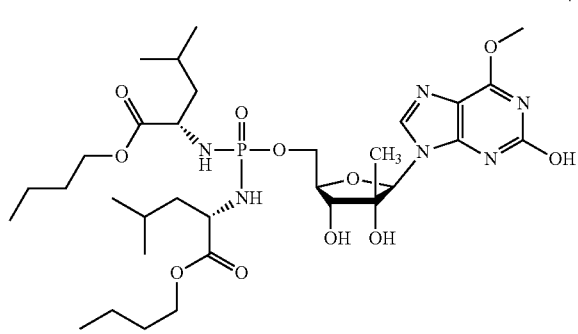

44

Compound 44 was synthesized from Compound 2 (200 mg, 1 eq.) and L-Leucine butyl ester hydrochloride (431 mg, 3 eq.) following the procedure as described for Compound 3 to give the product as a white powder in 8% yield. $^{31}$P NMR (CD$_3$OD, 162 MHz) δ (ppm) 13.98 (s, 1P). MS (ESI, EI$^+$) m/z=730 (MH$^+$).

Example 39

Preparation of Compound 45

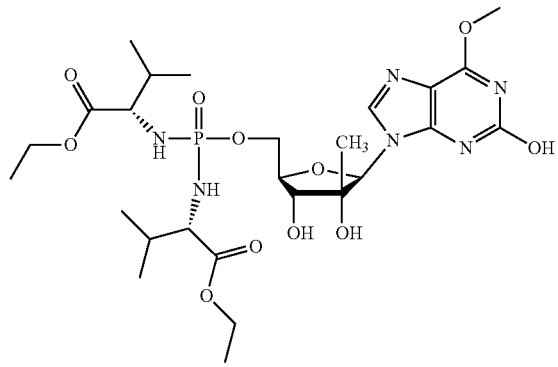

45

Compound 45 was synthesized from Compound 2 (200 mg, 1 eq.) and L-Valine ethyl ester hydrochloride (350 mg, 3 eq.) following the procedure as described for Compound 3 to give the product as a white powder in 15% yield. $^{31}$P NMR (CD$_3$OD, 162 MHz) δ (ppm) 15.22 (s, 1P). MS (ESI, EI$^+$) m/z=647 (MH$^+$).

Example 40

Preparation of Compound 46

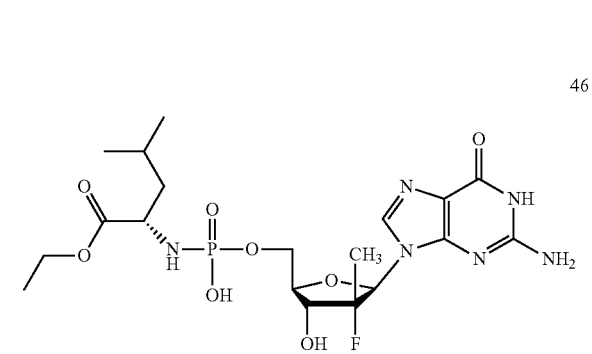

46

Compound 46 was synthesized from 2-deoxy-2-fluoro-2-C-methyl-β-D-erythro-furanosyl-guanosine (65 mg, 1 eq.) and L-Leucine ethyl ester hydrochloride (350 mg, 3 eq.) following the procedure as described for Compound 3 to give the product as a white powder in 45% yield. $^{31}$P NMR (DMSO-d$_6$, 162 MHz) δ (ppm) 13.07 (s, 1P). MS (ESI, EI$^+$) m/z=662 (MH$^+$).

Example 41

Preparation of Compound 47

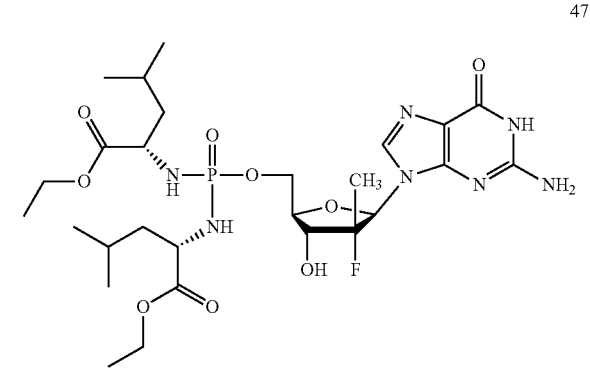

47

Compound 47 was synthesized from compound 46 (1 eq.) and L-Leucine ethyl ester hydrochloride (5 eq.) following the procedure as described for Compound 3 to give the product as a white powder in 20% yield. MS (ESI, EI$^+$) m/z=602 (MH$^+$).

Example 42

Preparation of Compound 48

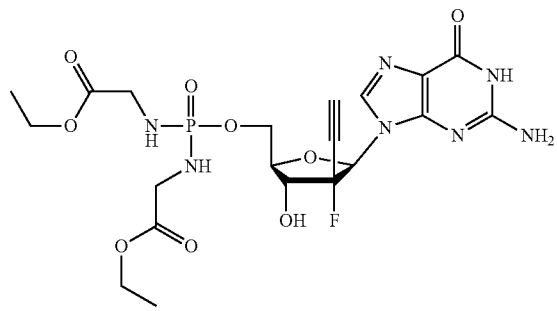

48

Compound 48 was synthesized from 2-deoxy-2-fluoro-2-C ethynyl-B-D-erythro-furanosyl-guanosine (1 eq.) and L-glycine ethyl ester hydrochloride (5 eq.) following the procedure as described for Compound 3 to give the product as a white powder in 25% yield. MS (ESI, EI$^+$) m/z=560 (MH$^+$).

Example 43

Preparation of Compound 49

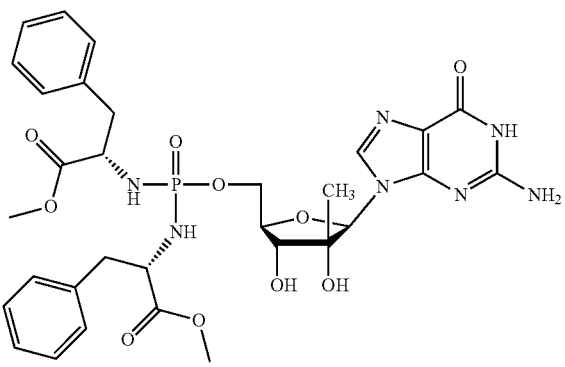

49

Compound 49 was synthesized from 2'-C-methylguanosine (200 mg, 1 eq.) and L-Phenylalanine methyl ester hydrochloride (5 eq.) following the procedure as described for Compound 3 to give the product as a white powder in 10% yield. $^{31}$P NMR (DMSO-d$_6$, 162 MHz) δ (ppm) 12.10 (s, 1P). MS (ESI, EI$^+$) m/z=700 (MH$^+$).

Example 44

Preparation of Compound 50

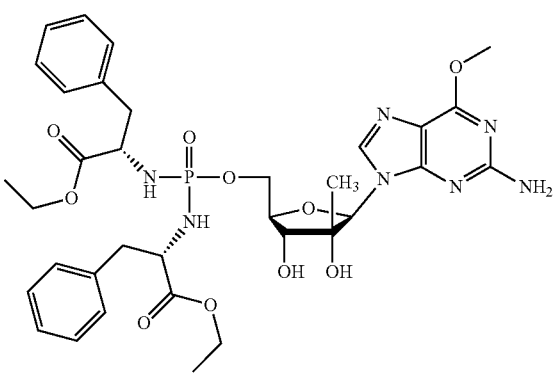

50

Compound 50 was synthesized from Compound 2 (200 mg, 1 eq.) and L-Phenylalanine ethyl ester hydrochloride (5 eq.) following the procedure as described for Compound 3 to give the product as a white powder in 22% yield. MS (ESI, EI$^+$) m/z=745 (MH$^+$).

Example 45

Preparation of Compound 51

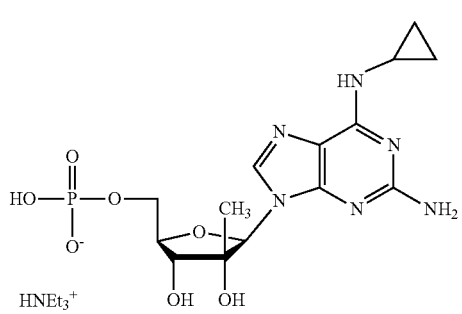

51

A solution of PO(OEt)$_3$/POCl$_3$ (255 µl: 2 ml/200 µl) was added to Compound 5 (31.1 mg, 1 eq.) at 0° C. The mixture was stirred at 0° C. under nitrogen for 30 minutes and purified over a SEPHADEX® column (TEAB 1M, pH<7.5) to give Compound 51 as a white solid in 65% yield. $^{31}$P NMR (D$_2$O, 162 MHz) δ (ppm): 0.74 (s, 1P).

Example 46

Preparation of Compound 52

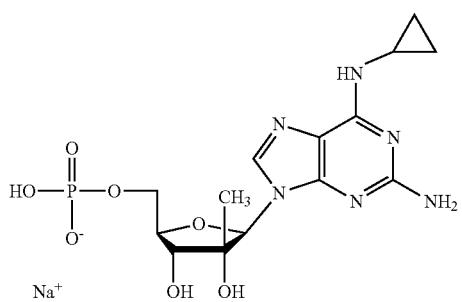

Compound 52 was prepared from Compound 51 using sodium exchange resin (Dowex) in 60% yield. $^{31}$P NMR (D$_2$O, 162 MHz) δ (ppm): 0.90 (s, 1P).

Example 47

Preparation of Compound 53

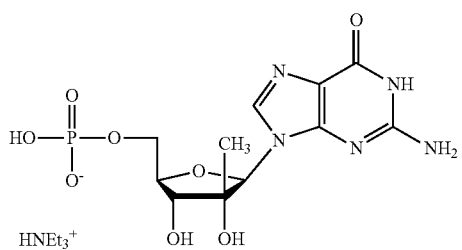

Compound 53 was prepared from 2-C-methylguanosine (476 mg, 1 eq.) following the procedure as described for Compound 51 to give the product as a white powder in 63% yield. $^{31}$P NMR (D$_2$O, 162 MHz) δ (ppm): 0.85 (s, 1P).

Example 48

Preparation of Compound 54

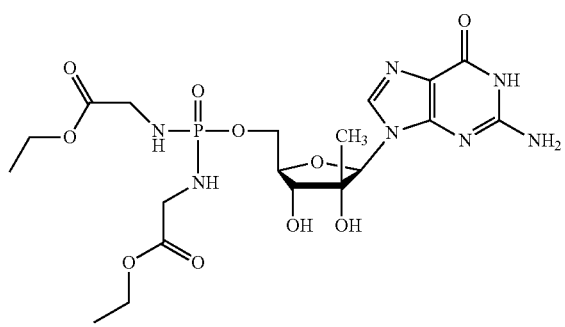

Compound 53 (30 mg, 1 eq.) and L-glycine ethyl ester hydrochloride (60 mg, 7 eq.) were co-evaporated twice with anhydrous pyridine. Pyridine (2.3 ml) was then added and the mixture was stirred at 60° C. for 30 minutes. A solution of PPh$_3$ (110 mg) and aldrithiol (93 mg, 7 eq) in pyridine (1 ml) was stirred at room temperature for 30 minutes and was added to the cooled mixture. The reaction mixture was stirred at 60° C., DCM was added, organics were separated, concentrated under reduced pressure and purified by silica gel chromatography (DCM/MeOH) to give compound 54 as a white powder in 35% yield. MS (ESI, EI$^+$) m/z=548 (MH$^+$).

Example 49

HCV Replicon Assay

Huh-7 cells containing HCV Con1 subgenomic replicon (GS4.1 cells), (C. Seeger; Fox Chase University, Philadelphia, Pa., USA), are grown in Dulbecco's Modified Eagle Medium (DMEM) supplemented with 10% fetal bovine serum (FBS), 2 mM L-glutamine, 110 mg/L sodium pyruvate, 1× non-essential amino acids, 100 U/mL penicillin-streptomycin and 0.5 mg/mL G418 (Invitrogen). For dose-response testing, the cells are seeded in 96-well plates at 7.5×10$^3$ cells/well in a volume of 50 μL and incubated at 37° C./5% CO$_2$. Three hours after plating, 50 μL of ten 2-fold serial dilutions of compounds (highest concentration, 75 μM) are added and cell cultures were incubated at 37° C./5% CO$_2$ in the presence of 0.5% DMSO. Alternatively, compounds are tested at a single concentration of 15 μM. In all cases, Huh-7 cells lacking the HCV replicon served as negative control. The cells are incubated in the presence of compounds for 72 hours after which they were monitored for expression of the NS4A protein by enzyme-linked immunosorbent assay (ELISA). For this, the plates were then fixed for 1 min with 1:1 acetone:methanol, washed twice with phosphate-buffered saline (PBS), 0.1% Tween 20, blocked for 1 hour at room temperature with TNE buffer containing 10% FBS and then incubated for 2 h at 37° C. with the anti-NS4A mouse monoclonal antibody A-236 (ViroGen) diluted in the same buffer. After washing three times with PBS, 0.1% Tween 20, the cells are incubated 1 hour at 37° C. with anti-mouse immunoglobulin G-peroxidase conjugate in TNE, 10% FBS. After washing as described above, the reaction is developed with O-phenylenediamine (Zymed). The reaction is stopped after 30 minutes with 2 NH$_2$SO$_4$ and the absorbance is read at 492 nm using a Sunrise Tecan spectrophotometer. EC$_{50}$ values are determined from the % inhibition versus concentration data using a sigmoidal non-linear regression analysis based on four parameters with Tecan Magellan software. When screening at a single concentration, the results are expressed as % inhibition at 15 μM. For cytotoxicity evaluation, GS4.1 cells are treated with compounds as described above and cellular viability was monitored using a Cell Titer 96 AQ$_{ueous}$ One Solution Cell Proliferation Assay (Promega). CC$_{50}$ values are determined from the % cytotoxicity versus concentration data with Tecan Magellan software as described above.

Compounds presented in the table below were assayed according to the replicon assay described above.

| Compound Reference | Structure | HCV Replicon | |
|---|---|---|---|
| | | EC$_{50}$ (µM) | CC$_{50}$ (µM) |
| NUCLEOSIDE PARENT: | 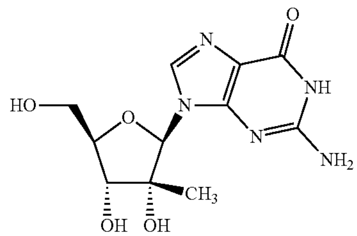 [SMILES: C[C@@]1(O)[C@H](O)[C@@H](CO)O[C@H]1n1cnc2c(=O)[nH]c(N)nc21] | ++ | + |
| Compound 54: | 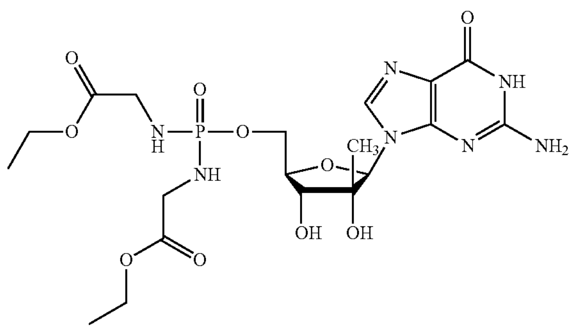 | ++ | + |
| Compound 9: | 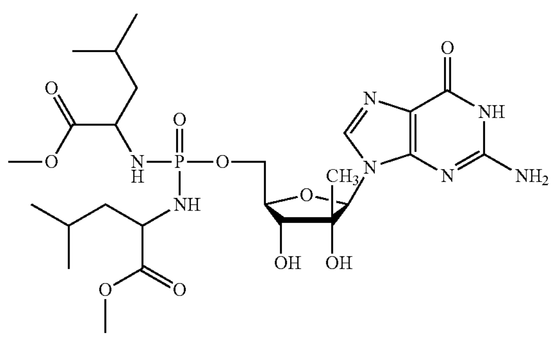 | ++ | + |
| Compound 8: | 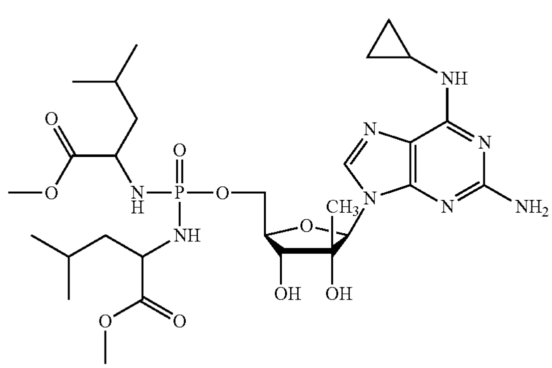 | +++ | + |

-continued
| Compound Reference | Structure | HCV Replicon EC$_{50}$ (µM) | CC$_{50}$ (µM) |
|---|---|---|---|
| Compound 3: | 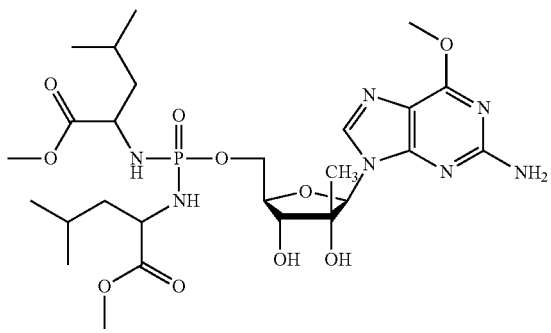 | +++ | + |
| Compound 6: | 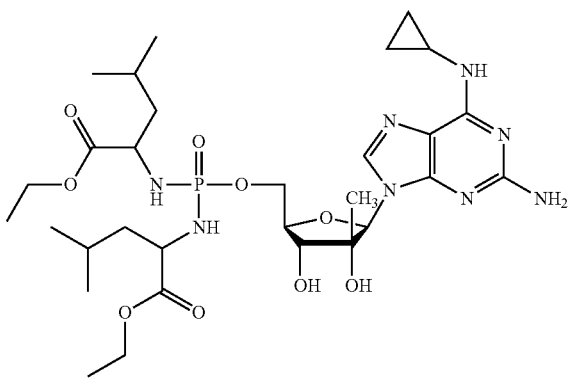 | +++ | + |
| Compound 4: | 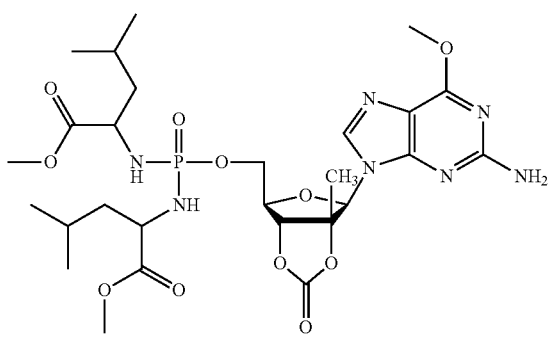 | +++ | + |
| NUCLEOSIDE PARENT: | 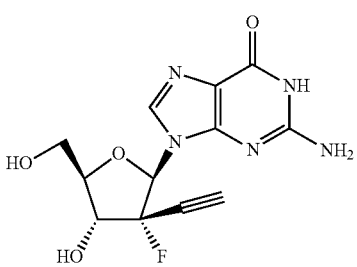 [SMILES: C#C[C@@]1(F)[C@H](O)[C@@H](CO)O[C@H]1n1cnc2c(=O)[nH]c(N)nc21] | + | + |

| Compound Reference | Structure | HCV Replicon EC$_{50}$ (μM) | CC$_{50}$ (μM) |
|---|---|---|---|
| Compound 48: | 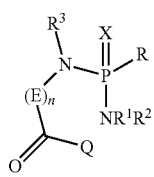 | + | + |

EC$_{50}$ in ELISA 2 assay is provided as follows:
+++ ≤ 1 μm, ++ > 1-10 μm and + > 10 μm
CC$_{50}$ is provided as follows:
++ ≤ 75 μm, + > 75 μm All publications and patent, applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the subject matter limited solely by the scope of the following claims, including equivalents thereof.

What is claimed is:
1. A compound of Formula I:

(I)

or a pharmaceutically acceptable salt, a stereoisomeric, tautomeric or polymorphic form thereof, wherein;
R is a moiety derivable by removal of a hydrogen from a hydroxy group of an antiviral drug;
X is O or S;
Q is OR$^4$, SR$^4$ or NR$^5$R$^6$;
each E is independently CR$^7$R$^8$;
each n is 1 or 2;
R$^1$ and R$^2$ are selected as follows:
i) R$^1$ and R$^2$ are each independently hydrogen, alkyl, alkenyl, alkynyl, aryl, aralkyl, cycloalkyl, cycloalkenyl, alkylheterocyclyl or alkylheteroaryl;
ii) R$^1$ and R$^2$ together with the nitrogen atom on which they are substituted form a 3-7 membered heterocyclic or heteroaryl ring; or
iii) R$^1$ is hydrogen, alkyl or cycloalkyl, and R$^2$ is (G)$_m$C(O)Q$^1$, wherein Q$^1$ is OR$^4$, SR$^4$ or NR$^5$R$^6$;
each G is independently CR$^7$R$^8$; and
each m is 1 or 2;
R$^3$ and R$^4$ are each independently hydrogen, alkyl, alkenyl, alkynyl, aryl, aralkyl, cycloalkyl or cycloalkenyl;
R$^5$ and R$^6$ are selected as follows:
i) R$^5$ and R$^6$ are each independently hydrogen, alkyl, alkenyl, alkynyl, aryl, aralkyl, cycloalkyl or cycloalkenyl; or
ii) R$^5$ and R$^6$ together with the nitrogen atom on which they are substituted form a 3-7 membered heterocyclic or heteroaryl ring; and
R$^7$ and R$^8$ are selected as follows:
i) R$^7$ and R$^8$ are each independently hydrogen, alkyl, alkenyl, alkynyl, aryl, aralkyl, cycloalkyl, cycloalkenyl, alkylheterocyclyl or alkylheteroaryl, wherein alkyl is optionally substituted by alkoxy; or
ii) R$^7$ and R$^8$ together with the carbon atom to which they are attached form a 3-7 membered cycloalkyl ring; and
wherein if R$^2$ is (G)$_m$C(O)Q$^1$, G is CR$^7$R$^8$; m is 1, and one of R$^7$ or R$^8$ is hydrogen, the other of R$^7$ and R$^8$ is isobutyl.

2. The compound of claim 1 of Formula I, wherein R$^7$ and R$^8$ are selected as follows:
i) R$^7$ and R$^8$ are each independently hydrogen, C$_2$-C$_{10}$ alkyl, alkenyl, alkynyl, aryl, aralkyl, cycloalkyl, cycloalkenyl, alkylheterocyclyl or alkylheteroaryl, wherein alkyl is optionally substituted by alkoxy; or
ii) R$^7$ and R$^8$ together with the carbon atom to which they are attached form a 3-7 membered cycloalkyl ring.

3. The compound of claim 1, wherein
R$^1$ and R$^3$ are each hydrogen;
R$^2$ is (G)$_m$C(O)Q$^1$; and
m is 1.

4. The compound of claim 1, wherein
R$^1$ and R$^3$ are each hydrogen;
R$^2$ is (G)$_m$C(O)Q$^1$; and
m is 2.

5. A compound of Formula II:

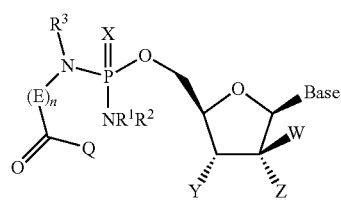

or a pharmaceutically acceptable salt, a stereoisomeric, tautomeric or polymorphic form thereof, wherein;
Base is a substituted or unsubstituted purine or pyrimidine;
W is alkyl, cycloalkyl, alkenyl, cycloalkenyl or alkynyl;
X is O or S;
Y is hydrogen or $OR^9$;
Z is hydrogen, $OR^{10}$, $SR^{10}$, $NR^5R^6$, F, Cl, Br or I;
Q is $OR^4$, $SR^4$ or $NR^5R^6$;
each E is independently $CR^7R^8$;
each n is 1 or 2;
$R^1$ and $R^2$ are selected as follows:
i) $R^1$ and $R^2$ are each independently hydrogen, alkyl, alkenyl, alkynyl, aryl, aralkyl, cycloalkyl, cycloalkenyl, alkylheterocyclyl or alkylheteroaryl;
ii) $R^1$ and $R^2$ together with the nitrogen atom on which they are substituted form a 3-7 membered heterocyclic or heteroaryl ring; or
iii) $R^1$ is hydrogen, alkyl or cycloalkyl, and $R^2$ is $(G)_mC(O)Q^1$, wherein
$Q^1$ is $OR^4$, $SR^4$ or $NR^5R^6$;
each G is independently $CR^7R^8$; and
each m is 1 or 2;
$R^3$ and $R^4$ are each independently hydrogen, alkyl, alkenyl, alkynyl, aryl, aralkyl, cycloalkyl or cycloalkenyl;
$R^5$ and $R^6$ are selected as follows:
i) $R^5$ and $R^6$ are each independently hydrogen, alkyl, alkenyl, alkynyl, aryl, aralkyl, cycloalkyl or cycloalkenyl; or
ii) $R^5$ and $R^6$ together with the nitrogen atom on which they are substituted form a 3-7 membered heterocyclic or heteroaryl ring;
$R^7$ and $R^8$ are selected as follows:
i) $R^7$ and $R^8$ are each independently hydrogen, alkyl, alkenyl, alkynyl, aryl, aralkyl, cycloalkyl, cycloalkenyl, alkylheterocyclyl or alkylheteroaryl, wherein alkyl is optionally substituted by alkoxy; or
ii) $R^7$ and $R^8$ together with the carbon atom to which they are attached form a 3-7 membered cycloalkyl ring;
$R^9$ and $R^{10}$ are selected as follows:
i) $R^9$ and $R^{10}$ are each independently hydrogen, alkyl, alkenyl, alkynyl, aryl, aralkyl, cycloalkyl or cycloalkenyl; or
ii) $R^9$ and $R^{10}$ together with C(O) and the oxygen or sufur atoms on which they are substituted form a 5 membered ring.

6. The compound of claim 5, wherein if $R^2$ is $(G)_mC(O)Q^1$, G is $CR^7R^8$, m is 1, and one of $R^7$ or $R^8$ is hydrogen; the other of $R^7$ and $R^8$ is not methyl.

7. The compound of claim 5, wherein Y is $OR^9$ and Z is $OR^{10}$ or F.

8. The compound of claim 5, wherein W is alkyl.

9. The compound of claim 5, wherein W is ethynyl; Y is $OR^9$; Z is F; and $R^9$ is hydrogen.

10. The compound of claim 5, wherein each $R^7$ is hydrogen and each $R^8$ is independently alkyl, aryl, aralkyl or alkylheteroaryl.

11. The compound of claim 10, wherein each $R^8$ is $C_2$-$C_{10}$ alkyl.

12. The compound of claim 10, wherein each $R^8$ is isobutyl, sec-butyl, phenyl or benzyl.

13. The compound of claim 5, wherein each $R^7$ is hydrogen and each $R^8$ is alkyl optionally substituted by alkoxy.

14. The compound of claim 13, wherein each $R^8$ is t-butoxymethyl.

15. The compound of claim 5, wherein each of $R^7$ and $R^8$ is alkyl.

16. The compound of claim 15, wherein each of $R^7$ and $R^8$ is methyl.

17. The compound of claim 5, wherein $R^7$ and $R^8$ together with the carbon atom to which they are attached form a 5 membered cycloalkyl ring.

18. The compound of claim 5, wherein Base is adenine, cytosine, guanine, hypoxanthine, thymine or uridine.

19. The compound of claim 18, wherein Base is cytosine.

20. The compound of claim 18, wherein Base is guanine.

21. The compound of claim 18, wherein Base is uridine.

22. The compound of claim 1, wherein R is a moiety derivable by removal of a hydrogen from a hydroxy group of selected from ribavirin, viramidine, valopicitabine, PSI-6130, PSI-6206, PSI-35938 and R1479.

23. The compound of claim 5 or a pharmaceutically acceptable salt, a stereoisomeric, tautomeric or polymorphic form thereof, selected from:

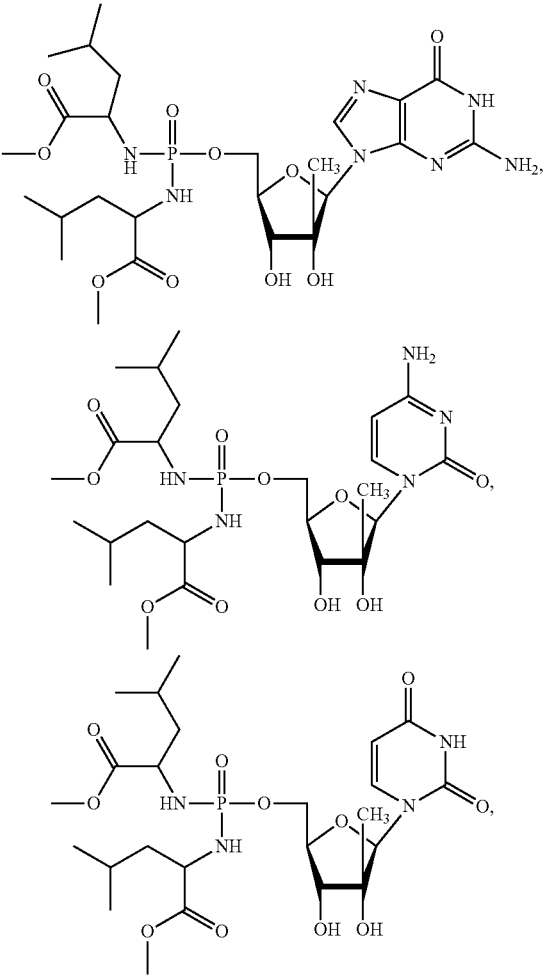

121
-continued
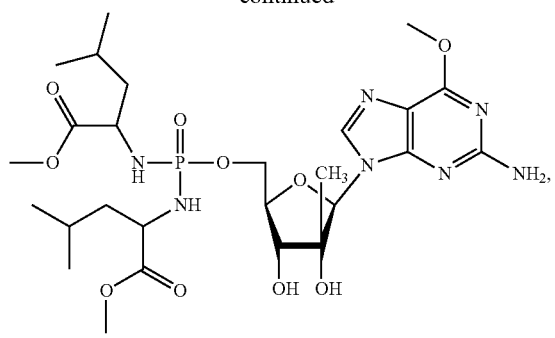
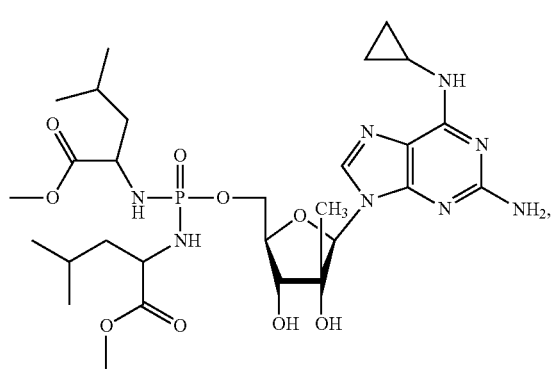
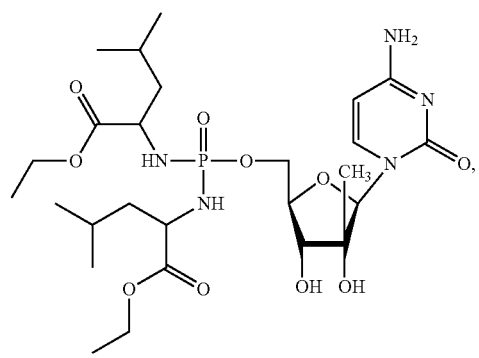
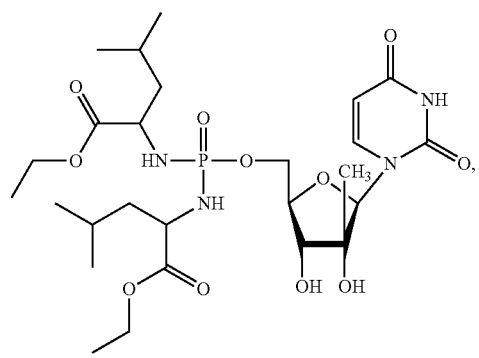
122
-continued
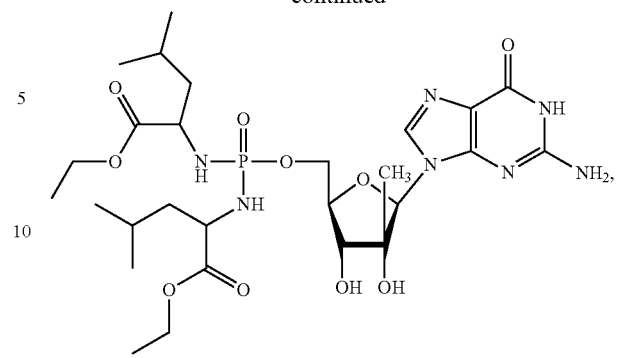
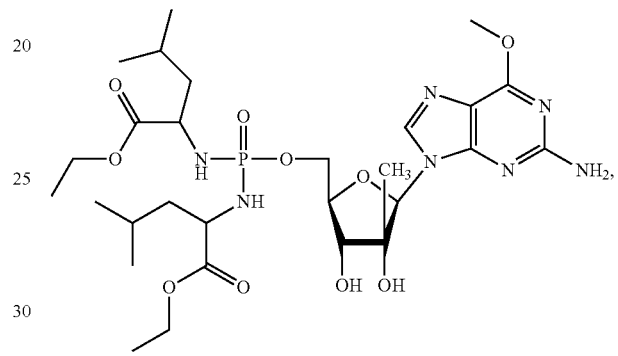
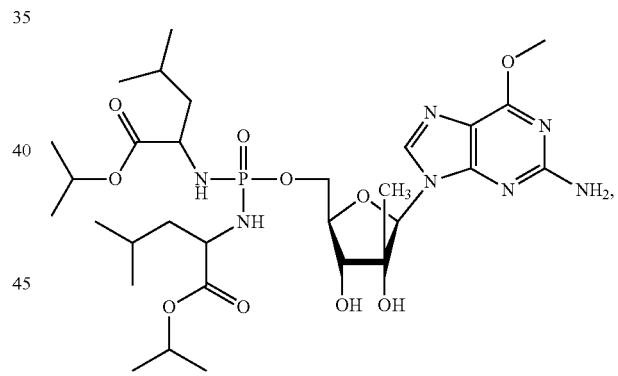
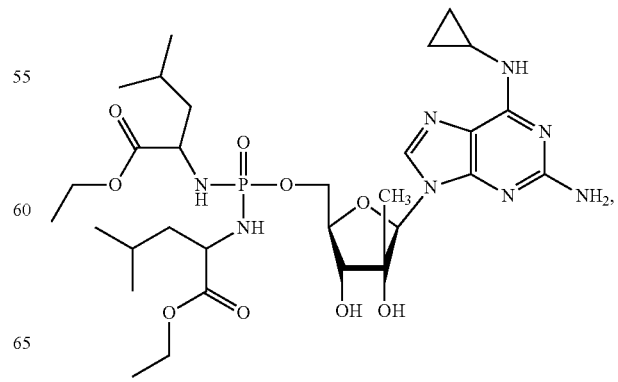

123
-continued
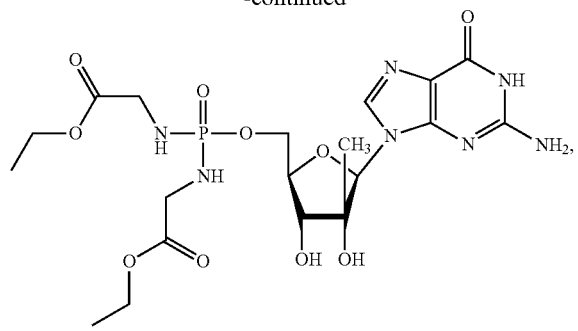
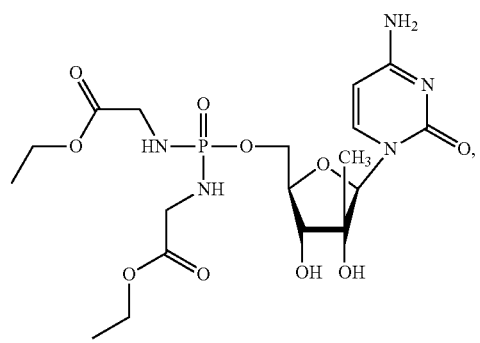
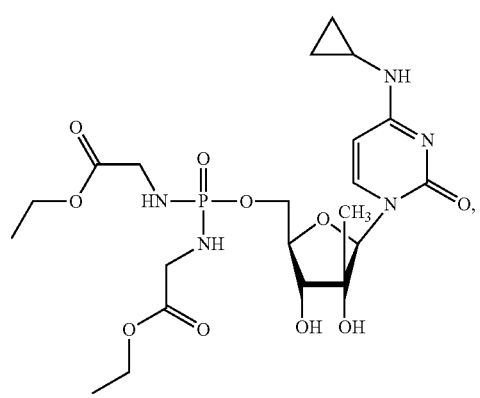
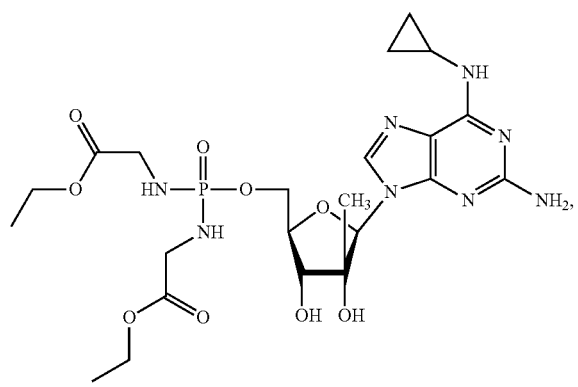
124
-continued
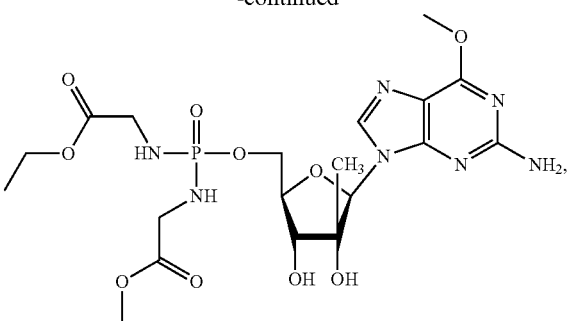
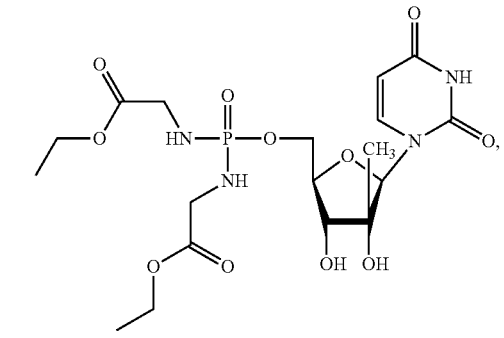
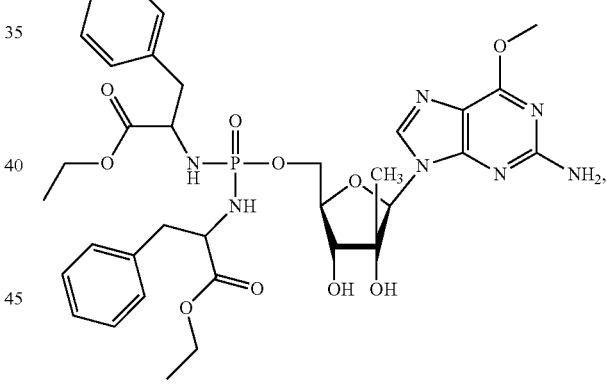
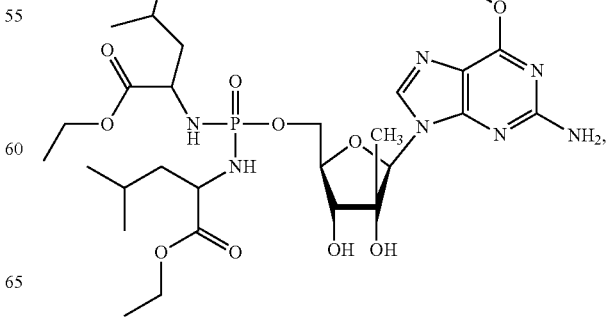

125
-continued
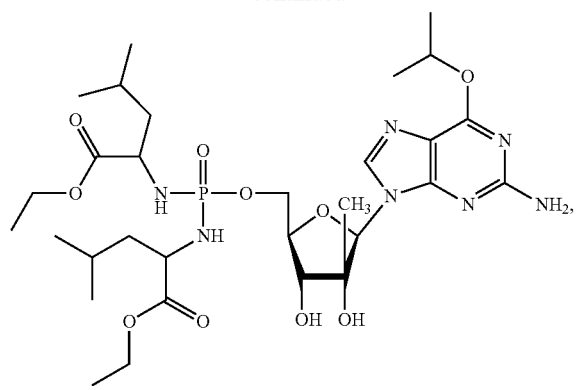
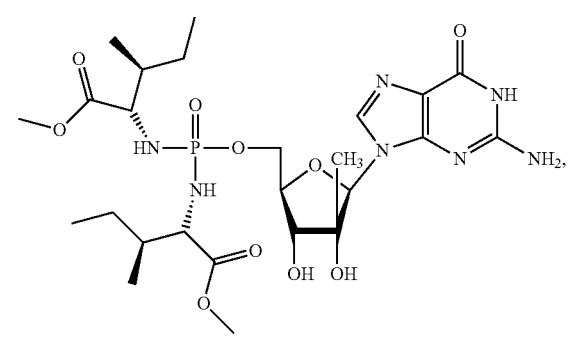
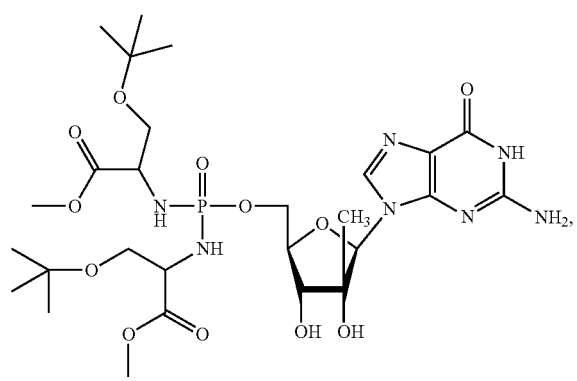
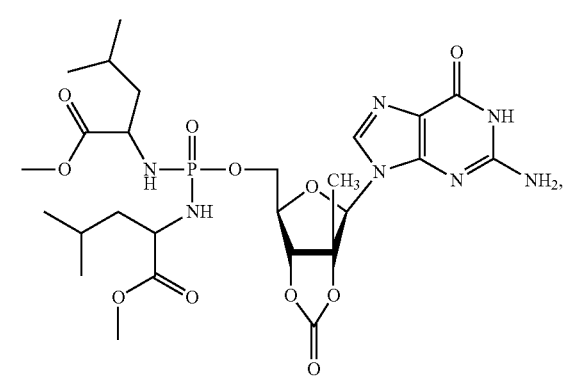
126
-continued
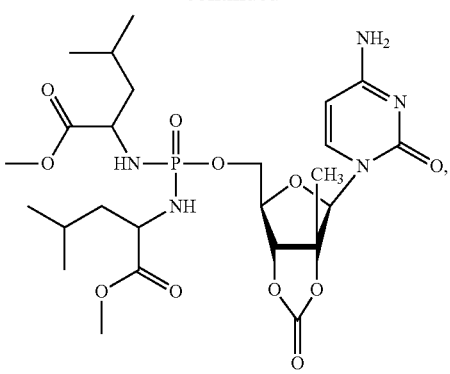
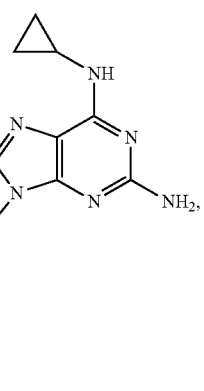

127
-continued
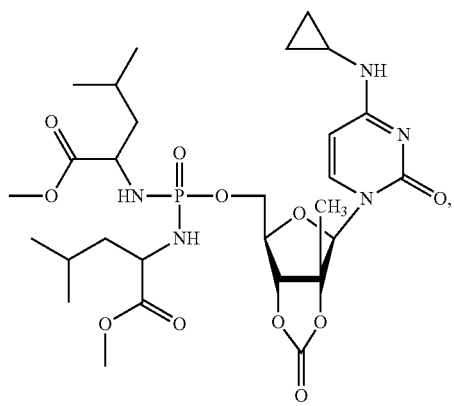
128
-continued
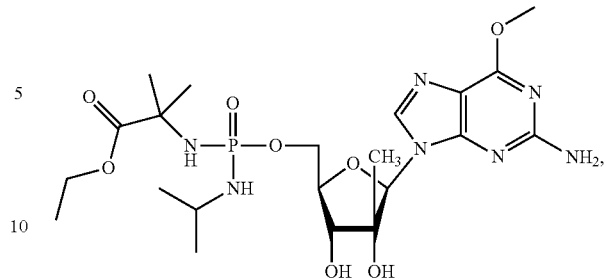
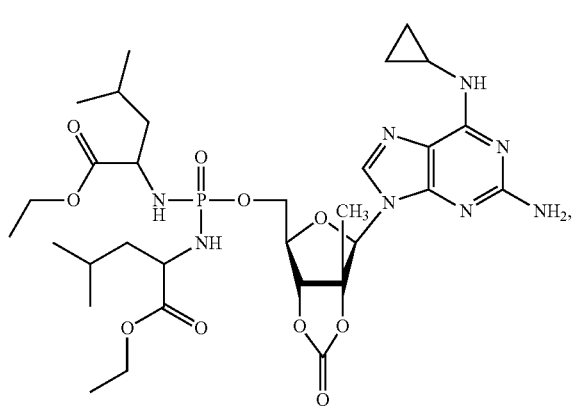
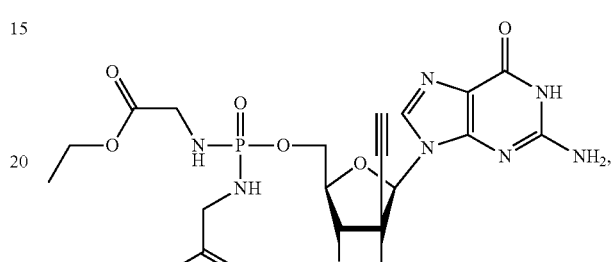
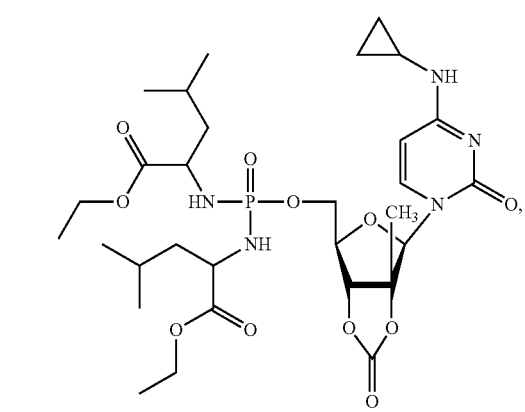
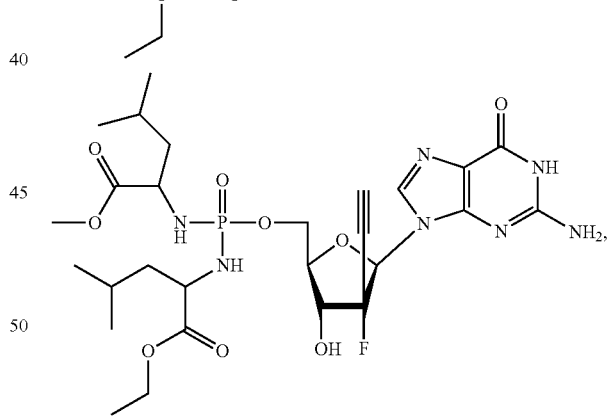
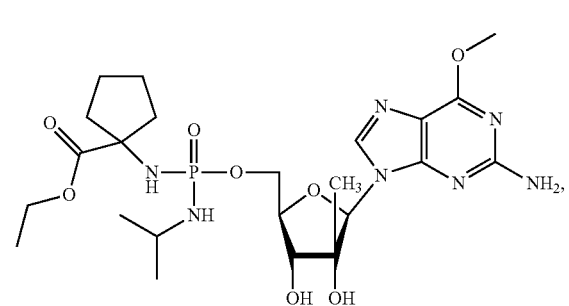
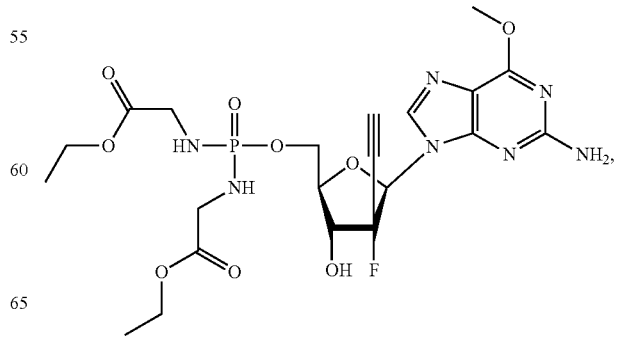

129
-continued
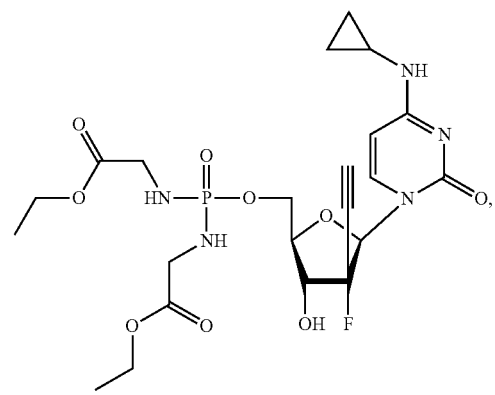
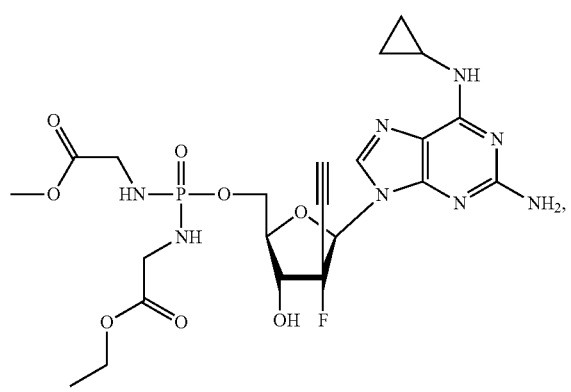
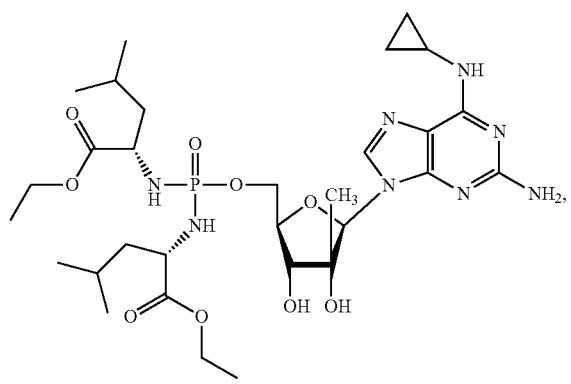
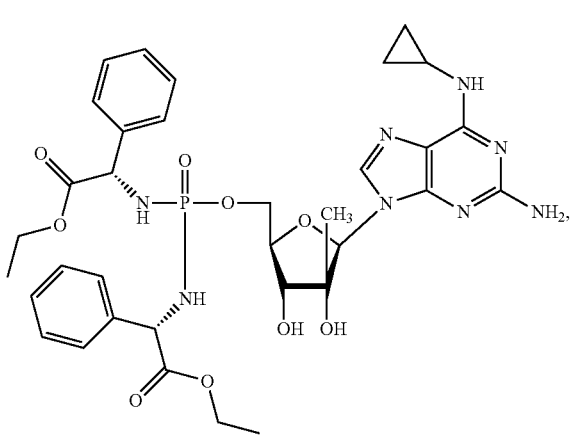
130
-continued
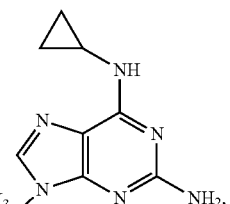
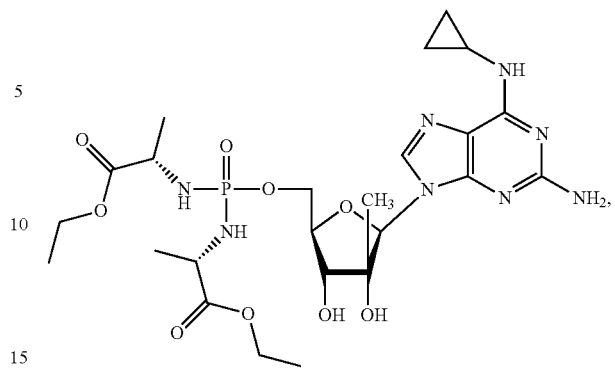
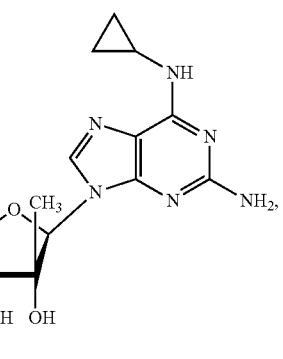
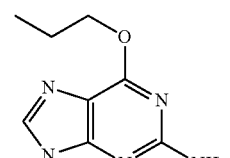
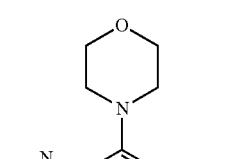

131
-continued
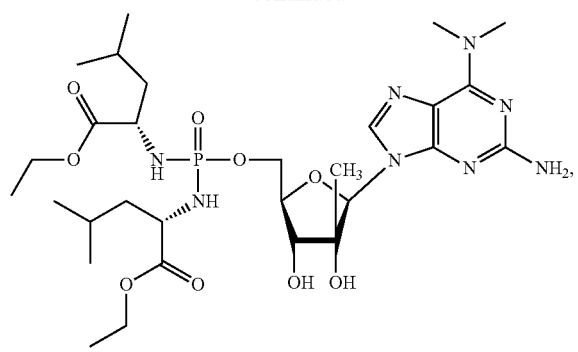
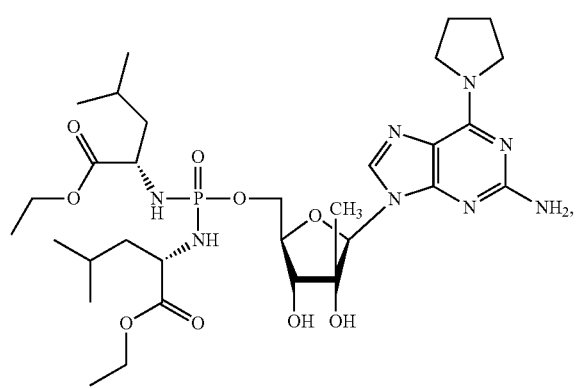
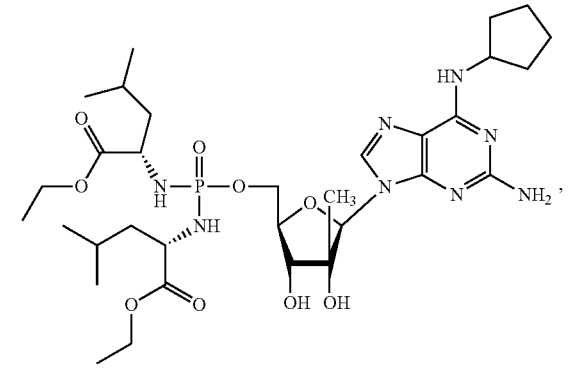
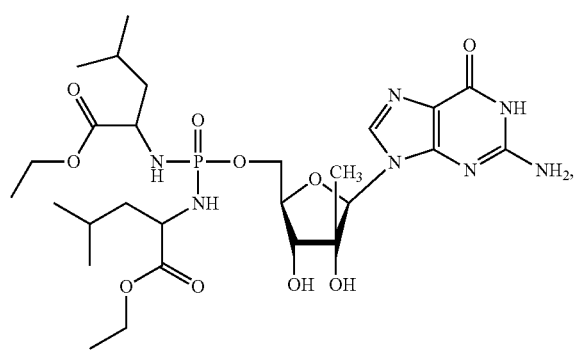
132
-continued
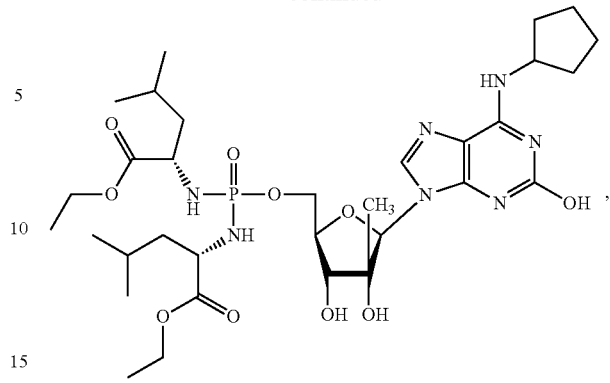
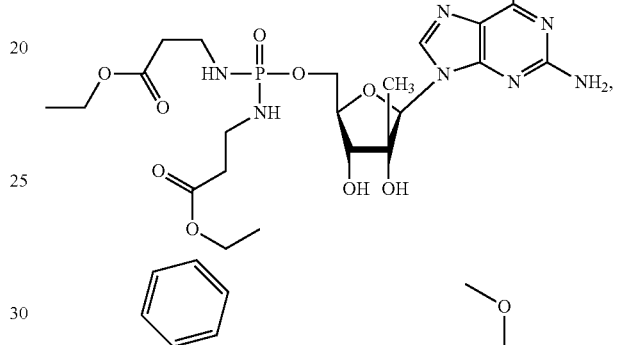
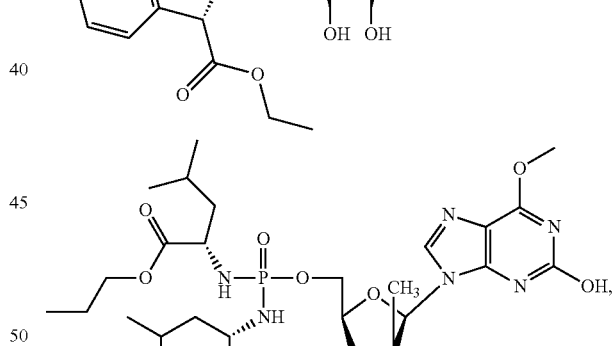
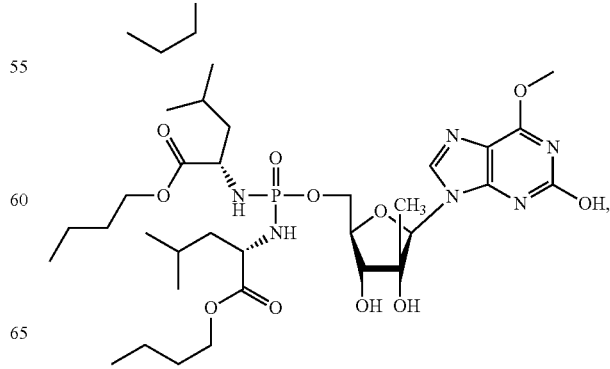

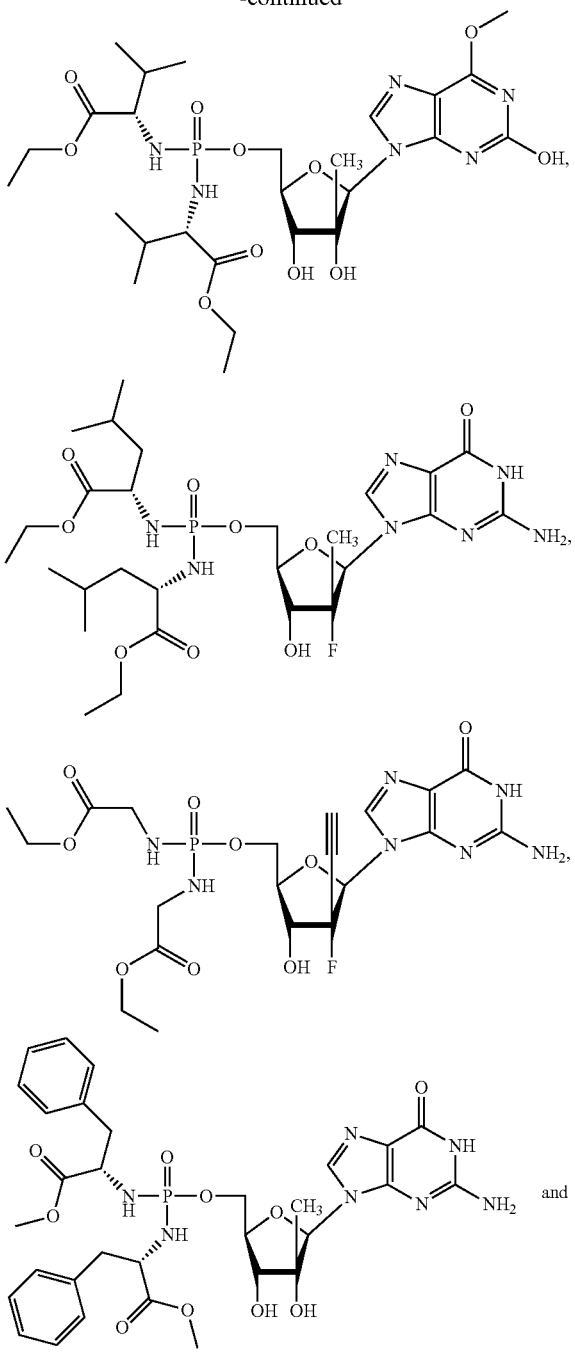

24. A pharmaceutical composition comprising a compound of claim 5 and a pharmaceutically acceptable excipient, carrier or diluent.

25. The pharmaceutical composition of claim 24, wherein the composition is an oral formulation.

26. A method for the treatment of a host infected with a hepatitis C virus, comprising the administration of an effective treatment amount of a compound of claim 1.

27. The method of claim 26, wherein the host is a human.

28. The method of claim 26, wherein said administration directs a substantial amount of said compound or pharmaceutically acceptable salt or stereoisomer thereof to the liver of said host.

29. The method of claim 26, wherein said compound or composition is administered in combination or alternation with a second anti-viral agent optionally selected from the group consisting of an interferon, a ribavirin, an interleukin, a NS3 protease inhibitor, a cysteine protease inhibitor, a phenanthrenequinone, a thiazolidine derivative, a thiazolidine, a benzanilide, a helicase inhibitor, a polymerase inhibitor, a nucleotide analogue, a gliotoxin, a cerulenin, an antisense phosphorothioate oligodeoxynucleotide, an inhibitor of IRES-dependent translation, and a ribozyme.

30. The compound of claim 1 where the antiviral drug is a nucleoside or nucleoside analog.

* * * * *